United States Patent
Smith

(10) Patent No.: US 12,188,920 B2
(45) Date of Patent: Jan. 7, 2025

(54) DETERMINING PROPERTIES OF MATERIALS THROUGH CONDITIONALLY RELEASABLE MATERIAL-ASSOCIATED LIQUIDS

(71) Applicant: Michael P. Smith, Tulsa, OK (US)

(72) Inventor: Michael P. Smith, Tulsa, OK (US)

(*) Notice: Subject to any disclaimer, the term of this patent is extended or adjusted under 35 U.S.C. 154(b) by 464 days.

(21) Appl. No.: 17/720,217

(22) Filed: Apr. 13, 2022

(65) Prior Publication Data

US 2022/0283138 A1 Sep. 8, 2022

Related U.S. Application Data

(63) Continuation of application No. PCT/US2020/055436, filed on Oct. 13, 2020.

(60) Provisional application No. 62/915,012, filed on Oct. 14, 2019, provisional application No. 62/914,551, filed on Oct. 13, 2019.

(51) Int. Cl.
*G01N 33/28* (2006.01)
*E21B 49/08* (2006.01)
*G01N 33/24* (2006.01)

(52) U.S. Cl.
CPC ....... *G01N 33/2823* (2013.01); *G01N 33/241* (2013.01); *G01N 33/246* (2013.01); *E21B 49/081* (2013.01)

(58) Field of Classification Search
CPC ............. G01N 33/2823; G01N 33/241; G01N 33/246; E21B 49/081
See application file for complete search history.

(56) References Cited

U.S. PATENT DOCUMENTS

| | | | |
|---|---|---|---|
| 4,495,414 A | 1/1985 | Barrie et al. | |
| 4,525,328 A | 6/1985 | Bredeweg | |
| 4,608,859 A * | 9/1986 | Rockley | E21B 49/005 73/152.05 |
| 4,774,831 A | 10/1988 | Nordin | |
| 4,797,906 A | 1/1989 | Smith | |

(Continued)

FOREIGN PATENT DOCUMENTS

| | | |
|---|---|---|
| BR | 1120190119442 | 4/2023 |
| CA | 2068012 A1 | 12/1992 |

(Continued)

OTHER PUBLICATIONS

Non-Final Office Action on May 17, 2018 for U.S. Appl. No. 15/908,760.

(Continued)

*Primary Examiner* — Alexander Satanovsky
*Assistant Examiner* — Sharah Zaab
(74) *Attorney, Agent, or Firm* — Transformative Legal LLC; Len S. Smith; Denise M. Brown

(57) ABSTRACT

The invention described here provides new methods of analyzing materials, e.g., geologic materials, to identify wettability characteristics of such materials. Methods of the invention comprise analyzing the amount of easily extracted water obtained from samples of a material, such as a geologic area, analyzing release resistant water obtained from such samples or co-located samples, and/or optionally calculating or analyzing the combined water in or obtained from such samples, and utilizing such values alone or in comparison to one another to assess the wettability characteristics of the material.

20 Claims, 28 Drawing Sheets

(56) References Cited

U.S. PATENT DOCUMENTS

| | | | |
|---|---|---|---|
| 4,960,567 A | 10/1990 | Smith | |
| 5,241,859 A | 9/1993 | Smith | |
| 5,286,651 A | 2/1994 | Smith | |
| 5,328,849 A | 7/1994 | Smith | |
| 5,341,859 A | 8/1994 | Howseman, Jr. | |
| 5,411,707 A | 5/1995 | Hiatt | |
| 5,416,024 A | 5/1995 | Smith | |
| 5,447,556 A | 9/1995 | Pleil et al. | |
| 5,457,316 A | 10/1995 | Cohen et al. | |
| 5,767,399 A * | 6/1998 | Smith | E21B 49/006 702/10 |
| 6,541,272 B1 | 4/2003 | Mitra | |
| 6,661,000 B2 | 12/2003 | Smith | |
| 6,743,397 B1 | 6/2004 | Zesiger | |
| 7,150,184 B1 | 12/2006 | Scott et al. | |
| 7,210,342 B1 * | 5/2007 | Sterner | E21B 21/01 73/152.23 |
| 7,354,768 B1 * | 4/2008 | Scott | G01N 33/2847 436/39 |
| 7,395,691 B2 | 7/2008 | Sterner | |
| 8,256,282 B2 | 9/2012 | Schlachter | |
| 8,536,524 B2 | 9/2013 | Pomerantz | |
| 2001/0015093 A1 | 8/2001 | Kempe | |
| 2002/0194896 A1 | 12/2002 | Stolper | |
| 2004/0099804 A1 | 5/2004 | Liu | |
| 2005/0109207 A1 | 5/2005 | Olander | |
| 2005/0194134 A1 | 9/2005 | McGregor | |
| 2006/0000110 A1 | 1/2006 | Aisenberg et al. | |
| 2010/0277724 A1 | 11/2010 | Bounouar | |
| 2011/0305309 A1 | 12/2011 | Brown | |
| 2012/0167786 A1 | 7/2012 | Augharn, Jr. | |
| 2012/0186331 A1 | 7/2012 | Tipler | |
| 2014/0026638 A1 | 1/2014 | Bowers, II | |
| 2014/0104615 A1 | 4/2014 | Kaneko et al. | |
| 2014/0220700 A1 | 8/2014 | Alexander | |
| 2014/0283580 A1 | 9/2014 | Rouchon | |
| 2015/0123670 A1 | 5/2015 | Robbat, Jr. | |
| 2015/0155150 A1 | 6/2015 | Bateman | |
| 2015/0167052 A1 | 6/2015 | Griffin | |
| 2015/0346179 A1 | 12/2015 | Pillot | |
| 2016/0222781 A1 | 8/2016 | Lawson | |
| 2016/0341707 A1 * | 11/2016 | Inan | G01N 33/24 |
| 2018/0195383 A1 * | 7/2018 | Smith | E21B 49/02 |
| 2018/0306031 A1 | 10/2018 | Smith | |
| 2018/0355717 A1 | 12/2018 | Smith | |
| 2020/0080419 A1 | 3/2020 | Smith | |

FOREIGN PATENT DOCUMENTS

| | | |
|---|---|---|
| CN | 1609586 A | 4/2005 |
| CN | 201740685 U | 2/2011 |
| CN | 104407089 A | 3/2015 |
| EP | 0414564 A2 | 2/1991 |
| EP | 0414564 B1 | 10/1995 |
| WO | WO2003050844 A1 | 6/2003 |
| WO | WO2015050832 A1 | 4/2015 |
| WO | WO2016186689 A1 | 11/2016 |
| WO | 2018111945 | 6/2018 |
| WO | 2020146859 | 7/2020 |

OTHER PUBLICATIONS

European Search Report on Feb. 24, 2023 for EP17880886.
Extended European Search Report on Jul. 30, 2020 for EP178808861.
Indian Examination Report on May 16, 2021 for IN2019170221802.
International Search Report on Apr. 6, 2018 for PCT/US2017/065921.
Jorge et al. "Analysis of Volatiles in Fluid Inclusions by Direction online Crushing Mass Spectrometry." Journal of Brazilian Chem Society 22.3, 2011: 43-455, p. 445, vol. 1 [online]. http://www.scielo.br/pdf/jbchs/v22n3/v22n3a05.ped Published Oct. 19, 2010.
Mazidi et al. "Measurement of Uniaxial Compressive Strength of Rocks Using Reconstructed Cores from Rock Cuttings." Journal of Petroleum Science and Engineering 86-87 (Mar. 2012): 39-43.
McCarthy et al. "Basic Petroleum Geochemistry for Source Rock Evaluation." Oilfield Review, 23.2, Summer 2011.
Non-Final Office Action on Oct. 9, 2018 for U.S. Appl. No. 16/019,523.
Final Office Action on May 2, 2019 for U.S. Appl. No. 16/019,523.
Russian Office Action on Aug. 19, 2020 for EA201991461.
Non-Final Office Action on Oct. 9, 2018 for U.S. Appl. No. 16/019,529.
International Search Report and Written Opinion on Aug. 5, 2019 for PCT/US2019/22362.
International Search Report and Written Opinion for PCT/US2020/013261 dated Jun. 5, 2020.
International Search Report for PCT/US2020/055436 dated Feb. 2, 2021.
Claims of U.S. Appl. No. 17/548,295, filed Dec. 10, 2021, with the earliest priority date of Dec. 14, 2016.
Abdallah, W., et al., Jun. 2007. Fundamentals of Wettability. Schlumberger Oilfield Review, 19(2): 44-61.

* cited by examiner

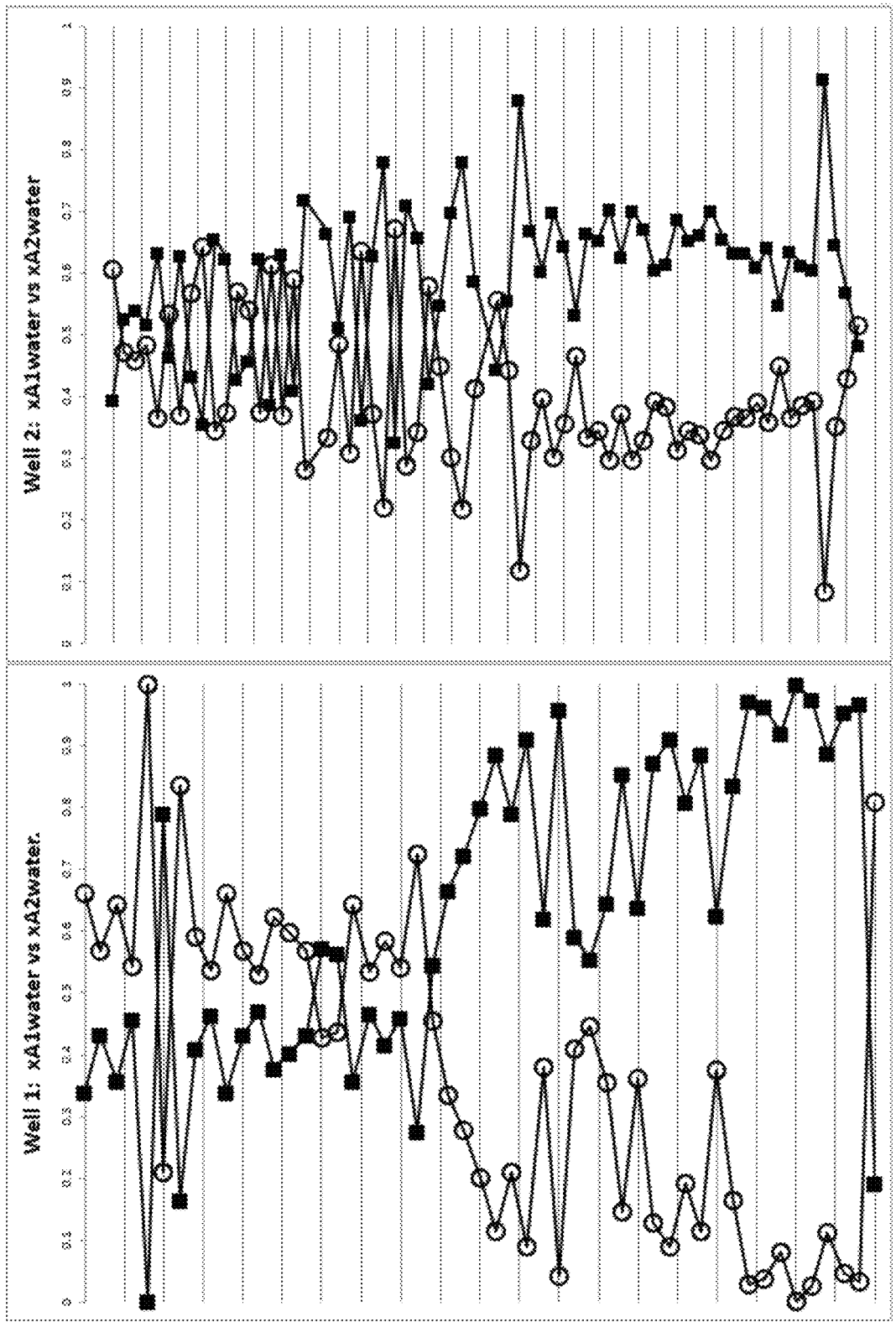

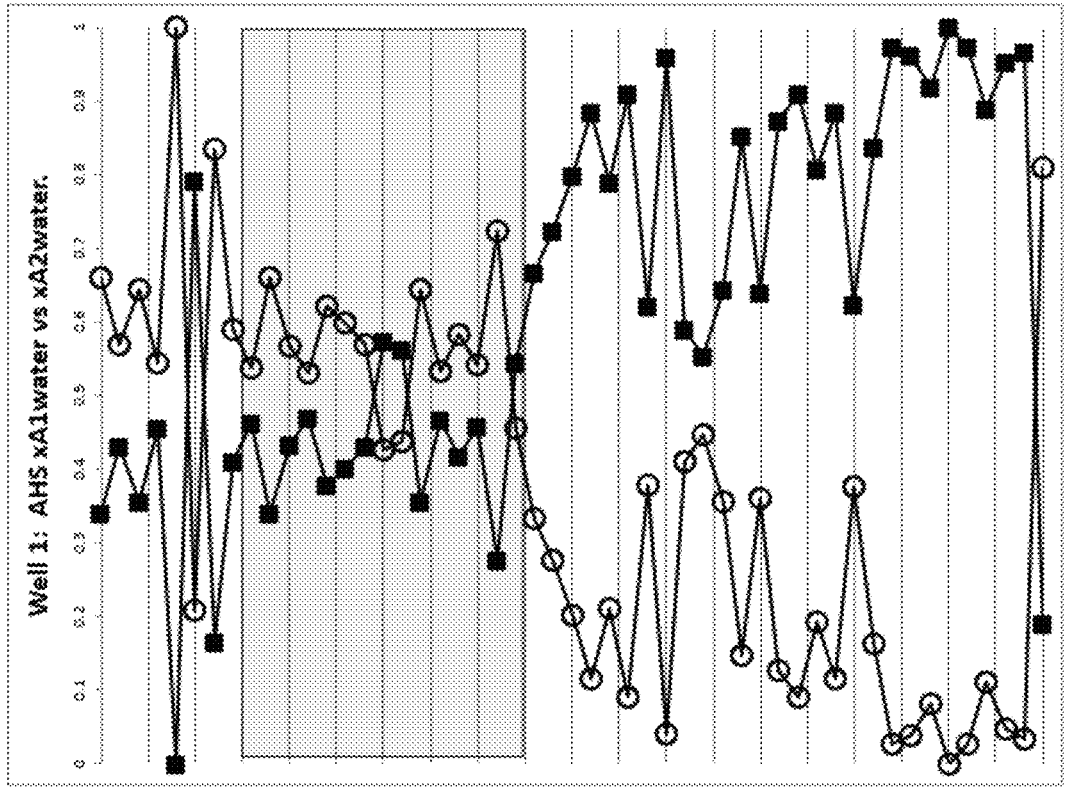

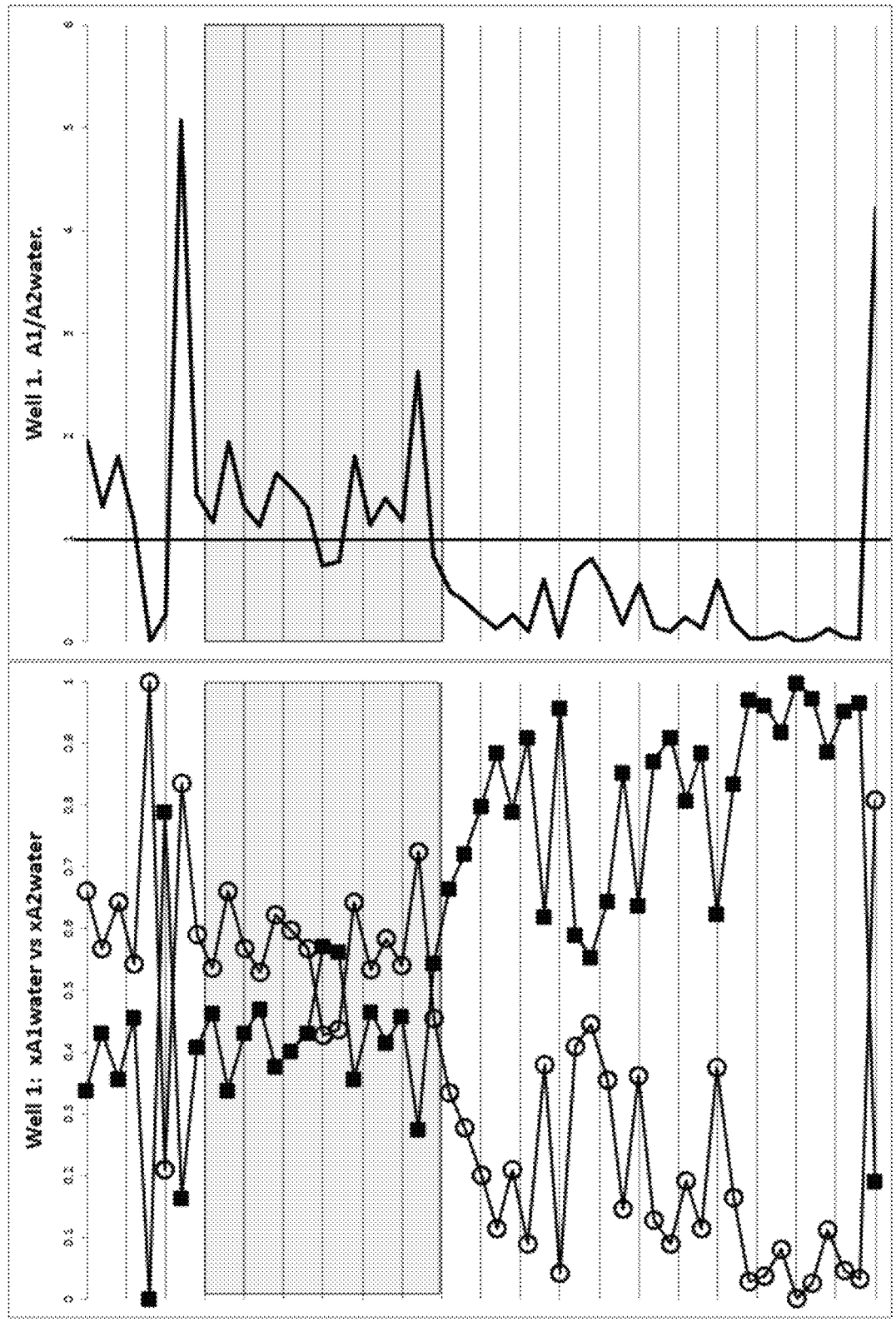

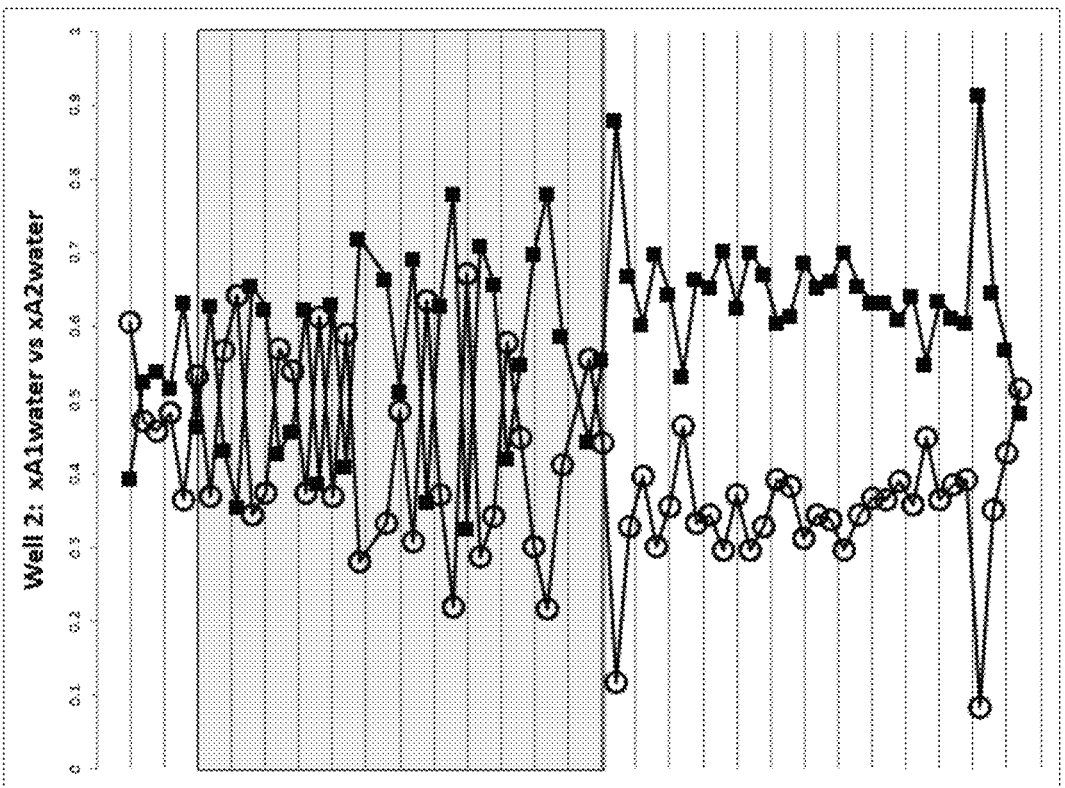
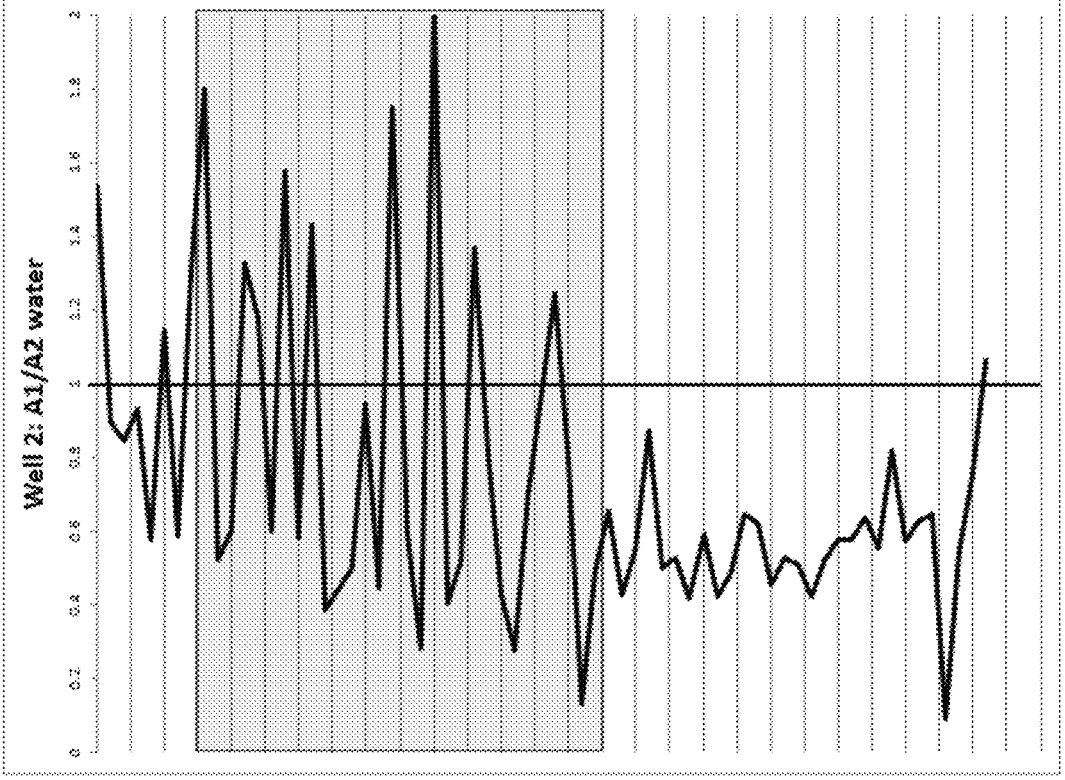

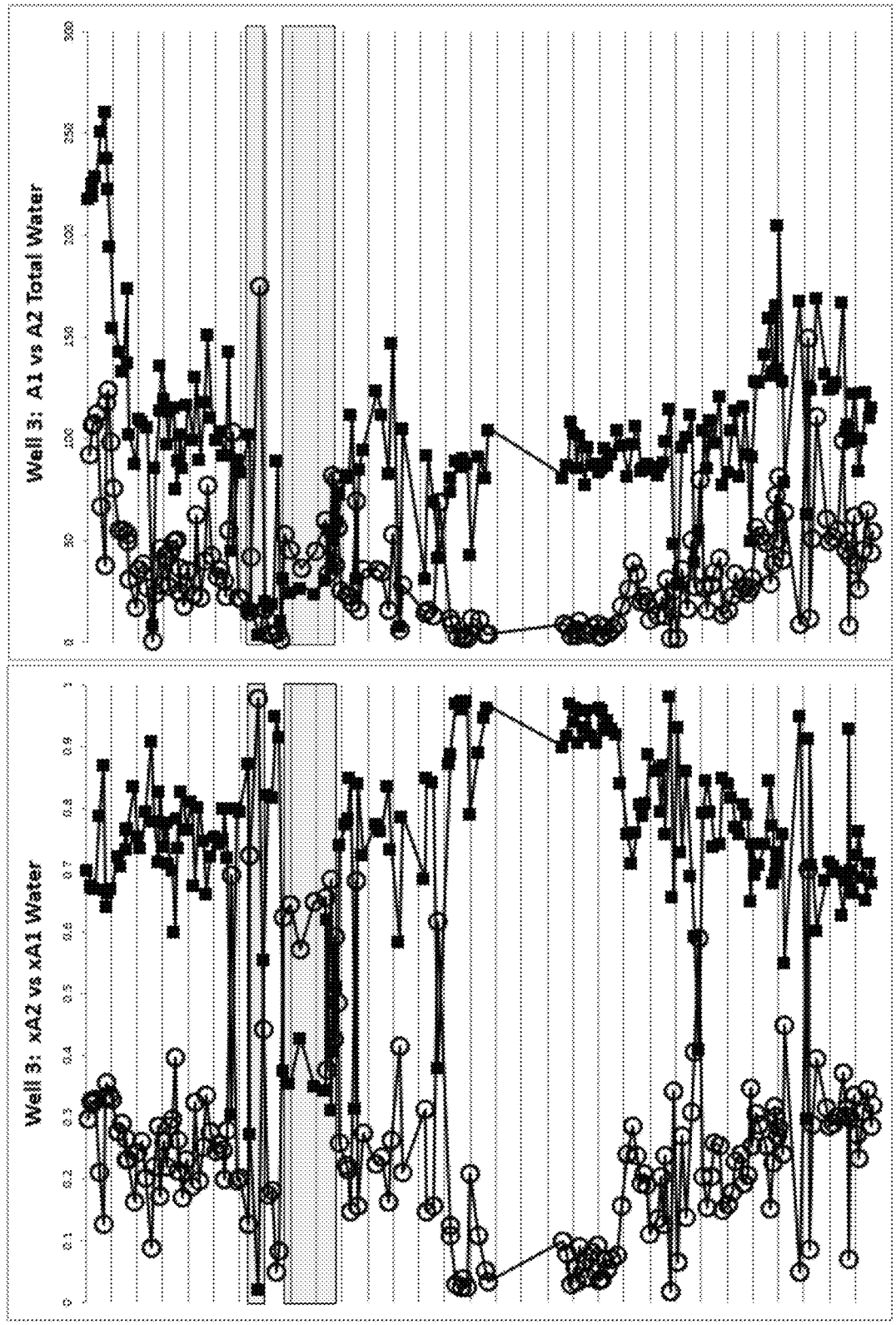

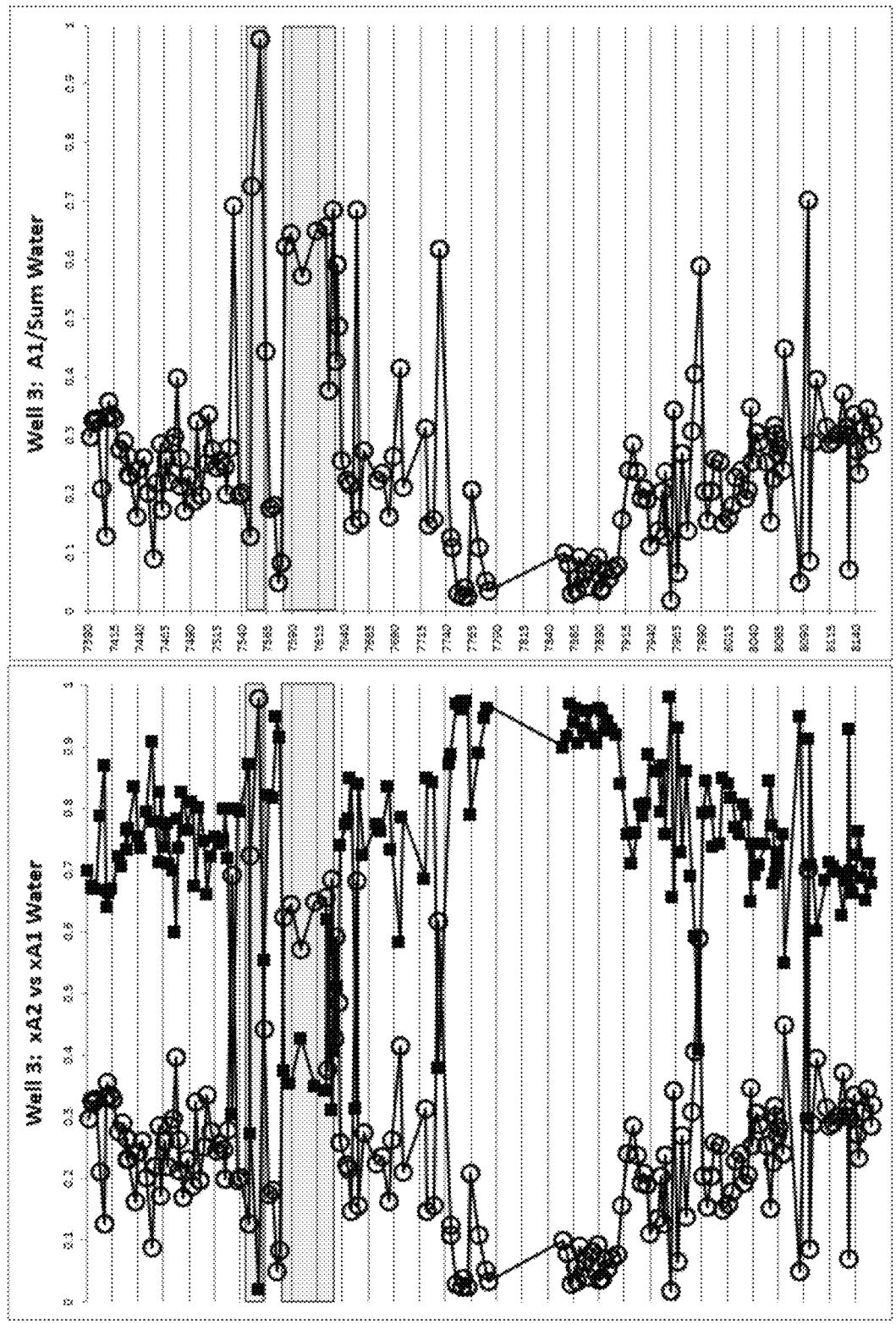

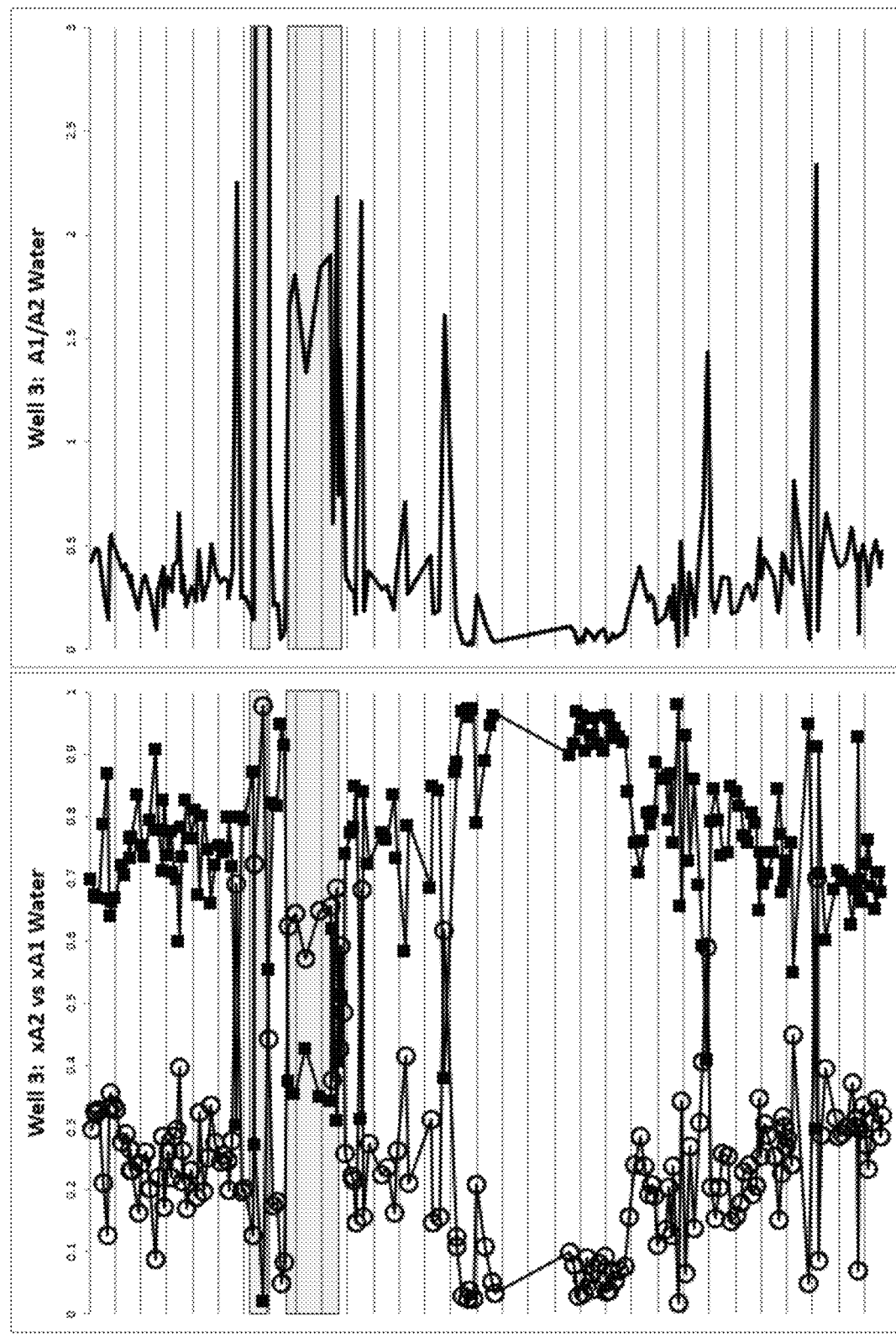

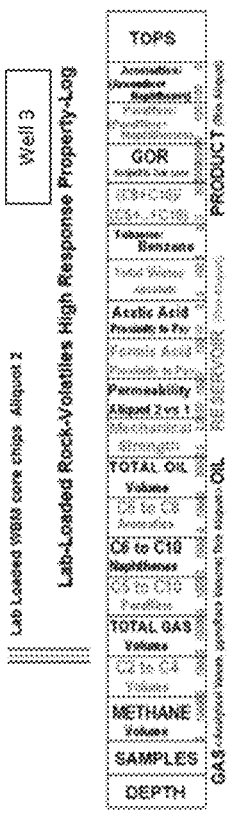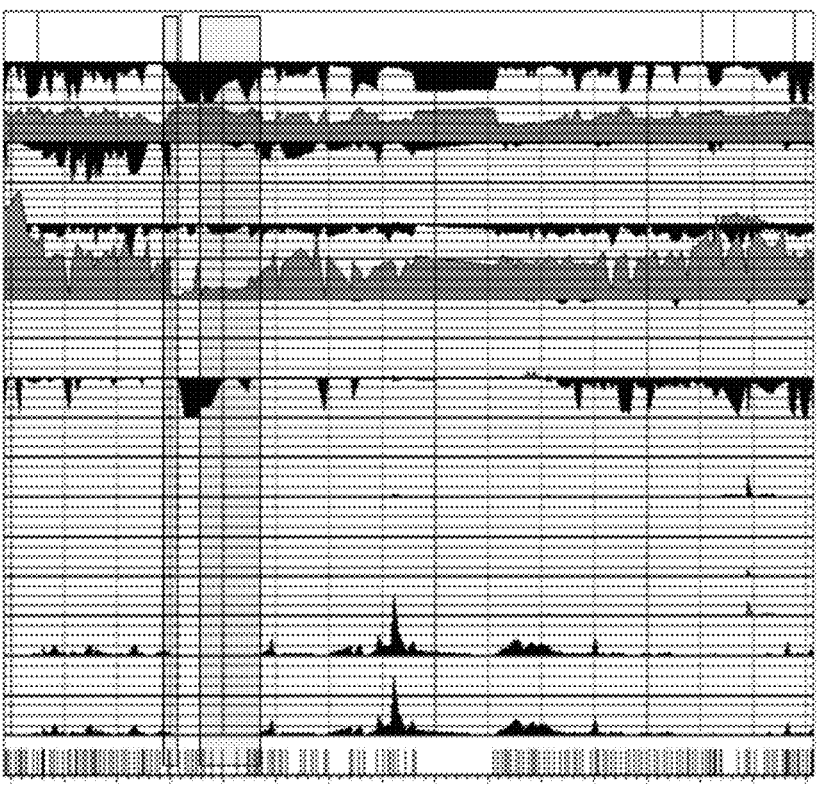
FIGURE 17
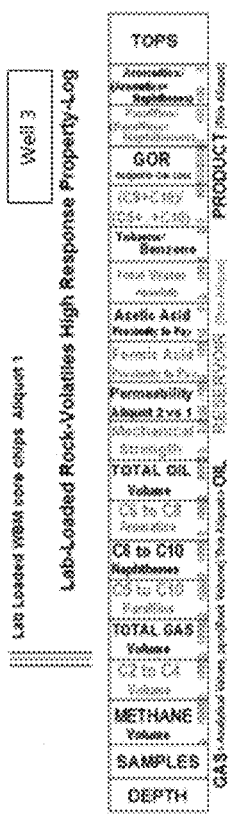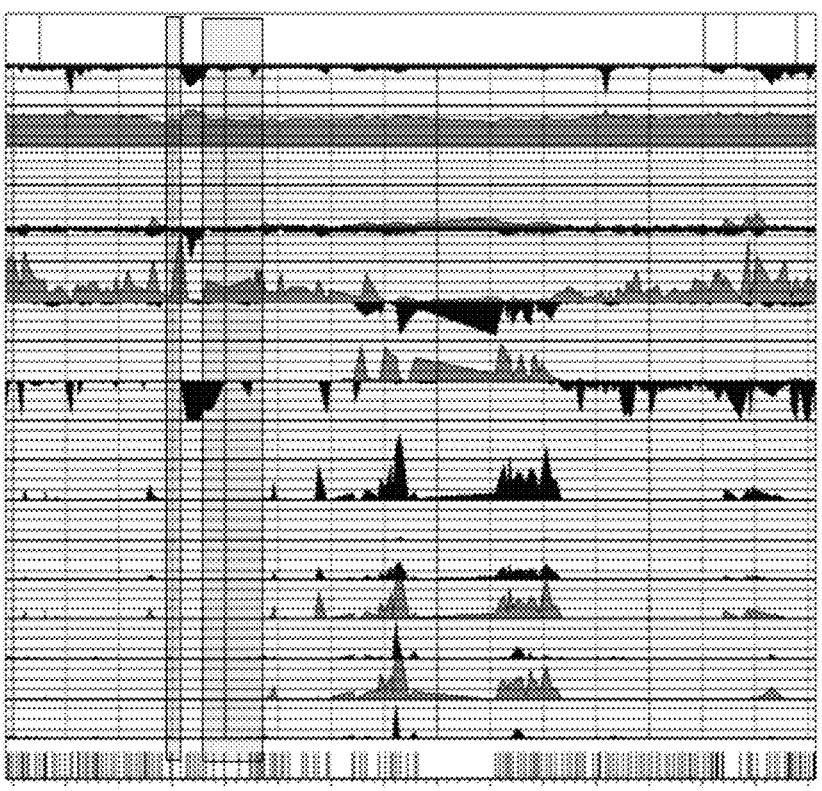
FIGURE 18

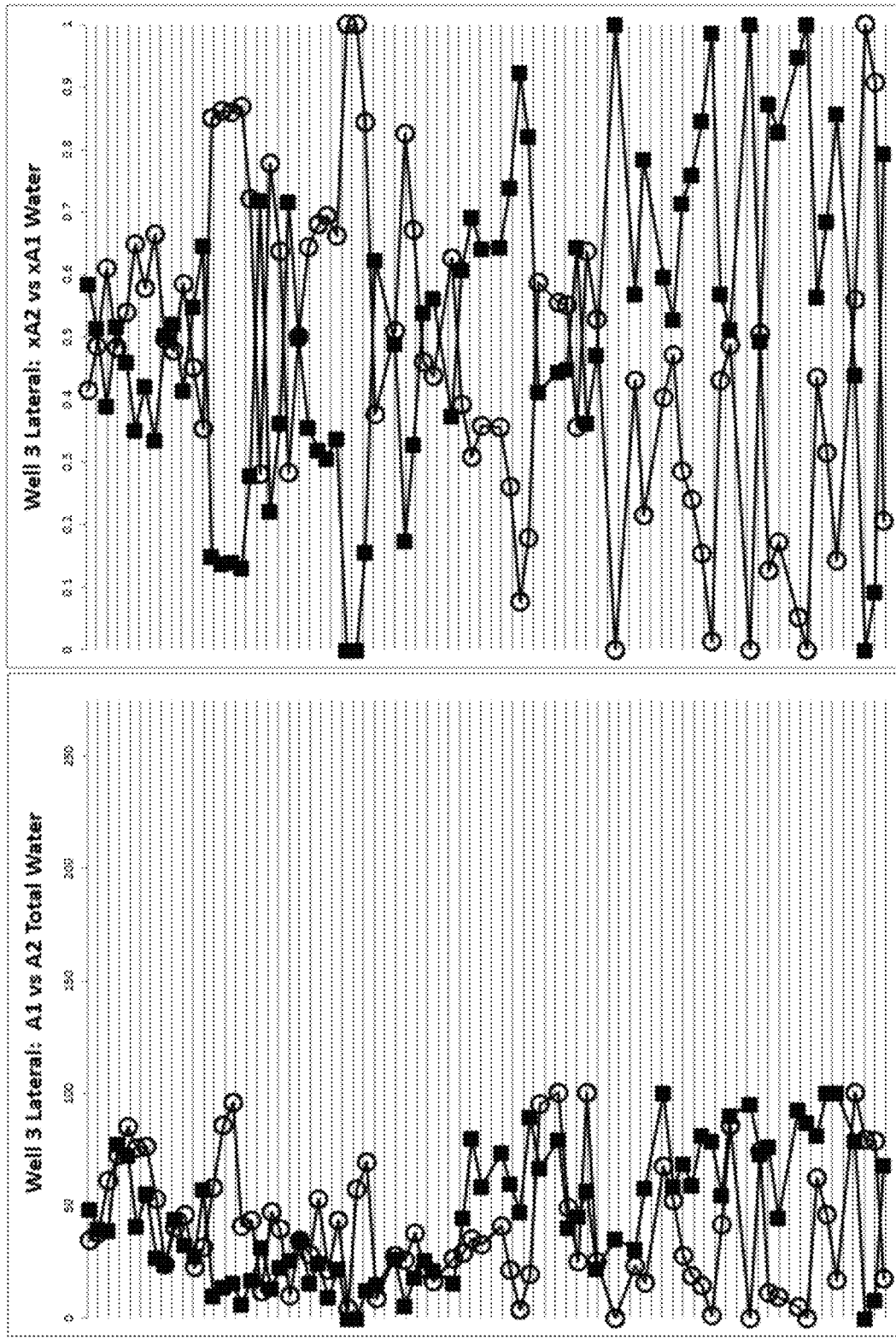

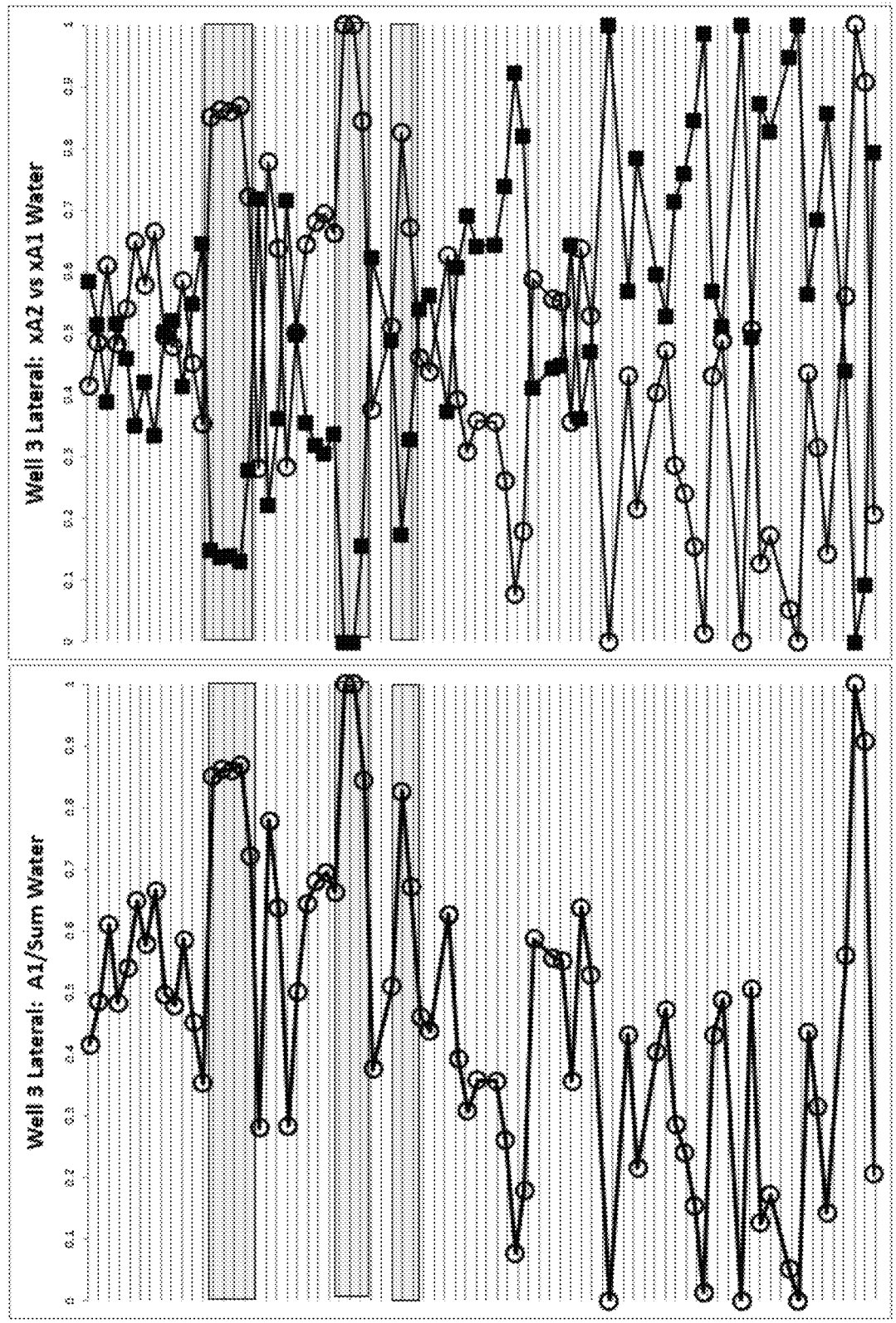

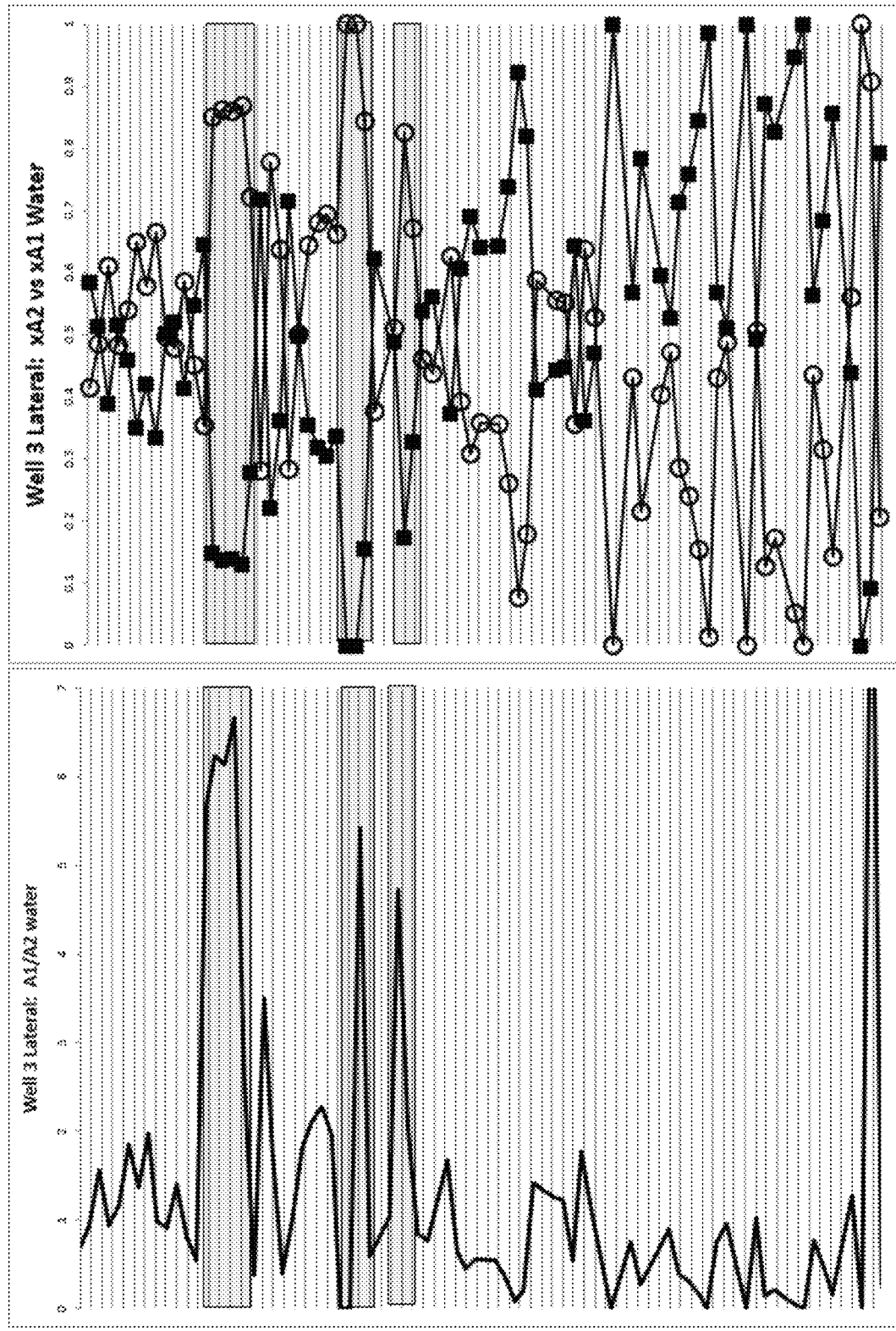

DETERMINING PROPERTIES OF MATERIALS THROUGH CONDITIONALLY RELEASABLE MATERIAL-ASSOCIATED LIQUIDS

CROSS-REFERENCE TO RELATED APPLICATIONS

This patent application is a Continuation of and claims priority to presently co-pending PCT Application Number PCT/US2020/055436, entitled "DETERMINING PROPERTIES OF MATERIALS THROUGH CONDITIONALLY-RELEASABLE MATERIAL-ASSOCIATED LIQUIDS," filed Oct. 13, 2020, which claims the benefit of priority to U.S. Provisional Application No. 62/914,551, entitled "EASILY EXTRACTED WATER METHODS, DEVICES, AND SYSTEMS FOR IDENTIFYING PETROLEUM-ASSOCIATED PARTS OF GEOLOGICAL FORMATIONS," filed Oct. 13, 2019, and to U.S. Provisional Application No. 62/915,012, entitled "EASILY EXTRACTED WATER METHODS, DEVICES, AND SYSTEMS FOR IDENTIFYING PETROLEUM-ASSOCIATED PARTS OF GEOLOGICAL FORMATIONS," filed Oct. 14, 2019. This application claims the benefit of priority to, and incorporates by reference the entirety of, these above-referenced priority applications.

BACKGROUND OF THE INVENTION

Very sophisticated and expensive technology is used by the petroleum industry to locate and evaluate economically viable petroleum deposits in geological formations (oil and gas "pay zones"). Most of this technology is known as logging, and uses data collected by various instruments run into and out of vertical wells after the well has reached total depth (TD), or instruments which run in "real time" during drilling as instruments attached at some distance, usually about 45 feet, behind the drill bit. The science of interpreting such data is called petrophysics.

A main challenge of petrophysics is to recognize, locate, and evaluate pay zones in wells. Much of this depends on values obtained by the well-known and commonly used resistivity log, which measures the ability of electricity to flow through the penetrated formations via the fluids held therein. This method relies on the fact that most subsurface waters are saline to highly saline in nature (as would be understood in the art), and as such they are capable of transmitting electricity. Petroleum, oil, and gas do not conduct electricity. As such, to a first approximation, oil and gas pay zones are recognized as zones of high resistivity. Although well logging has proven very useful and is often a valid method of identifying pay zones, there are situations where well logging can fail to identify pay zones, and there are wells, especially horizontal wells, in which it is usually too expensive to obtain well resistivity logs ("well logs").

For example, well logs are challenged to identify and evaluate pay zones in formations that contain appreciable micro-porosity such as in clay-rich rocks. In these rocks oil and gas can displace water from the larger macro-pores, but not the smaller micro-pores. The rocks in these instances are sufficiently electrically conductive via the water-charged micro-pores as often to be unrecognized as pay zones. Such zones are called by-passed pays and "low visibility pay zones." This phenomenon is widely understood and is the focus of much petrophysics research.

Other rocks may be naturally cemented to the point of being so tight that there is no, or very little, in the way of a continuous water phase in the rock. That is, the rock's pores are not physically interconnected. Such rocks show high resistivity yet lack petroleum, oil, or gas content and thus can be confused as pay zones.

In some geological formations, the associated formation water is fresh water, and, accordingly, can be very non-conductive to electricity. In such rocks, it is difficult to distinguish petroleum from the fresh water using well logs, as all present fluids have very little electrical conductivity.

Most horizontal petroleum wells, which now comprise 90% of the total number of petroleum wells drilled onshore in the continental United States of America, are not logged, as the well logs are prohibitively expensive given the expected low benefit-to-cost ratio of employing a log. In most cases, the geologist evaluating a horizontal well has only a mud log of C1 through C5 hydrocarbon gases and commonly a gamma-ray log generated while drilling. The gamma-ray log is used to identify formation markers to direct the direction of drilling operations (i.e., to "steer" the well). Indicators for the presence of expected petroleum in a typical mud log sometimes coincides with pay zones, but often do not. If mud logs were enough to consistently identify pay zones, most companies would not pay the expense of running much more expensive wire line logs in vertical wells.

Another important challenge related directly to oil production is determining if an area/reservoir is oil- or water-wetting (i.e., determining the wettability characteristics of the reservoir). If the grains that make up a rock are directly coated with a thin layer of water, usually held tightly to the mineral grains by electro-static forces, the rock is "water-wet." However, if the grains in a rock are coated with oil, the rock is "oil-wet."

The water-wetting or oil-wetting properties of materials are not binary or fixed. See, e.g., Abdallah, W., et al., 2007. Fundamentals of Wettability. Schlumberger Oilfield Review, 19(2): 44-61. Most reservoir rocks that are not organic rich source rocks are originally water-wetting. Saturation of these rocks with large proportions of their porosity filled with oil for enough time can turn these originally water-wet reservoirs to oil-wet reservoirs. Once a water-wet reservoir has been transformed into an oil-wet reservoir, it tends to remain oil-wetting even if the oil has been subsequently lost and the pores are again water dominated.

The distinction of water- versus oil-wetness is important for several reasons, including but not limited to the best way to produce oil from an oil accumulation. See, e.g., Abdalla, supra. For instance, during secondary recovery of oil from water-wet rocks, use of water flooding usually results in the production of additional oil, in as much as water-wet rocks imbibe water. However, water flooding usually will not increase the amounts of oil produced from oil-wetting rocks during secondary oil recovery, as oil-wetting rocks imbibe oil and not water.

Currently, methods for determining wettability of materials either take a considerable amount of time, require the use of laboratory equipment, or are subject to several errors or limitations. For example, the Amott-Harvey imbibition test (which measures materials on a scape using a number between +1 (strongly water-wetting) and −1 (strongly oil-wetting)) typically takes at least 10 days to perform and the US Bureau of Mines test requires the use of high-speed centrifugation. See, e.g., Abdalla, supra. Moreover, wettability of materials tested in such methods is often altered due to handling effects before the material reaches the laboratory (e.g., by contact with drilling mud). In some methods, steps of brine-aging followed by oil-aging are performed for at about 40 days, but such methods can also impact wettability results obtained by such methods. See Id.

Wettability is often inferred from other measurements. For example, "strongly water-wet and strongly oil-wet materials display certain characteristic relative-permeability curves." Id. However, "intermediate wetting and mixed-wetting states are not a simple extrapolation between the wettability extremes." Id. Moreover, "predicting the production of oil and water in a transition zone can be difficult when the crude oil has altered formation wettability after migration." Id. Furthermore, for example, "significant anomalies in the gradients of transition zones of homogeneous limestone reservoirs are often found in the Middle East." In fact, "in some of these formations, it is even possible to produce oil from zones in which both the pressure gradient and formation resistivity indicate a water zone." Id.

As discussed in my previous patent applications, I have invented and implemented a multi-aliquot, cryogenic-trap mass spectrometric system for analyzing present day volatile formation fluids ("volatiles") in petroleum drill cuttings and core samples from both vertical and horizontal petroleum wells. The process uses very gentle volatiles extraction, as described in these patent applications, so that all the volatiles contained in the sample can be analyzed. Gentle extraction methods are typically required on modem wells in order to preserve cuttings-associated volatiles for analysis, as most wells today are drilled using PDC (Poly-crystalline Diamond Compact) bits that drill rocks to a much finer degree (akin to how a shaved ice machine makes snow cones). The individual rock particles generated as drill cuttings by PDC bits are relatively very small, usually less than 1 millimeter in diameter, and such a small piece of rock usually also contains many micro-fractures generated during drilling. As such the volatiles in these small pieces of rocks are prone to evacuate the rock during drilling and transport to the surface. Hence, loss of associated substances from such materials is common. These methods are described in my previous patents including U.S. Pat. Nos. 10,494,919; 10,260,336; and 10,190,413). These methods contemplate obtaining one or more aliquots of material from samples such as drill cuttings and analyzing the water content of such aliquots (among other volatiles, such as formic acid and acetic acid); however, the relationship of different types of extractions with the various types of cuttings-associated water as a way of characterizing potential oil pay zones was not contemplated when these patent applications were filed.

As I have described in the above-referenced patents and other patent applications, materials, such as geologic material samples, e.g., petroleum drill cuttings, can often be associated with water, which may be formation water (flowable water in the geological formation from which the drill cuttings are obtained), production water (water used in the petroleum exploration or production process), or water contained in the samples. Water contained in samples (e.g., samples such as drill cuttings) ("sample water") can, in aspects, be characterized based on the ease of extraction of the water as either easily extracted water ("EEW") or release-resistant water ("RRW"). Phrases such as "in material" or "in samples" (or "internal liquid" or "internal water") in this respect are used to mean both liquid, typically water, actually contained in the solid material of the sample (e.g., in micro-fissures of the sample) as well as water bound to or otherwise associated with the surface of the sample (e.g., material-associated water can be protected from evaporation by being coated with oil, or having oil between the water and the air; tar or other solid degraded oil in rocks can be substances other than oil that may facilitate such a protective layer and some or all of such coated water can comprise EEW, RRW, or both). Process water and formation water together can be characterized as "external water," as such water is external to the sample and, at least in part, removable by either exposure to the environment in storage ("aging") or due to application of one or more artificial aging methods.

More recently, I filed U.S. Provisional Patent Application No. 62/791,879 (filed Jan. 13, 2019), and later filed related application PCT/US20/13261 on Jan. 12, 2020 (the "'261 application"), which are directed to the release and analysis of release-resistant water from materials such as drill cuttings. The methods disclosed in the '261 application generally comprise (a) isolating a sample from the environment, (b) removing extraneous water (comprising (1) formation water, (2) production water (associated with the production process), and (3) easy to extract and remove water (i.e., EEW), (c) applying an extraction force to material capable of causing the remaining release of release-resistant water (RRW) and (d) measuring the amount of RRW released from the sample. Thus, the '261 methods exclude EEW from petroleum well cuttings analysis. Moreover, the methods of the '261 application are directed to correlating RRW with the presence of pay zones, rather than to characterization of the content of materials, such as material wettability.

Significant amounts of formation water unrelated to the wettability status of sample material (e.g., drill cutting(s)) itself can be present in samples associated with petroleum exploration or drilling operations. Beyond existing formation water, process water, e.g., water from drilling muds, can also be present in significant amounts. Further, in addition to formation and process water, such samples are commonly processed prior to analysis, a process which commonly includes washing of samples in water. Yet further, the storage of collection samples in warehouses prior to analysis is common, and such storage conditions frequently comprise high humidity and/or high heat (e.g., warehouses in Oklahoma, USA) would be presumed to contribute to the water content of such samples. Accordingly, it has been held that the use of water indicators as a measure of wettability status of samples associated with petroleum exploration or drilling operations has far too many interfering factors to be a useful and reliable determinant.

Principles of Construction & Abbreviations

Any heading(s) and sub-heading(s) provided herein (e.g., "Principles of Construction") are used for convenience only and should not be construed as limiting the invention in any way.

The use of the terms "a" and "an" and "the" and similar referents in the context of describing the invention are to be construed to cover both the singular and the plural, unless otherwise indicated herein or clearly contradicted by context. Inclusion of "(s)" after an element indicates that 1 or more of such an element is present, performed, and the like. E.g., a composition comprising "X(s)" and comprising "Y(s)" means a composition having one or more Xs collectively or individually comprising one or more Ys.

The recitation of ranges of values in this document is intended to serve as a convenient shorthand method of referring individually to each separate value falling within the range within an order of magnitude of the endpoints of the range. For example, a recited range of 1-2 should be interpreted as disclosing 1.0, 1.1, 1.2, 1.3, 1.4, 1.5, 1.6, 1.7, 1.8, 1.9, and 2.0 and a recited range of 10-20 is to be interpreted as providing support for 10, 11, 12, 13, . . . 19, and 20). All recited ranges provided herein include the end points of the provided range, regardless of how the range is described, unless the exclusion of such endpoints is clearly stated or clearly indicated, regardless of the terminology used to describe the range. For example, a range between 1 and 5 will include 1 and 5 in addition to 2, 3, and 4 (and all numbers between such number within an order of magnitude of such endpoints, such as 1.1 and 4.9).

In some cases, terms of approximation, such as "about" are used in connection with values or ranges, as a convenient way of describing a number of suitable values or where it may be difficult to precisely measure a value or limit an aspect of the invention to a particular point. Unless otherwise stated, all exact values provided herein are representative of corresponding approximate values and vice versa (e.g., all exact exemplary values provided with respect to a particular factor or measurement can be considered to also provide a corresponding approximate measurement, modified by "about," where appropriate—e.g., disclosure of "about 10" is to be understood as also providing support for 10 exactly). Ranges that are described with one or more approximate numbers should be interpreted as indicating that all endpoints and other relevant values encompassed by the range may be similarly described, regardless of any different presentations included in this disclosure (e.g., "about 10-20" should be interpreted in the same manner as "about 10- about 20"). The scope of any approximate values will depend on the context of the element at issue and the understanding of those skilled in the art (e.g., as reflected in relevant publications in the art reflecting prevailing views of ordinarily skilled persons). In the absence of typical guidance in the art, through relevant teachings or examples, the term "about" should be understood as meaning +/−10% of the indicated value(s). Other terms of approximation, such as "approximately," are to be similarly interpreted.

Use of the term "or" herein is not meant to imply that alternatives are mutually exclusive unless clearly stated or clearly contradicted by context. Thus, in this disclosure, the use of "or" means "and/or" unless expressly stated or understood by one skilled in the art. The occasional explicit use of "and/or" herein has no effect on the interpretation of "or."

All methods described herein can be performed in any suitable order unless otherwise indicated herein or otherwise clearly contradicted by context or plausibility. Unless otherwise explicitly stated or clearly contradicted by context, any combination of the various elements, steps, components, and/or features of the aspects of the invention described herein, and all possible variations thereof, is to be considered encompassed by the invention. Numerous examples and aspects are provided here to exemplify and clarify the invention. No example, aspect, or combination or pattern thereof is intended to pose a limitation on the scope of the invention. In general, aspects of the invention should not be limited to any particular exemplary processes, compositions, or methodologies. All methods described herein can be performed in any suitable order unless otherwise indicated herein or otherwise clearly contradicted by context or plausibility. Unless clearly indicated or contradicted by context or plausibility, the elements of a described composition, device, or method can be combined in any suitable manner and by any suitable method and any combination of the various elements, steps, components, or features or variations thereof are aspects of the invention.

No part of this specification should be construed as indicating any element or step is essential to the practice of the invention unless as much is explicitly stated. Unless expressly otherwise indicated, description of terms known in the art is for exemplifying versions or embodiments only and not intended to limit the scope of any aspect of the invention. Unless defined otherwise, technical and scientific terms used herein have the same meanings as commonly understood by a person of ordinary skill in the art and implicitly comprise the broadest interpretation based on such usage as well as any narrower interpretation(s) based on specific descriptions provided. In general, any methods and materials similar or equivalent to those described can be used in the practice or testing of embodiments of the invention, methods, devices, and materials described herein.

Unless clearly indicated, the scope of any aspect or embodiment of the invention is not limited to any specific processes, compositions, or methodologies described, as these can vary. The terminology used in the description is for the purpose of describing specific versions or embodiments only; and is not intended to limit the scope of the invention. Unless defined otherwise, all technical and scientific terms used herein have the same meanings as commonly understood by one of ordinary skill in the art and should be interpreted broadly. In general, any methods and materials similar or equivalent to those described herein can be used in the practice or testing of embodiments of the invention, the methods, devices, and materials described herein.

Although this document provides explicit support for "means-plus-function" style interpretation of certain elements, no claim associated with this disclosure should be given a "means-plus-function" construction unless such intent is clearly indicated by use of the terms "means for" or "step for." In particular, the use of the terms "configured to" or "adapted to" are not intended to suggest a "means-plus-function" interpretation, but, rather, typically are used to indicate that the component, composition, device, or other relevant element of this disclosure has been configured to, designed to, selected to, or adapted to achieve a certain performance, characteristic, property, or the like using the principles described herein and/or that are generally known in the art.

Use of an element or component in the singular is to be understood as also providing simultaneous disclosure and support for a plurality of the element or component, if supported or otherwise understood to be possible. For example, the reference to a "washing step" can also mean the application of two, three, four or more repeated washing steps, rather than just a single washing step. The converse also will be understood by those of ordinary skill in the art in reading this disclosure. In other words, the singular is intended to convey the plural and vice versa herein, unless otherwise stated or clearly contradicted by context.

The description herein of any aspect or embodiment of the invention using terms such as "comprising" with reference to an element, composition, or set of compositions or elements should be interpreted, whether explicitly stated or not, as simultaneously providing support for a similar aspect or embodiment of the invention that "consists of," "predominately comprises" (is detectably greater than 50% composed of), and "substantially consists of" (is at least about 95% composed of) that particular element, unless otherwise stated or clearly contradicted by context (i.e., a composition described herein as comprising a particular element should be understood as also describing a composition consisting of that element, substantially comprising that element, predominately comprising that element, and substantially consisting of that element, unless otherwise stated or clearly contradicted by context). Terms such as "including," "containing," and "having" should otherwise be interpreted openly herein, e.g., as meaning "including, but not limited to," "including, without limitation," or "comprising," unless otherwise clearly contradicted.

"Generally consists of" ("GCO") and similar phrases such as "generally is," "generally are," "generally most," "generally all," "generally," or "generally is composed of" means that ≥75% of the composition, collection, or component is or is made up of the referenced element.

Descriptions provided herein that refer to "substantially all" or "substantially consists" of a composition or collection mean at least about 95% of the referenced composition or collection. According to certain embodiments, use of "substantially all" herein provides similar support for cases in which at least about 98%, at least about 99%, at least about 99.5%, at least about 99.9%, at least about 99.999% or more of the composition or collection is made up of the referenced element.

"Essentially all" of a composition or collection means at least about 98% of a composition or collection is composed or otherwise made up of the referenced element. According to embodiments, the use of essentially all provides simultaneous support for at least about 99%, at least about 99.5%, at least about 99.9%, at least about 99.99%, at least about 99.999% or more of the composition or collection being made up of the referenced element.

Changes to tense or presentation of phrases defined herein (e.g., using "comprises predominately" instead of "predominately comprises") will not modify the meaning of the defined phrase, unless otherwise clearly indicated.

The modifier "DOS" means detectable or significant/detectably or significantly. "Significant" means results that are statistically significant using an appropriate test in the given context (e.g., $p \leq 0.05/0.01$).

All references, including publications, patent applications, and patents, cited herein, including patents and patent applications cited above, are hereby incorporated by reference to the same extent as if each reference were individually and specifically indicated to be incorporated by reference and were set forth in its entirety herein. Accordingly, the reader should review and consider such references in understanding the full content of the disclosure. E.g., unless clearly contradicted by context or explicit statement, the disclosure of such documents relating to formulations, methods of production, and methods of use of compositions and devices can be combined with the teachings provided herein to provide additional useful compositions and applications. However, the reader should understand that the citation and incorporation of patent documents herein is limited to the technical disclosure of such patent documents and does not reflect any view of the validity, patentability, and/or enforceability of such patent documents. Moreover, in the event of any conflict between the disclosure and the teachings of such documents, the content of the disclosure will control with respect to properly understanding the various aspects of the invention. Numerous references have been included in this disclosure to incorporate information available from other sources that illustrate the scope of the invention or aid in putting aspects of it into practice. While efforts have been made to include the most relevant references for such purposes, readers will understand that not every aspect of every cited reference will be applicable to the practice of the invention.

In addition to the other references cited herein, the teachings in my previously filed patent application PCT/US19/49613 (referred to as the '613 PCT) are also incorporated by reference herein, as methods described in this '613 PCT application can readily be combined with the various methods described herein in the analysis of samples, such as cuttings, for the identification of petroleum associated regions. Similarly, the methods disclosed in another of my previously filed patent applications (now published as, e.g., WO 2019/178418) are specifically incorporated by reference as the methods disclosed therein also or alternatively can be combined with the methods described in this disclosure and the other references incorporated herein for the identification and characterization of petroleum-associated regions in geologic formations based on the analysis of samples therefrom.

Select Description of Certain Terms and Concepts

The following description of terms and abbreviations is provided to assist readers of this disclosure in understanding the invention. This disclosure is not intended to limit the scope of any terms ordinarily understood in the art. As such, any description of such terms should be considered to refer to certain aspects and to exemplify the meaning of the referenced term. Additional terms and abbreviations are provided in other parts of this disclosure.

The terms "loosely-associated", "tightly-associated", "easily extracted", "release-resistant", "super-release-resistant", "release resistant removed by physical disruption", "non-extractable", and "combined" are terms utilized to characterize the strength of the associated between a liquid or fluid and a material. Each associated phrase can be utilized to refer to a liquid or a fluid, in nearly all aspects an oil or water, and in most aspects water. "Water" in this respect means any liquid that is at least predominately, generally, or at least substantially composed of water. Accordingly, an aqueous suspension, solution, etc., can fall within the scope of "water" in the aspects of the invention provided herein.

"Loosely-Associated Fluid" ("LAF"), such as "Loosely-Associated Water" ("LAW") (sometimes alternatively called "external liquid," e.g., "external water") means liquid (e.g., water) that is in contact with a material but is subject to removal from the material through short-term physical drying (e.g., blow drying or towel drying) or ordinary storage/aging over a short or mid-term period (e.g., of 3 months or less, such as about a month or less) under typical environmental conditions of temperature and pressure. LAW/external water is generally, substantially, or completely composed of "process water" and "formation water." "Process water" is water associated with the sample which is a product of the production methods used to collect the sample, such as, for example, water that comes from drilling mud used in the drilling operation. "Formation water" is water that a sample is normally associated with in a formation, prior to sample creation. In aspects, some, most, substantially all, or all external water is removable by, e.g., subjecting a material to washing and drying, aging material through storage under conditions in which external water is permitted to evaporate, artificially aging a material through artificial aging methods, or similar or equivalent techniques or combinations of techniques.

"Tightly-associated fluid" (most commonly referred to herein as a "tightly-associated liquid" ("TAF"/"TAL") and "Tightly-associated water" ("TAW") means a fluid or liquid, such as water, tightly associated with a material. A TAL is a liquid associated with a material other than LAL, and as TAL is extractable from a material by methods described herein, can also be characterized as NOT being an NEF. For example, a TAL can be an EEW or RRW (which can further include an SRRW, such as RRW-PD).

In aspects, any composition described herein as a fluid/liquid is primarily, generally only, at least substantially all, or only a liquid at room temperature, at typical environmental temperatures above the freezing point of water, or both.

"Easily Extracted Fluid/Liquid" ("EEF"/"EEL"), such as "Easily Extracted Water" ("EEW") typically means a TAL/TAW that is extractable from a material on application of a vacuum pressure of about 10- about 200 millibars, such as about 10 to about 100 millibars, e.g., about 10- about 80 millibars or about 10- about 60 millibars, for a period of about 5-30 minutes, e.g., about 5-20 minutes, such as about 7.5-15 minutes, such as about 10 minutes. An "EEF/EEL/EEW Extraction Force" ("EEFEF", "EELEF" or "EEWEF") is a force suitable to extract a measurable amount of EEF/EEL or EEW from a material. Typically, an EEFEF/EELEF/EEWEF is a force that results in extraction of EEW that is not significantly different from the amount of EEF/EEL/EEW extracted from a material upon application of a pressure described in this paragraph for a suitable period of time to release a measurable amount of EEF/EEL/EEW, such as between about 5-60 minutes, such as about 7.5-30 minutes, e.g., about 8-24 or about 8-16 minutes. An EEF/EEL/EEW can be extracted from a material using less force than that required for removing an RRF/RRL/RRW or and RRF-PD/RRL-PD/RRW-PD. An EEW may be thought of as "readily extractable" and can sometimes be referred to as such. An EEW can generally be removed from the sample with very limited effort or using very simple techniques. For example, if a sample were to be boiled, water simply released as steam would be considered an EEW or a readily extractable water.

"Release Resistant Fluid/Liquid" ("RRF"/"RRL") and "Release Resistant Water" ("RRW") means fluid/liquid or water tightly associated with a material which can be extracted using an "RRF/RRL/RRW Extraction Force" ("RRFEF", "RRLEF" or "RRWEF"). An RRFEF/RRLEF/RRWEF is a force suitable to extract a measurable amount of RRF/RRL/RRW from a material. An RRF/RRL/RRW is a non-readily extracted fluid/liquid/water and cannot be removed from a sample using limited or simple effort as is the case with an EEF/EEL/EEW. Typically, an RRFEF/RRLEF/RRWEF extracts an amount of RRF/RRL/RRW from a material that is not statistically significantly different from the amount of RRF/RRL/RRW extracted on the application of a pressure of about 0.5-5 millibars pressure, such as about 2-3.5 millibars, e.g., 1.5-3 or 1-3 millibars of pressure, for about 10 minutes (e.g., about 7.5-30 minutes, or about 8-20 minutes). An RRF/RRL/RRW is tightly associated liquid/water which can be removed from a material using more force than is necessary to remove an EEF/EEL/EEW. The term RRW is inclusive of the term SRRW, e.g., RRW-PD; however, the specific conditions under which an SRRW (e.g., RRW-PD) can be extracted are further described (e.g., require physical disruption of the material in the case of RRW-PD).

"Super Release Resistant Fluid/Liquid" ("SRRF"/"SRRL") or "Super Release Resistant Water ("SRRW") and "Release Resistant Fluid/Liquid/Water Removed by Physical Disruption" ("RRF-PD", "RRL-PD" or "RRW-PD") is/are a TAL(s), such as water, and further is a RRF/RRL/RRW. Release-resistant fluid/liquid/water (RRF/RRL/RRW) broadly can further be broken down into release-resistant fluid/liquid/water which is only released after applying methods that cause the release of EEF/EEL/EEW and a limited amount of RRF/RRL/RRW. Such a release resistant fluid/liquid/water can be referred to as "super release-resistant fluid/liquid/water" ("SRRF"/"SRRL"/"SRRW"), in that it requires an additional application of force to remove. In certain cases, such a force can be a force causing a physical disruption ("PD"). In such a case, the SRRF/SRRL/SRRW can be referred to as a "release resistant fluid/liquid/water removed by physical disruption" ("RRF-PD"/"RRL-PD"/"RRW-PD"). Other types of additional forces may be applied which release specific fractions of, or all of, an SRRW. An SRRW is a TAL that is associated with a material but not extractable from the material in amounts of more than about 5%, typically not more than 2% or not more than 1%, with application of a vacuum with a pressure of about 0.1 millibar or less, such as about 0.01 millibar or less, such as about 0.001 millibar or less, for a period of time such as about 5 minutes or more, about 10 minutes or more, or about 15 minutes or more without application of an additional extracting-promoting force or additional extracting-promoting conditions such as a force causing physical disruption of the sample. For sake of clarity, RRW can be released from a material without physical disruption, or without the addition of an SRRW-releasing force ("SRRWRF"). The term RRW can include water extracted upon, e.g., application of an SRRWRF such as a force causing physical disruption of a material if such conditions are applied to the material. Thus, SRRWs, such as, e.g., specifically RRW-PD, are a subset of RRW that is not released without physical disruption of the material or application of other correspondingly effective or more effective force, condition, or both. In some aspects, application of an SRRWEF resulting in the release of an SRRW (e.g., physical modification of a sample release of RRW-PD) and the resulting analysis incorporating the SRRW (e.g., RRW-PD) fraction resulting therefrom, (e.g., comparison of the TAL from non-physically disrupted samples and physically disrupted samples), allows for the identification of material characteristics that would otherwise be non-observable. In some cases, an SRRF/SRRL/SRRW, e.g., an RRF-PD/RRL-PD/RRW-PD, can in some aspects include a limited amount of "inclusion fluids" (such as fluids in geologic sample fluid inclusions), water in crystalline mineral forms in material, or both. However, such inclusion fluid in material utilized in the methods described herein typically is present in such a low amount as to be insignificant to the analyses and associated characterizations of materials. Inclusion fluid typically should not make a significant contribution to an analysis of any TAL. In aspects, an RRW can be a water contained on a sample due to an exterior coating of oil or other material such as a tar which protects water in oil saturated rocks from evaporating. In some aspects, such a water could be a RRW or SRRW.

"Non-Extractable Fluid/Liquid" ("NEF"/"NEL") or "Non-Extractable Water" ("NEW") is a fluid or is water that is not EEF/EEL/EEW, RRF/RRL/RRW, or RRF-PD/RRL-PD/RRW-PD. Water bound in crystalline material, for example, is typically NEL. In aspects, no significant or no detectable amount of NEF/NEL is extracted or otherwise analyzed.

"Combined water" ("CW") (sometimes called "Sum Water" or "Total Water") is a measure reflecting an approximate sum of EEW and RRW in a material or the sum of EEW and RRW analyzed in a method (e.g., the sum of at least generally all, substantially all, or essentially all EEW and RRW extracted, captured, and analyzed in the practice of a method). Discussion of combined water is dependent on the method applied to obtain the RRW, and, accordingly, can include SRRW if an SRRWEF has been applied.

"Gentle Vacuum" or "Gentle Vacuum Condition" means application of a vacuum pressure of about 0.5- about 200 millibars to a material, such as about 1 to about 200 millibars, e.g., about 1.5- about 150 millibars, or about 2 to about 100 millibars.

Wettability

In aspects of the invention, a determination of wettability of a material is made. The concept of wettability, discussed in the Background of the Invention, supra, is known in the art.

Because of the relative permanence of oil wetting, documenting that a water filled reservoir is oil wetting is therefore good evidence that those rocks once had high oil saturations and were probably part of an oil accumulation in the past.

The documentation of oil versus water wetness is usually determined from the testing of a slabbed core. A drop of water on a water wet rock will spread over the surface of that rock and will imbibe into that rock. A drop of water on an oil wet rock will bead up, and the contact angle between the droplet and the flat surface is the standard measure of the degree of oil versus water wetting of the cored reservoir.

There are also newer proposed log methods to determine wettability that require running a number of expensive logging tools and then a fairly complicated mathematical treatment of those data.

The identification of a "dry hole" as having once been a pay zone in the past can be important information that justifies continued exploration in an area, inasmuch as such a finding demonstrates that the area under exploration is part of a petroleum system that has the necessary components to host an economic oil deposit. Hence, the identification that a water saturated reservoir drilled today is an emptied oil reservoir that lost its oil in the past, through performance of methods of the invention, can evidence that continued exploration in that area is likely to result in a finding of petroleum in the area.

Geologic Materials and Geologic Areas

Methods of the invention can be applied with any suitable material/substance. Often methods are performed with one or more samples, typically several samples, of a material/substance, obtained from one or more areas of a substance.

In aspects, the "substance" of the method is a substance that defines/fills a geologic area. In aspects, several samples of a substance can be obtained from any suitable number of locations. E.g., in aspects, samples are obtained from at least about 10 separate locations in an area/site, e.g., an area containing multiple sites, a formation, reservoir, or from any other suitable geologic unit, or from some combination thereof.

A "formation" is typically understood in the art to mean an identified area of strata having similar lithology. In some cases, a formation also may be defined by other characteristics, such as biostratigraphic characteristics, chemostratigraphic characteristics, or both, and sometimes such characterizations of a formation are used interchangeably (e.g., the Meramec Shale Formation is often referred to as the Mississippian Formation, reflecting the period in which the rock was deposited). Typically, a formation is a series of strata/beds that is distinct from other beds above and below and is thick enough to be shown on the geological maps that are widely used within the area in question. Formations dominated by a rock typically include the dominant rock in the formation's name (e.g., the "Woodford Shale Formation" found in several parts of Oklahoma). However, formations in some cases can contain a variety of related or interlayered rock types, such as the Summerville Formation of Utah, which consists of thin alternating beds of shale, siltstone, and sandstone. Often in the art and this disclosure the term "Formation" (or "formation") is used to refer to a portion of a geologic area (e.g., a site) associated with that Formation, rather than the entire Formation. E.g., rocks of a Formation in a site can have certain characteristics and methods of the invention can reveal characteristics of rocks of such a Formation in a site or other area.

Formations can be divided into sub-formations or "members" based on such characteristics. Formations also can be grouped together into "groups." Both "groups" and "members" are commonly used terms of art. For example, a formation that includes both shale and sandstone might be divided into members, each of which is either shale or sandstone. In some areas, where more detail is needed, members may even be further divided into beds. A group typically represents a series of rocks deposited within a single basin (or a series of related and adjacent basins) over a geologic period (e.g., a few million to a few tens of millions of years).

Basins are large-scale structural formation of rock strata formed by tectonic warping. The Permian Basin in Texas (comprising Wolfcamp, Cline Shale, Strawn and Atoka formations) is a well-studied example of a basin. Basins can include sub-basins (e.g., the Permian comprises the Delaware Basin, Midland Basin, and Central Basin Platform). Basins can be characterized on the basis of Formations present in the Basin. E.g., the oil rich Wolfcamp Shale Formation is present in all three sub-basins. This fact (and terminology) demonstrates that the line between formations and groups is not always clear and that aspects described here with respect to one implicitly provide support for the other and vice versa.

The term "geologic unit" or "geologic area" (sometimes simply called an "area") is used to refer to any discrete geologic area (a basin, group, formation, member, bed, area, site, or a location within any thereof). Methods of the invention can be applied to a single site or to larger areas comprising several sites, or to even larger areas such as beds, groups, members, formations, or basins, to characterize such a region.

In petroleum production the term "play" is used to indicate a region defined by a group of oil fields (each comprising many wells/sites) that generally share the same set of geological circumstances (e.g., formations present). Oklahoma, for example, has many plays but two notable ones making headlines across the nation are the "SCOOP" (South Central Oklahoma Oil Province) and the "STACK" (Sooner Trend Anadarko Basin Canadian and Kingfisher Counties). The petroleum-rich STACK play is characterized by presence of Oswego, Meramec, Osage, and Woodford formations. Plays can be divided into "regions" or "areas" comprising two or more (often several) sites, potential sites, or both. A typical "site" is a petroleum well (e.g., an actively producing well area, a well under development, or previously producing well such as a "dry hole") or an area of prospective petroleum drilling within an area or play. The term "reservoir" is also used to characterize petroleum-production associated geologic areas. A reservoir is generally understood as an area containing producible amounts of subsurface petroleum oil and/or gas, typically in porous or fractured rock formations, and associated areas such as any overlying or underlying formations (sometimes called caps, beds, and the like). In aspects, methods of the invention are applied to reservoirs, plays, or both, meaning such geologic areas/units. In specific aspects, methods of the invention are applied to a reservoir, e.g., a reservoir within a freshwater petroleum site, and which further may reside in a low visibility play. In further aspects, the inventive methods are applied to drilled oil wells.

SUMMARY OF THE INVENTION

The invention described here provides new methods for determining wettability characteristics, e.g., the water-wetting or oil-wetting properties, of materials through the analysis of tightly-associated liquids/fluids ("TAL/Fs"). Such TAL/Fs can be characterized on the basis of their separation/extractability from materials under selected conditions. The "tight" characterization of the association of such liquids/fluids distinguishes such liquids/fluids/associations from (1) external liquid-material associations, which are easily eliminated and (2) from even closer associations of liquids and materials, e.g., in crystallized water in materials.

In some respects, the wettability characteristics as determined by the methods described herein can provide insight into the character of a larger substance from which an analyzed sample of material may have originated. For example, the wettability characteristics of petroleum drill cuttings collected from a geological area as identified by the methods described herein can indicate a material is oil-wet material, such an oil-wet nature indicating a higher probability of, or a higher correlation with, or both, the present-day or past existence of petroleum, aiding in the identification of a petroleum reservoir in the sampled geological location or within an associated/larger geographical/geological area.

In some respects, the invention described here provides methods for characterizing the wettability of man-made materials, biologic materials, or both. In aspects, such materials are bone or device materials.

In aspects, the disclosure herein provides methods of using the analysis of one or more TALs alone, such as an EEW, to provide a useful characterization of the wettability of a material. In other aspects, the analysis discloses utilizes the relationship between two or more TALs, or combinations of TALs (e.g., sums or ratios of individually measured TALs or combinations of TALs).

In aspects, the invention provides methods in which a still even further level of tightly associated liquid, such as water, than that described by my previous work, is extracted from materials only after applying methods that cause the release of EEW and a limited amount of RRW. In the case of such water, the fraction of RRW released can be referred to as a "super release-resistant water" or "SRRW". SRRW is a previously unidentified important fraction of an RRW, in that when identified independently, can be used in comparison with other values obtained through these inventive methods to identify wettability characteristics which were unidentifiable using previously described techniques.

In some respects, the invention described herein is a method whereby the wettability characteristics of a material are determined (a) based directly upon any two or more of EEW; RRW (in aspects including one or more SRRWs); sum of EEW and RRW (in aspects including one or more SRRWs); and an SRRW such as RRW-PD; or (b) based upon the relationship of any two or more of EEW; RRW (in aspects including one or more SRRWs); sum of EEW and RRW (in aspects including one or more SRRWs); an SRRW such as RRW-PD; sum of EEW, RRW, in aspects including one or more SRRWs); or any combination of (a) and (b).

In aspects, most, generally all, substantially all, or all of the TAL of a material analyzed by the methods described herein can be extracted by application of gentle vacuum forces (releasing EEF/EEL/EEW and at least a portion of the RRF/RRL/RRW), optionally applied in combination with some physical disruption (releasing RRF-PD/RRL-PD/RRW-PD) of the material or application of a release-enhancing composition, such as one or more material-associated liquid (MAL)—e.g., tightly-associated liquid (TAL)-release promoting substances such as surfactants. The invention herein describes methods wherein analysis of the TAL of a material collected without physically disrupting the material is utilized to characterize the material; however, the invention herein also discloses methods whereby the use of physical disruption of a material, such as disruption accomplished by mechanical force directed upon a material, releases liquid not released as an EEW or RRW without disruption, and provides insight into material characteristics not otherwise available without performance of such a physical disruption of the material.

The invention described herein further provides methods of assessing the characteristics of a material quickly and inexpensively comprising the application of a fast-acting TAL-releasing substance (FATALRS). Such methods can be capable of characterizing a material, such as the oil-containing nature of a material, within a short period of time, e.g., within 1 hour. The invention also provides methods of screening for such FATALRS to identify FATALRS which may be useful in such a method.

In aspects, methods of the invention can be applied to natural materials, such as rock from a petroleum exploration operation, e.g., the use of drill cuttings. Surprisingly, the inventive methods described for the first time herein can be applied to materials other than samples obtained from geologic areas (such as petroleum drill cuttings). E.g., in aspects, the invention herein describes determining the wettability characteristics of artificial or man-made materials such as materials used in pharmacological products, electrical products, construction materials, or medical/biomedical devices. In other aspects, methods of the invention are applied to biological material(s) (e.g., tissue(s), bone(s), or combinations thereof).

The TALs used in the property determination of either natural or artificial materials collected and measured by the methods described herein, surprisingly, are not limited to either the rock-associated volatiles (RAV(s)) or release resistant water (RRW) described in my earlier patent applications, and are in fact inclusive of EEW and also or alternatively specifically identify SRRW, e.g., RRW-PD. In one aspect, TALs extracted from materials and used in such methods include easily extracted water (EEW), either alone or in combination with RRW. This is surprising in that, as noted above, I and others in the art have long previously believed that EEW should be treated as a waste product to be discarded, rather than an analytical input.

In aspects, selected condition-extracted TALs ("SC-ETALs") (e.g., EEW, RRW, or both) are used in the analyzing materials, such as materials that have been recently associated with petroleum materials (indicating possible presence or a higher probability of the presence of nearby petroleum products). In one exemplary aspect, the relationship between EEW and either (a) RRW or (b) combined water, associated with a material(s), is used to characterize materials in terms of wettability. In aspects, TAL data further can be used to identify pay zones. In aspects, TAL(s) is/are extracted with the addition of a release-enhancing composition, force, conditions, or combination thereof. In aspects, methods of the invention identify likely pay zone associated areas even in areas where well logging fails to identify a pay zone.

In one aspect, further analysis comprising use of SRRW such as RRW-PD can be used to identify and distinguish material wettability characteristics and can, in aspects, identify the presence of likely oil and gas pay zone(s) in a geological area, which may not otherwise be identifiable without physical disruption of the test material.

In certain respects, the invention described herein provides a method of identifying the wettability characteristics of a material comprising (a) providing an analyzable amount of a material; and (b) subjecting the material to one or more environments/compositions selected from the group environments comprising (i) an environment characterizable as being under vacuum pressure; (ii) an environment characterizable as being saline; (iii) an environment/composition characterizable as comprising a release promoting-effective amount of a surfactant, of a character and amount sufficient to cause the release of a detectable or significant amount of material-associated water; (c) capturing and measuring the amount of the extracted material-associated water released from the material; and (d) characterizing the wettability properties of the material based on the measurement extracted material-associated water. In some specific aspects, the environment to which a material is exposed in conducting the method is one or more vacuum pressure conditions of between about 1 millibar and about 100 millibars ("gentle/Gentle vacuum pressures") or in aspects between about 10 and about 100 millibars, for one or more periods to cause the release of a detectable amount of material-associated water. In certain facets, the material is petroleum drill cuttings.

In certain aspects, the invention is a method of characterizing a material comprising (a) providing an analyzable amount of a material; (b) measuring the amount of easily extracted water in the material; and (c) characterizing the material based on the amount of easily extracted water (EEW) in the material.

In some facets, the invention is a method of characterizing a material comprising (a) providing an analyzable amount of an artificial material; (b) measuring the amount of material-associated water in the material to assess the wettability characteristics of the material;

In aspects, the methods of the invention described above can be applied to a single sample or also or alternatively may be applied to a plurality of samples. In aspects, some or most sample(s) can be samples that are co-located sample(s). In some aspects, such sample(s) can be representative of a larger substance from which they were collected. In aspects, such samples can be treated using different treatment methods upon collection, such as for example petroleum drill cutting samples may be sealed at the well using existing methods or novel methods as described herein upon collection or allowed to be exposed to a natural or artificial environment after collection. In aspects, the methods described above can comprise the analysis of multiple aliquots of liquid, e.g., water, extracted under different conditions and the results of the individual aliquots used directly or combined and compared in various ways to characterize the material from which they were extracted. In aspects, the material utilized in the inventive methods can be physically disrupted so as to release additional liquid, e.g., water, which provides further insight into the wettability characteristics of the sample(s) which would otherwise be unknown.

In aspects, the methods of the invention can comprise a trap which selectively captures amounts of released/extracted liquid ("aliquots"), and in certain facets samples are initially subjected to cryogenic mass spectrometry volatiles analysis ("CMSVA") prior to performing the measurement comprised within the methods described herein (such methods are described in detail in my prior patents).

In certain facets, the analysis of TAL in a material comprises the use of Fourier Transform-Infrared Spectroscopy (FTIR) (e.g., to measure or approximately measure total water).

In aspects, the methods comprise use of capacitance manometry to measure the material-associated liquid (MAL/TAL) released by the methods. In aspects, a capacitance manometer is capable of indirectly measuring water by virtue of our findings in prior mass spectrometry work that it is likely that at least 95%, at least 96%, at least 97%, at least 98%, at least 99%, such as 99.5% or even at least 99% of the pressure caused by the evaporation of condensable volatiles from some material (e.g., rock material), is caused by water release.

In certain aspects, a relatively short time period between the time of sample collection and the time of analysis provides the opportunity for the results of the application of the method to be used in real-time or relatively real-time decision making (e.g., results can be available within 48, 24, or even 12 hours or less from the time of sample collection).

The invention described herein further provides methods of assessing the characteristics comprising the application of a fast-acting TAL-releasing substance (FATALRS). Such methods can be capable of characterizing a material within a short period of time.

According to some aspects, the invention described here provides a method of assessing the characteristics of a material comprising providing an analyzable amount of the material and applying a fast-acting tightly-associated liquid (TAL)-releasing substance (FATALRS) to the material, wherein the FATALRS is capable of releasing a visually detectable amount of TAL from the material within a period of less than about 2 hours, e.g., less than about 1 hour, and in aspects less than about 30 minutes. In one specific aspect, such a FATALRS is or comprises an effective amount of one or more polyphenolic compounds, the material assessed by the method is sample(s) of petroleum drill cuttings, and the TAL is an oil. An "oil" in this respect can mean any type of oil that is a MAL. An "oil" in the context of a geological material (e.g., a cutting) typically means a petroleum-associated oil composition comprising petroleum-associated hydrocarbons.

In aspects, the invention provides a method of screening to identify effective one or more effective FATALRs, effective amounts of a FATALR, or both. An "effective amount" in this respect is an amount of a FATALRS or a component thereof that causes a significant and practically measurable (typically visually recognizable) release of a TAL from a material upon application within a relatively short amount of time, such as the times described herein (e.g., within about 12, 6, 4, 3, or 2 hours from application).

According to one specific aspect, the invention is a method of quickly determining the oil wetting nature of a material comprising (a) providing a panel of substances comprising (i) one or more polyphenolic compounds, each polyphenolic compounds varying from any other polyphenolic compound in at least one chemical property; (ii) one or more surfactants, each surfactant varying from any other surfactant in at least one chemical property; (iii) one or more saline solutions, each saline solution varying from any other saline solution in at least one chemical property (e.g., percent salinity or type of salt); or (iv) a combination of any two or more of (i)-(iii); (b) placing the material/sample into each of the substances of the panel of (a); and (c) evaluating the response of the material/sample to the substance by (i) visually inspecting the effect of the substance on the material, e.g., visually inspecting the release of oil from the material; or (ii) measuring one or more changes in the substances after receiving the material by an automated method capable of detecting one or more changes to the substances after receiving the material.

In one facet, the invention provides a method of identifying the oil- versus water-wetting characteristic of a material without changing the physical structure of the material being analyzed, comprising subjecting the material to (a) one or more vacuum conditions; (b) one or more temperature conditions; (c) one or more immediate environmental conditions (e.g., conditions having a polyphenolic, saline or surfactant nature); or (d) any combination of one or more of (a)-(c), wherein modifying one or more of (a)-(d) changes, e.g., significantly changes, the amount of oil, volatile hydrocarbons, water, or any combination thereof released from the material, and further wherein changes in the amount of oil, volatile hydrocarbons, water, or any combination thereof released from the material by varying any one or more of (a)-(d) is representative of the oil- or water-wetting characteristic of a material.

In one specific aspect, the invention provides a method of identifying the oil-wetting nature of a sample of material obtained from a geological area to identify one or more oil-wet locations within the geological area comprising comparing the results of extracted material-associated liquid (e.g., TAL) from samples collected and processed in one manner versus samples collected and/or processed in a second manner, different from the first. In one aspect, such samples can be the same samples, the first manner of processing being followed by a first analysis and the second manner of processing being followed by a second analysis. In an alternative aspect, such samples can be different sets of samples collected from the same location(s). In a specific embodiment, the invention provides a method comprising (a) obtaining from two or more locations within a geologic formation (i) two sets of samples, each set having samples collected from the same locations within the geologic formation; one set of samples having been hermetically sealed upon collection, and one set not sealed at the well upon collection, or (ii) a single set of samples hermetically sealed upon collection which is (1) later divided into two sets of samples such that one set is identifiable as hermetically sealed and one set is identified as unsealed, or (2) first analyzed as a hermetically sealed sample then reanalyzed after further sample preparation; (b) subjecting the second set of samples identified as unsealed or alternatively having first been analyzed as a sealed sample to aging through storage under conditions in which some, most, substantially all, or all of the external water is permitted to evaporate ("lab-aged"); (c) measuring two or more volatile hydrocarbons in sealed samples extracted under vacuum conditions by any process capable of applying such conditions and providing such a total oil indication oil response, if present, without mechanically disrupting the physical structure of the samples; (d) subjecting the unsealed, lab-aged samples, or alternatively the sealed samples having completed step (c) to physical disruption (e.g., crushing), and measuring the same two or more volatile hydrocarbons extracted under vacuum conditions; (e) collecting a total oil indication (oil response), if present, from each sample analyzed in (c) and (d); and (f) identifying variations in the responses between the two sample sets of (c) and (d) as measured by (e), wherein lab-aged sample(s) having a higher total volatile hydrocarbon (oil response) result than that measured in a sealed sample obtained from the same location is indicative of oil wetting rock at that geological location from which samples were collected.

In some aspects, the invention provides devices comprising one or more components specifically adapted for performing methods described above. In one aspect, such devices comprise a capacitance manometer and a vacuum and sample physical disruption equipment for releasing SRRW such as RRW-PD. In aspects, such devices comprise computer executable systems that analyze EEW, RRW, an SRRW, and/or any or all thereof, and further optionally other measurements, such as oil-associated volatiles, and such systems further optionally comprise non-transient computer readable media comprising computer programmable and executable instructions and processors for performing mathematical calculations using two or more such measurements, or comparing two or more of such measurements or calculations for aiding in the performance of any one of the methods described herein (e.g., assessing wettability or finding pay zones).

When applied to certain geologically-related material, the water analytical aspects of this invention allow the determination of whether a geological area, e.g., an oil reservoir, comprises rock which is oil- versus water-wet based on the analyses of drill cuttings. The determination of oil versus water wetness from drill cuttings can help determine present day pay zones, as well as determine if a reservoir that is not a pay zone today was a pay zone in the past. In aspects, methods of the invention comprise making a determination of water or oil wettability of one or more parts of a geologic area, such as an oil well, and directing methods of oil extraction, drilling, or both, based on such a determination.

Significant focus in this application is on the use of identifying petroleum drill cuttings as either oil or water wet, such identification having utility for mapping present and past pay zones in petroleum-related exploration. However, other applications of this invention to any other venture, geologically-related (e.g., such as how to best complete a water- or oil-wet reservoir for optimum oil production, when such an identification is made using this invention) or non-geologically related (e.g., such as the suitability of a particular material for a manufactured product based on its wettability characteristics which for example may be applicable to pharmaceutical, electronic, or medical technologies, are also included in the scope of this disclosure.

Additional facets of the above-described exemplary aspects and these other additional aspects and embodiments will be described in further detail in the Detailed Description of the Invention, which follows below.

BRIEF DESCRIPTION OF THE DRAWINGS/FIGURES

The figures provided in this disclosure are described in detail in the Detailed Description of the Invention. A brief description of the incorporated figures is provided here for ease of reference.

FIG. 5 illustrates the mole fraction of water released by multiple aliquots across various well depths of the well described in association with FIG. 1 and FIG. 3.

FIG. 6 illustrates the mole fraction of water released by multiple aliquots across various well depths of the well described in association with FIG. 2 and FIG. 4.

FIG. 7 illustrates the same curve of FIG. 5 with an indication of oil production zones (by shading), the shading identifying areas which are oil-wet.

FIG. 7B illustrates an additional alternate curve for presenting the water release data shown in FIGS. 7 and 7A (FIG. 7B is provided as a panel with FIG. 8B to facilitate comparison).

FIG. 7D illustrates an additional alternate curve for presenting the water release data shown in FIGS. 8, 8A, and 8B (FIG. 7D is provided as a panel with FIG. 8D to facilitate comparison).

FIG. 8 illustrates the same curve of FIG. 6 with an indication of oil production zones (by shading), the shading also identifying oil-wet areas.

FIG. 8B illustrates an additional alternate curve for presenting the water release data shown in FIGS. 7, 7A, and 7B (FIG. 8B is provided as a panel with FIG. 7B to facilitate comparison).

FIG. 8D illustrates an additional alternate curve for presenting the water release data shown in FIGS. 8, 8A, and 8B (FIG. 8D is provided as a panel with FIG. 7D to facilitate comparison).

FIG. 11 illustrates the same plot as FIG. 9 but with potential oil pay zones identified by shading (shading identifying areas which are oil-wet).

FIG. 11A illustrates the same plot as FIG. 11, showing the mole fractions of Aliquot 1 water and Aliquot 2 water each relative to the sum of Aliquot 1 water plus Aliquot 2 water.

FIG. 11B illustrates an alternative method of viewing the data shown in FIGS. 11A, using the ratio of Aliquot 1 water to Aliquot 2 water.

FIG. 12 illustrates the same plot as FIG. 10, but with potential oil pay zones indicated by shading (shading identifying oil-wet areas).

FIG. 12A illustrates the mole fraction Aliquot 1 water which equals Aliquot 1 water divided by the sum of Aliquot 1 water plus Aliquot 2 water.

FIG. 12B illustrates an alternative method of viewing the data, using the ratio of Aliquot 1 water to Aliquot 2 water.

FIG. 17 illustrates the same property logs shown in FIG. 15 with added pay zone indication (by shading).

FIG. 18 illustrates the same property logs shown in FIG. 16 with added pay zone indication (by shading).

FIG. 23 shows the mole fraction water curves from a lateral drilled well (well 3), which was drilled from ("off of") the vertical well shown in FIGS. 13-22.

FIG. 24 shows the combined water curves from a laterally drilled well (well 3) drilled off of the vertical well shown in FIGS. 13-22 (well 3).

FIG. 27A illustrates the mole fraction of Aliquot 1 water which is the ratio of Aliquot 1 water to the sum of Aliquot 1 water plus Aliquot 2 water.

FIG. 27B illustrates the ratio of Aliquot 1 water to Aliquot 2 water.

FIG. 28A illustrates the same curve as FIG. 28, showing the mole fractions of both Aliquot 1 and Aliquot 2 water and showing 3 shaded oil wetting pay zones having values about or more than 0.8.

FIG. 28B illustrates the same curve as FIG. 28, showing the mole fractions of both Aliquot 1 and Aliquot 2 water and showing 3 shaded oil wetting pay zones having values about or more than 0.8.

Figure 32A:
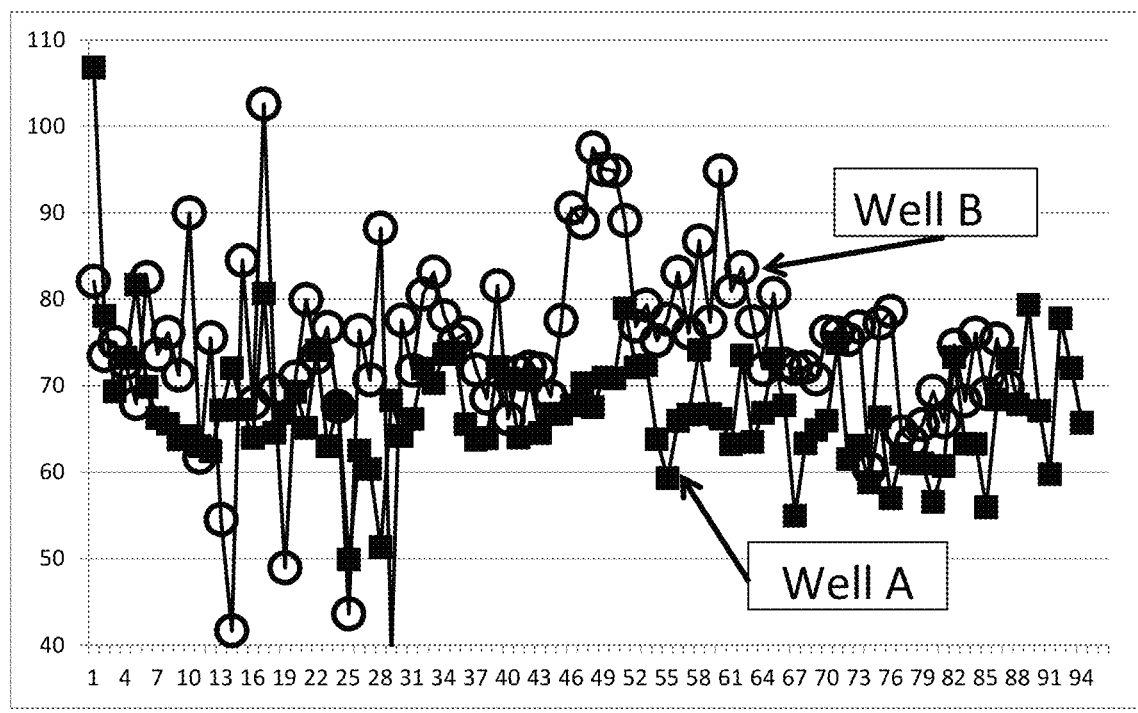
Figure 32B:
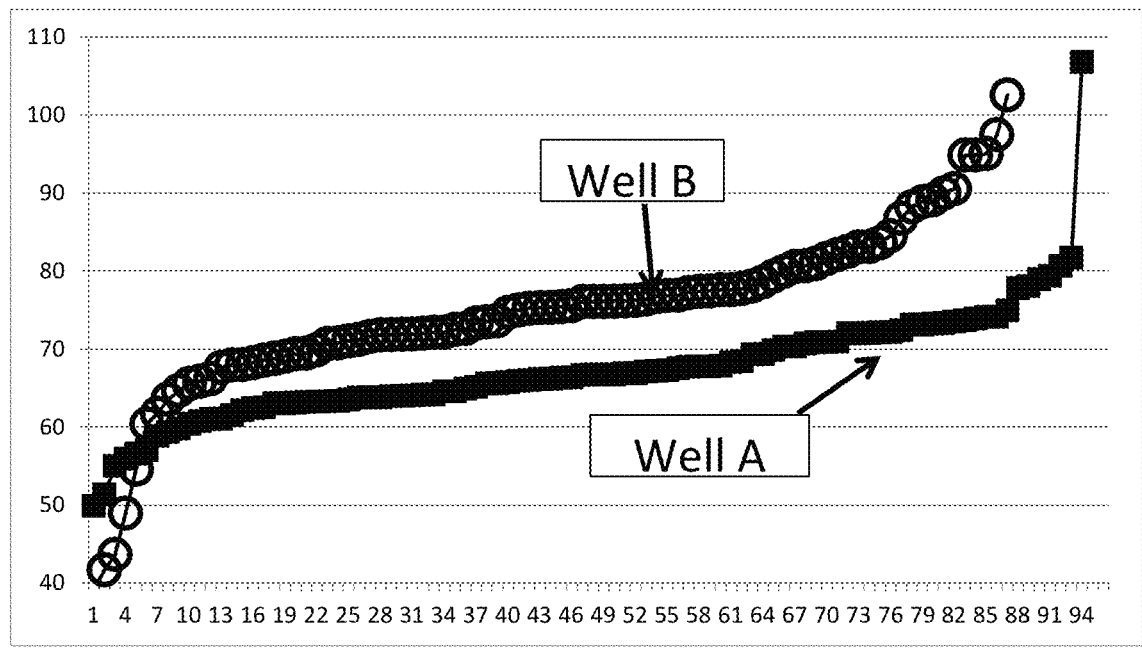

FIGS. 32A and 32B illustrate Aliquot 2 data from 2 horizontal wells analyzed as a blind test for identifying higher vs. lower producing wells. FIG. 32A provides the Aliquot 2 water data along the laterals from heel to toe. FIG. 32B provides the same data where the Aliquot 2 water data is sorted by response.

Figure 33:
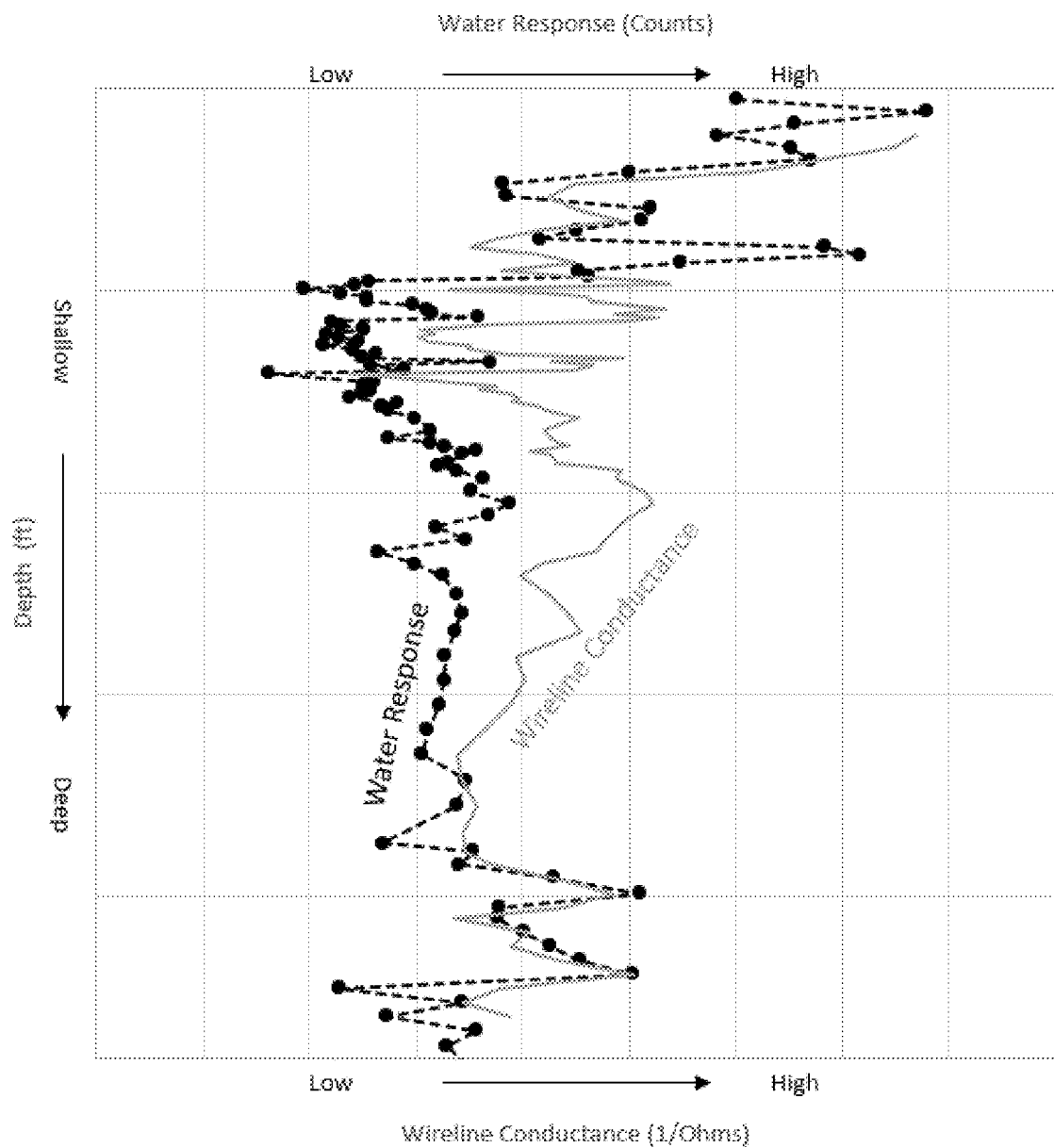

FIG. 33 illustrates combined water data analyzed for a well versus the inverse of the wireline resistivity log of the well, illustrating their strong correlation.

Figure 35:
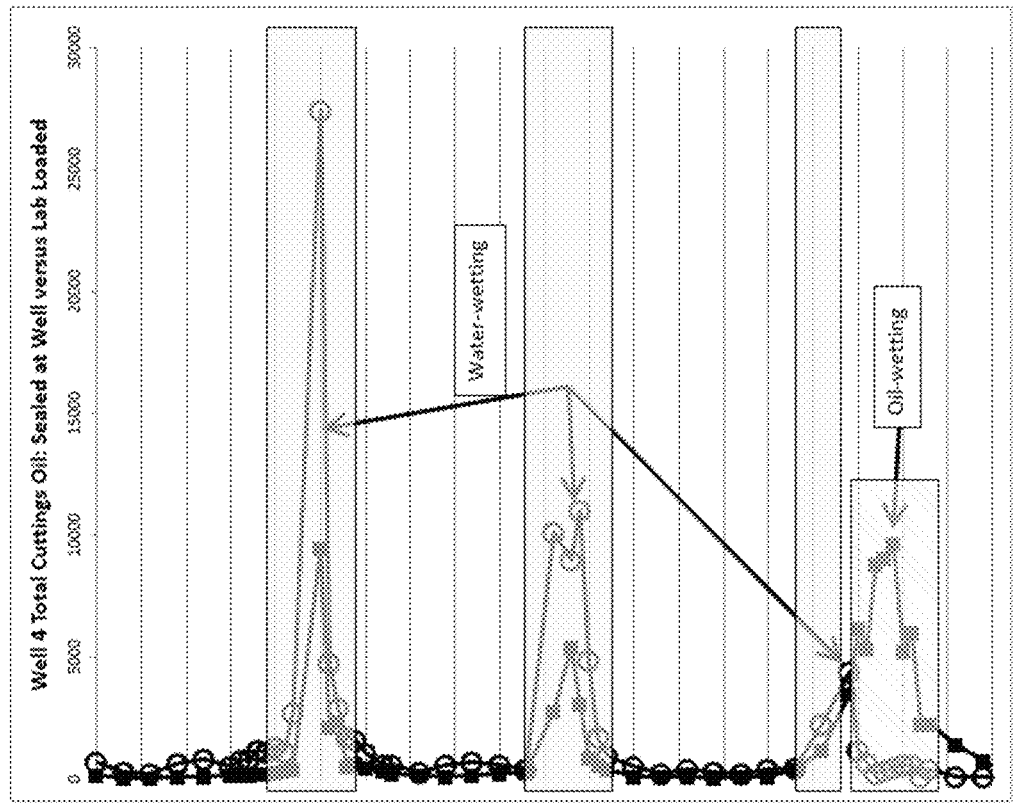
Figure 34:
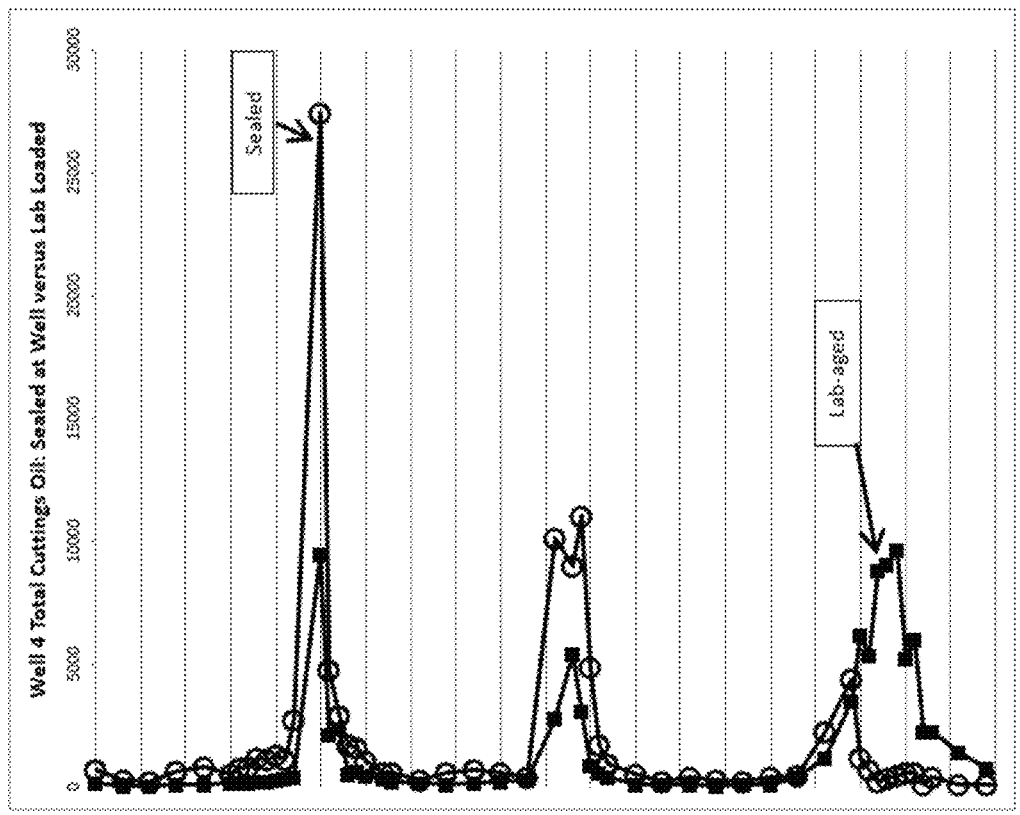

FIGS. 34 and 35 illustrate the identification of a location within a well comprising oil-wetting rock through the comparison of the oil response of sealed at the well versus lab-aged and physically disrupted (crushed) samples across the depth of the well, demonstrating the ability to isolate SRRW, such as RRW-PD, from materials.

DETAILED DESCRIPTION OF THE INVENTION

The invention described herein provides new methods for determining the water-wetting or oil-wetting properties of both natural and artificial materials through the extraction of tightly-associated liquids ("TALs") under selected, and in aspects a plurality of, conditions. In aspects, the wettability characteristics of a material provided by the disclosed methods can provide insight into the character of larger substances from which the material may be sampled.

In certain non-limiting aspects, the wettability characteristics of a material identified by the application of the methods described herein can aid in characterizing the larger substance, such as for example but not limited to when the methods are applied to petroleum exploration endeavors. In aspects, a TAL is an oil or water and the material to which the methods described herein are applied are petroleum drill cuttings representative of rock spanning at least a portion of the length of an oil well. In aspects, decisions related to the direction of petroleum exploration and extraction activities related to a geographical area from which samples are obtained, or activity related to a specific oil well, can be made based in part upon the oil- or water-wet character of the cuttings identified by the method(s) of the invention.

At least in part, the invention described here provides new methods of using water obtained from sample(s) of a geologic material to assess wettability and to determine whether the sample(s), and the associated geographical area from which they came, are associated with a high likelihood that oil is present today; or, that the area(s) identified by samples having high oil saturations, e.g., being oil-wet/oil-wetting, represent area(s) having been an active reservoir or pay zone in the past and which have an increased likelihood of being or having been associated with an oil producing system (e.g. the presence of one or more present or past pay zones within the same formation, play, or otherwise within the same geological area or geological unit).

In one aspect, the invention provides a method of analyzing the wettability characteristics of a material without changing the physical structure of the material being analyzed, comprising subjecting the material to (a) one or more vacuum conditions; (b) one or more temperature conditions; (c) one or more immediate environmental conditions having, e.g., a saline or surfactant nature; or (d) any combination of one or more of (a)-(c), wherein modifying one or more of (a)-(d) changes the amount of volatile hydrocarbons, water, or both volatile hydrocarbons or water released from the material, and further wherein changes in the amount of volatile hydrocarbons, water, or both volatile hydrocarbons or water released from the material under varying any one or more of (a)-(d) is representative of the oil- or water-wetting characteristic of a material. Vacuum conditions, temperature conditions, and immediate environmental conditions are described in detail elsewhere herein. In aspects, the invention provides methods for quickly applying such an analysis, such that one or more TALs are released within a short period of time, such as for example within 3, within 2, or within one hour such that the method can be used as a quick tool for assessing material characteristics such as oil content (e.g., having an oil-wet nature). In further aspects, the invention herein provides for methods of screening for substances which are capable of establishing an environmental condition under which one or more present TALs in a material are released within an established time period.

In certain aspects, modification of the physical structure of a material (physical disruption) changes the amount of a TAL released by a sample. In some facets, comparison of the analysis of EEF/EEL/EEW and RRF/RRL/RRW from a non-physically disrupted sample to the analysis of the same sample(s) after physical disruption (e.g., physically disrupted after the initial analysis of EEF/EEL/EEW and RRF/RRL/RRW whereby RRF-PD/RRL-PD/RRW-PD is released) provides wettability characteristic information which may provide additional, or, in aspects different, wettability characteristics than those obtained when physical disruption is not performed.

For example, in one exemplary aspect, the invention described herein provides a method of analyzing a collection of samples from a geologic formation to identify formations with an increased likelihood of containing a petroleum deposit by identifying oil-wet reservoirs indicating, or indicating a higher probability of, and/or a higher correlation with, a present-day or past petroleum deposit or oil accumulation, comprising (a) collecting a plurality of samples obtained from different locations of a geologic area, each sample comprising a solid geological material (e.g., a petroleum drill cutting, a core, or other material that at least comprises some analyzable solid material associated with the geologic area); (b) subjecting the samples to a method comprising (I) measuring at least substantially all of the easily extractible water ("EEW") contained in at least a first sample in a group of samples by a first analysis that provides a first measurement corresponding to the amount of EEW in the sample; and (II) measuring at least substantially all of the remaining, release-resistant water ("RRW") or combined water (i) in the first sample in a second analysis of the first sample that provides a second measurement corresponding to RRW, combined water, or both; or (ii) in at least one second sample that is co-located with the first sample to provide a second analysis that provides a second measurement corresponding to RRW, combined water, or both of co-located samples; and (c) evaluating the EEW alone or the relationship between the first measurement and second measurement (or combinations of such measurements, e.g., the combined water) to identify whether in any one or more groups of samples in the collection of samples the EEW alone or the relationship between the first measurement and second measurement, combination thereof, or any relationships derived therefrom is indicative of, or indicates a higher probability of, a nearby petroleum deposit.

In some embodiments, EEW and RRW can be replaced by TALS comprising EEF and RRF, wherein the fluid is representatively measured by the analysis of volatile hydrocarbons. In certain embodiments, physical disruption is applied to all samples subjected to the method. In some aspects, samples are first analyzed as described and following such an analysis are subjected to physical disruption, such physical disruption then followed by further, separate analysis of water released after disruption. In certain alternative embodiments, co-collected sample sets, each representing the same collection points within a geological area, are subjected to the method, however one sample set is not subjected to physical disruption, e.g., in aspects is a set of samples sealed at the well and a second sample set is subjected to drying by laboratory-induced aging methods described herein and then subjected to analysis by the method incorporating a physical disruption. In such aspects, differences in the resulting analysis of TALs between the two sample sets/two sets of analysis can be indicative of the oil- or water-wetting nature of the samples. One would expect that samples sealed at the well would have higher amounts of volatiles, as no volatiles would have been allowed to escape prior to analysis. One would presume, surprisingly incorrectly, that subjecting samples to drying by laboratory-induced aging methods would allow for more volatiles to dissipate prior to analysis, and, hence, they would not be detectible upon analysis. However, it has surprisingly been identified that the physical disruption of such laboratory-aged/dried samples releases very tightly-held material associated liquids. In one aspect, such liquids are held so tightly by the material that they surprisingly are not otherwise accessible without physical disruption or application of a similar disruptive/extracting force(s), condition(s), or combination thereof. When, e.g., physically disrupted, samples are capable of releasing such materials (SRRW such as RRW-PD), if present. In aspects, upon analysis, when laboratory-aged samples having a higher total oil (volatile hydrocarbon) response than that of their corresponding sealed at the well counterpart sample, such samples can be identified as oil-wetting, and the geological location from which such samples were collected can be identified as oil wetting, aiding in the characterization of such a geological area and in aspects guiding the decision making relating to the operational activity in and around such an area.

In my previous patent applications and patents, I have demonstrated that tight, non-permeable rocks, retain their oil and gas much better than good quality, permeable, reservoir rocks. Therefore, in respects, it can be difficult to find reservoirs using the oil and gas contents of cuttings, except in the negative sense in which oil and gas poor cuttings are considered to have been more likely sourced from oil and gas filled reservoirs than are cuttings containing larger amounts of oil and gas. The identification of the ability to ascertain such oil and gas-rich cuttings previously unidentifiable as such is one aspect of this invention. The methods of the invention described here can be applied to permeable cuttings, non-permeable cuttings, or both. Previous methods for characterization of such permeable and impermeable (or low permeable) cuttings are provided in my prior patent applications and issued patents.

Aspects of the invention are characterized by being applicable to single samples, collections of samples, or collections of co-located samples. The analysis of single samples can provide insight into the characteristics of a single material, e.g., an artificial material used in such industries as medical devices, electronics, or other high-tech industries where the water-wetting nature of materials can be important to functionality of such devices or at a minimum an applicable, or even important and/or desirable way to characterize such a material. Collections of samples can be utilized to more fully characterize a larger substance from which a collection of samples is obtained, such as a geological area, such as a petroleum well. In aspects, a collection of samples can be a plurality of samples collected across a depth or length of an oil well, wherein differences in results from the applied methods can identify important differing characteristics in the rock thereof, such as differences in the water- or oil-wetting nature of rock thereof. In aspects, such differences can allow identification of oil-wet rock which may direct petroleum operations accordingly. In aspects, co-located samples can be utilized in the methods described herein as such co-located samples may increase sample sets providing a way to supplement separate samples sets. In aspects, co-located samples can provide an opportunity to perform one analysis, e.g., extraction of water under one condition, while one or more other, different water extraction analyses can be performed on co-located sample(s), wherein results of the two analyses can be combined to create a single characterization of a substance from which the samples were collected (e.g., a geological area such as a formation or a petroleum well). In aspects, co-located samples can also or alternatively provide an opportunity to subject the co-located samples or sample sets to different sample processing and analytical techniques wherein the comparison of results from the application of the methods described herein to the two samples or sample sets having undergone different processing results in data not otherwise available on a uniformly treated sample or sample set alone.

Further description related to the materials and samples, tightly-associated liquids (TALs) and selected condition-extracted TALs, as well as analytical methods and related devices related to these and other aspects of the invention are further described in the sections which follow.

Materials and Samples

As is discussed herein, the methods of the invention, and the devices designed to aid in their application, can be applied to a material or sample(s) of a material, e.g., a single sample or a collection of samples. In discussion the materials and samples which may be used in the disclosed methods, the terms "sample," "samples," or "sample(s)" may be used, which should be interpreted as meaning a single or a plurality of samples of a material which may or may not be a representative part of a larger substance. The terms "material," "materials," or "material(s)" may be used, which should be interpreted as meaning the subject of testing or analysis, which is represented by one or more samples of the same, except in aspects in which methods are applied directly on a material rather than a sample.

In certain aspects, the methods described herein can be applied to any material describable as having a wettability character, e.g., water-wet or oil-wet nature. In aspects, the methods described herein can be applied to any material having a strong oil-wet nature, having a strong water-wet nature, or having a wettability character along the spectrum therebetween.

In most aspects, the material is a semi-solid or solid material. In some aspects, the material is a pure material, while in alternative aspects the material is a composition of one or more materials, such materials being either natural or artificial. In some aspects, the material is uniform in its nature. In other aspects, the material is non-uniform, such that it may have cracks, fissures, pores, or otherwise characteristics such that one location within the sample may be different in composition than any other one or more locations within the material.

In some aspects, the material can be a natural material. In aspects, such a natural material can be a biological material, such as for example but not limited to biological ceramics and ceramic composites (e.g., shells, teeth and bone), biological polymers and polymer composites, (e.g., hooves and horns), biological elastomers (e.g., skin and cells), biological cell-based materials (e.g., wood, beaks, and feathers), as well as man-made but bio-inspired materials such biomimetics (e.g., such as those found in aerospace, building design, fiber optics, and adhesive technologies) as well as molecular-based biomimetics. In some aspects, the material can be a man-made material comprising natural materials, such as, for example, a textile. In aspects, the material can be a resin. In some aspects, a natural material can be a pure metal, a plant-derived material, or a geological material, such as stones and rocks. In some aspects, such rock samples can be related to petroleum exploration operations, such as core samples or petroleum drill cuttings. In certain aspects, the material can be an artificial material. In aspects, the material may be a material used in a manufactured device. In such aspects, the artificial, man-made, or otherwise synthetic material can be a material used in the manufacturing of, e.g., medical devices, electronic devices, or for example pharmaceuticals (e.g., capsules). In aspects, the material can be a plastic or a composite.

According to certain facets, the sample is a core sample from an oil well, including but not limited to a sidewall core. In certain aspects, the samples utilized in the methods described herein are petroleum drill cuttings. In aspects, the petroleum drill cuttings can be rock bit cuttings or polycrystalline diamond compact (PDC) bit cuttings. In certain facets, most, generally all, or at least substantially all cuttings are PDC cuttings.

In aspects, the material is a sample of a larger substance. In one aspect, the material is a sample of a larger component, device, or, e.g., larger lot of an, e.g., manufactured material. In aspects, the material is a sample of a larger substance such as rock from a geological area. In aspects the geological area can be any geological area, and the material can be a sample of rock obtained from any part of such a geological area. In aspects, the results of analysis on any one or more samples can be informative about the characteristic(s) of the larger substance from which it was obtained, or, at a minimum, informative about the specific location within the larger substance from which the sample was obtained.

In aspects the methods herein comprise obtaining a plurality of samples from different parts of an area of the substance, such as for example obtaining at least about 2, at least about 5, at least about 10, at least about 20, at least about 50, at least about 100, at least about 200 or more, such as at least about 500, or at least about 1000 or more samples from different parts of an area of the substance. In aspects, samples can be collected from different parts of a larger substance such that the characteristics of the larger substance can be mapped based upon the results of the analysis of samples collected from different locations within it, wherein differences in one or more characteristics of the larger substance across its area can be identified based on the application of the methods described herein to the samples. For example, the samples can be drill cuttings collected across a depth or a length of an oil well.

In specific aspects, the substance is rock from a geological area including but not limited to a geologic formation, such a formation including but not limited to a freshwater petroleum site, and wherein the geologic formation can comprise one or more low visibility oil plays, and the practice of the method is associated with a combination of any or all thereof.

Sample Collection Techniques

Samples can be collected by any sample collection technique. Samples can be collected, for example, by random selection representative fractions of a larger substance such as obtaining random samples of a manufactured material during a manufacturing process, or for example specifically collecting a first, a middle, and a last sample from a production batch of material or any relevant collection technique common in quality control procedures. In aspects there may be a collection technique which interferes with target analyte analysis, and accordingly such collection techniques should be avoided.

As stated previously, in aspects, samples subjected to the methods herein are petroleum drill cuttings. In facets, a petroleum drill cutting sample can be a sample which is not sealed-at-the-well upon collection. In facets, a petroleum drill cutting sample can be a sealed-at-the-well sample, a site collected sample, or can be an aged (e.g. chronologically aged, as in the sample was collected at a time significantly different from the time of analysis, such as for example approximately 1 month prior, approximately 2 months prior, approximately 4 months prior, approximately 6 months prior, approximately 8 months prior, approximately 10 months prior, approximately 12 months prior or more, such as for example about 18 months prior, about 24 months prior, about 30 months prior, about 36 months prior or even more, as in about 3.5 years, about 4 years, about 4.5 years, or even as many as 5 years prior or more) to the time when the sample is analyzed) or artificially aged sample (artificial aging of samples is described in my earlier filed patent applications, but generally comprises subjecting the samples to conditions that cause the loss of external water). Drying and aging of samples after collection is discussed further elsewhere herein. In cases where the sample is associated with formation and/or production water (often lumped together as "production water" in the aspects provided herein, also described as "external water"), the method typically will comprise removing at least some, most, substantially all, or all of such external water from the sample prior to performing the other steps of the method.

Location of Collected Samples

According to some aspects, sample material can be collected as one or more representative samples of a larger substance. In aspects, the location of the sample collection is not relevant. However, in some aspects, the location of sample collection is relevant, such that the results of the analysis can provide information about the characteristics of a larger substance of which the sample was collected from one or more locations.

In aspects where the material is a rock sample, such as a drill cutting(s), the geologic area from which a sample is taken can be any geologic area (e.g., a formation, a formation member, a formation group, a basin, a play, a region or area of a play, a site within a play, a specific petroleum well, an area of prospective drilling, a reservoir, or the like) wherein the water composition of the solids contained therein may be of interest. More specifically, the geological area can be a formation which is of interest or potential interest in connection with petroleum exploration or production. For example, the formation can be an area known to currently contain petroleum, known to previously contain petroleum (e.g., an old well), or under exploration to discover the potential of, petroleum, oil, or gas deposits. A geologic area can have unknown potential for such deposits or may have been shown to hold potential for such deposits via use of other analytical methods. In some embodiments, the geologic area/region has not been shown to comprise, using other analytical methods, a relatively high likelihood of comprising a pay zone. In some aspects, the geologic region comprises one or more low visibility plays. In some aspects, the region is a region that is associated with any of the above-described conditions that substantially pose a risk to comprising low visibility plays (e.g., by being a freshwater formation). In certain aspects, a material is from a reservoir within a site of an oil production play, such a play optionally being a low visibility play. In some aspects, the material is rock from a well drilled in a reservoir. In some aspects, the material is drill cuttings or core sample(s).

In some aspects the analysis of a sample, e.g., a cuttings sample from a petroleum drilling operation, takes place within 2 kilometers of the point of collection, such as for example the samples are collected from a geological formation or for example from an active petroleum exploration or production drill site and analysis of EEW, analysis of the RRW, analysis of an SRRW such as RRW-PD, or analysis of any or all thereof, and/or any data processing using such results (such as sums and/or ratios of such data) of the method are performed within about 1.5 kilometers, for example within about 1.25 kilometers, within about 1.1 kilometers, within about 1 kilometer, or less from the point of collection, such as within about 500 meters, within about 400 meters, within about 300 meters, within about 200 meters, within about 100 meters, or even less, such as within about 80 meters, within about 60 meters, within about 40 meters, or even within about 20 meters of the point of collection. In certain aspects, the proximity of testing reduces the amount of time it takes to obtain results and can in aspects aid in the ability of well operators to utilizes data obtained by the application of the method to direct operations in real-time, e.g., results can be obtained within for example, about 1 week, about 6 days, about 5 days, about 4 days, about 3 days, about 2 days (48 hours), 1 day (24 hours), or within about 12 hours, within about 6 hours, within about 3 hours, or within about 1 hour (e.g., within 30, 15, 10, or 5 minutes) of collection.

Typically, methods of the invention are performed using multiple samples from one or more sites and from one or more locations within such one or more sites. Any suitable number of samples can be provided (or collected) in performance of such multi-sample methods. In aspects, at least about 10 samples, at least about 25 samples, at least about 50 samples, at least about 80 samples, or at least about 100 samples are subjected to analysis. In aspects, more than 100 samples, such as at least about 150 samples, at least about 200 samples, at least about 250 samples, at least about 300 samples, at least about 400 samples, at least about 500 samples or more, such as at least about 1000 samples, at least about 1500 samples, at least about 2000 samples or more are subjected to analysis.

Samples can be obtained from any suitable location within one or more sites. In aspects, samples are collected from one site. In other aspects, samples are obtained from multiple sites. In aspects, a single sample can provide characteristics of the material from that single location; collections of samples, when co-located, can provide information about the characteristics of that single site location; collections of samples representing dispersed sites can provide information about the characteristics of a larger geological area, such as, for example, differences in characteristics across a play.

In aspects, the invention provides methods of performing analysis on collections of samples from the same location within a single geological formation. Accordingly, in some aspects of the present invention, the analysis elements and methods as described for single sample analysis can be applied to co-located samples. As used herein, "co-located" samples are two or more samples collected from within a defined area of a geological formation, such a defined area being essentially the same location within a single geological formation, that is the two or more samples were collected within about 250 meters of one another, such as about 200 meters of one another in any single direction, such as for example within about 200 meters, within about 175 meters, within about 150 meters, within about 125 meters, or within about 100 meters of one another, such as for example within about 80 meters, within about 50 meters, within about 40 meters, within about 20 meters of each other, within about 10 meters of each other, or within about 7 meters of each other (e.g., about 5 meters of each other), e.g., about 10-200, about 15-150, about 17-100, or about 20-80 meters of each other, etc.).

In aspects, the analysis of co-located samples allows for different analysis to be performed on different co-located samples. Accordingly, in some aspects, the present invention provides a method of analyzing a collection of two or more co-located samples obtained from a defined area of a geologic formation to identify formations with an increased likelihood of containing a petroleum deposit comprising (a) collecting two or more samples obtained from a defined area of a geologic formation that is no more than about 100 meters in any direction, each sample comprising a solid geological material; (b) subjecting the samples to a method comprising (I) measuring at least substantially all the easily extractible water ("EEW") contained in at least one of the samples by a first analysis that provides a first measurement corresponding to the amount of EEW in samples in the location; (II) measuring at least substantially all the release resistant water ("RRW") the combined water, or both, in at least one of the samples by a second analysis that provides a second measurement corresponding to RRW, combined water, or both in samples in the location; and (c) evaluating the relationship between the first measurement and second measurement in the samples to identify whether the relationship is indicative of a higher probability of, or higher probability of correlation with the presence of, a petroleum deposit in a part of the formation associated with the samples.

In facets, the analysis of steps (a) and (b) of the method of the preceding paragraph can be done on the same or different, co-located samples. According to certain embodiments, a measurement of EEW can be obtained from one or more of the co-located samples and/or a measurement of RRW can be obtained from one or more of the co-located samples. In some aspects, two co-located samples are considered to be substantially identical to one another in their ability to represent the defined area of the geological location from which they were taken such that use of EEW or RRW data from any two or more samples for any analysis of the relationship between them, including a calculation of combined water, is considered interchangeable. Accordingly, in some aspects, a calculation of combined water can be obtained by using the EEW or RRW data from any two or more co-located samples, and/or an analysis of the relationship between EEW, RRW, and combined water can be calculated using any two or more co-located samples, as if the EEW and RRW data was obtained from a single sample as described in the single sample analytical methods herein.

Co-located sample analysis using the methods described herein can be applied using, e.g., samples of petroleum cuttings collected from an inactive well, from active petroleum exploration or production drill sites, or previously unexplored, potential petroleum drill sites and used to evaluate the potential value of starting new operations in, from, or around an inactive well or previously undrilled formation or also or alternatively to direct real time petroleum drilling operations at an active drill site.

A sample can be obtained from geological formations having never been explored or having never been a site of a previous drilling operation; can be obtained from an inactive well; or can be obtained from an active well as part of an ongoing drilling operation. In some aspects, the sample is from an inactive well and the methods applied herein comprise using data collected on one or more samples to start new drilling operations in, from, or around an inactive well. In some aspects, the sample is from an active well and the methods applied herein comprise using data collected on one or more samples to monitor or modify the direction of a drilling operation or to otherwise direct and inform real time petroleum drilling operations. In some aspects, the sample can be from a previously unexplored geological formation and used to determine the likelihood of the geological formation yielding an amount of petroleum, gas, or oil sufficient to warrant implementation of a drilling operation.

Still further, the invention also provides methods of performing similar techniques on collections of many (e.g., 3 or more, 5 or more, 10 or more, 20 or more, 50 or more, or 100 or more) samples from distinct parts/regions of a geologic formation. Such collections of samples may be referred to as "dispersed location samples" and as used herein, "dispersed location" samples refer to a collection of at least 5 samples, for example at least about 5 samples, at least about 6 samples, at least about 7 samples, at least about 8 samples, at least about 9 samples, or at least about 10 samples, such as for example at least about 11 samples, at least about 12 samples, at least about 13 samples, at least about 14 samples, or at least about 15 samples, such as for example at least about 16 samples, at least about 17 samples, at least about 18 samples, at least about 19 samples, or at least about 20 samples (and typically even more such as at least about 30, at least about 40, at least about 50, at least about 75, at least about 100, at least about 150, or at least about 200 samples (e.g., about 10-500 samples, about 20-500 samples, about 30-600 samples, about 10-1000 samples, about 20-1000 samples, about 50-1000 samples, such as about 100-500 samples, etc.) from at least about 5 different locations in a geologic formation (such as for example at least 5 separate locations, for example at least about 5 locations, at least about 6 locations, at least about 7 locations, at least about 8 locations, at least about 9 locations, or at least about 10 locations, such as for example at least about 11 locations, at least about 12 locations, at least about 13 locations, or at least about 15 locations, such as for example at least about 16 locations, at least about 17 locations, at least about 18 locations, at least about 19 locations, or at least about 20 locations, e.g., about 5-250 locations, about 5-500 locations, about 10-500 locations, about 10-250 locations, about 20-600 locations, about 20-400 locations, about 25-250 locations, or about 50-500 locations).

In some embodiments, a collection of dispersed samples can be used in the present invention according to the methods described previously for both single sample analysis and co-located sample analysis. In some aspects, the methods described previously as applied to single sample analytical methods and co-located sample analytical methods can also be applied to methods applied to collections of separately located samples, and vice versa. In some aspects therefore, the present invention provides a method of analyzing a collection of samples from a geologic formation to identify formations with an increased likelihood of containing a petroleum deposit comprising (a) collecting at least about 10 samples obtained from at least about 10 different locations in a geologic formation, each sample comprising a solid geological material; (b) subjecting the samples to a method comprising (I) measuring at least substantially all the easily extractable water ("EEW") contained in each sample by a first analysis that provides a first measurement corresponding to the amount of EEW in the sample(s); and (II) (A) measuring at least substantially all the remaining, release-resistant water ("RRW") in each sample, the combined water in each sample, or both, in a second analysis that provides a second measurement corresponding to RRW, combined water, or both of each of the samples, or (B) measuring the combined water, RRW, or both from a second sample or set of samples in the collection that is co-located with the first set of samples in a second analysis that provides a second measurement corresponding to RRW, combined water, or both of samples in the location; and (c) evaluating the relationship between the first measurement(s) and second measurement(s) to identify whether for any group/groups of samples in the collection of samples the first measurement and second measurement associated with such samples is indicative oil-wet cuttings which are indicative of a higher probability of the petroleum deposit today being, or having been in the past, in a part of the formation associated with the location from which samples were obtained.

In aspects, methods are applied on both dispersed location samples and co-located samples (e.g., a method is applied on at least 10, at least 50, at least 100, at least 200, at least 250, at least 300, or at least 500 samples from at least 5, 25, 50, 100, 125, 150, or 250 locations or at least 3, at least 15, at least 35, at least 75, at least 85, at least 100, or at least 150 locations, such that at least about 25%, 33%, or at least about 50% of the samples are samples that are co-located with other samples in one of the dispersed locations). Such methods allow multiple data points to be obtained for most, generally all, or substantially all locations, each location being separated by a distance as described elsewhere herein.

In some aspects, dispersed location sample analytical methods comprise use of a collection of co-located samples, the co-located samples being obtained from an area that is no more than about 100 meters in any single direction, no more than about 80 meters in any single direction, no more than about 50 meters in any single direction, such as no more than about 50 meters, no more than about 45 meters, no more than about 40 meters, no more than about 35 meters, no more than about 30 meters, no more than about 25 meters, no more than about 20 meters in any single direction, no more than about 10 meters in any direction, or no more than about 5 meters in any direction.

In some aspects, the dispersed location sample analytical methods comprise performing the method(s) of the present invention on a collection of at least 50 samples collected from an area of the formation that measures at least 100 meters in at least one direction, such as for example a collection of at least about 50, at least about 60, at least about 70, at least about 80, at least about 90, or at least about 100, such as at least about 110, at least about 120, at least about 130, at least about 140, or at least about 150 samples collected form an area of the formation that measures at least about 100 meters, at least about 150 meters, at least about 200 meters, at least about 250 meters, at least about 300 meters, at least about 350 meters, at least about 400 meters, at least about 450 meters, or at least about 500 meters, such as for example at least about 550 meters, at least about 600 meters, at least about 650 meters, or at least about 700 meters in one any one direction.

In aspects, an area/location that defines where different dispersed samples or groups of dispersed samples are obtained from will have maximum dimensions in all areas as described in the preceding two paragraphs (e.g., in an aspect each dispersed location is less than about 100 meters, less than about 50 meters, less than about 20 meters, or less than about 10 meters in all directions).

As alluded to previously, the wettability of characteristic of a material may not in aspects be clearly defined as "oil-wet" or "water-wet", in that there is a continuum between total oil wetness and total water wetness. This can be observed, for example, in data shown in the Examples provided herein, where convergence of oil- and wet-indicators (represented by curves of graphs) occurs. The movement of the curves toward one another before they cross illustrates a gradation from one type of wettability to the other type of wettability (e.g., from water-wet to oil-wet or from oil-wet to water-wet. In aspects, when analyzing a group of samples representing changing depth or changing lateral distance, ratios of values approaching 1 from either direction can indicate rock transitioning from having one wetness character to another. In aspects, samples approaching an EEW:RRW of 1 from values less than 1 indicate movement toward a more oil-wet nature. This is also true of a ratio of EEW:combined water ratio of less than 0.5 approaching 0.5, the approach to 0.5 indicating transition toward an oil-wet characterization. In aspects, such ratios are used as cutoffs for taking further steps, such as the application of petroleum removal methods based on the oil-wetting or water-wetting properties of the material in an area.

In some aspects, the dispersed location sample analytical method comprises identifying two or more groups of samples in an area that are associated with an EEW:RRW (EEW-to-RRW ratio) of at least about 0.7, at least about 0.8, at least about 0.9, or at least about 1, such as at least about 1, at least about 1.1, at least about 1.2, at least about 1.3, at least about 1.4, at least about 1.5, at least about 1.6, at least about 1.7, at least about 1.8, at least about 1.9, or at least about 2, which are separated by one or more samples having an EEW:RRW of less than about 1, such as less than about 0.9, less than about 0.8, less than about 0.7, less than about 0.6, less than about 0.5, less than about 0.4, less than about 0.3, less than about 0.2, or less than about 0.1. In aspects, areas having a more oil-wet nature than another are indicated by the approach of the EEW:RRW ratio toward 1 over a span of a distance such as a well depth or length.

In further aspects, the present method of dispersed location sample analytical methods comprises identification of an area of a geological formation associated with at least one group of samples in which the ratio of EEW:combined water (EEW-to-combined water ratio) is at least about 0.5, such as at least about 0.3, at least about 0.4, at least about 0.5, at least about 0.6, at least about 0.7, at least about 0.8, at least about 0.9, or at least 1 and associating the location from which such a group of samples was taken as a location having a high probability of petroleum being in or near the area. In aspects, areas having a more oil-wet nature than another are indicated by the approach of the EEW:combined water ratio toward 0.5 over a span of a distance such as a well depth or length. In aspects such methods can identify oil-wetting rock and in certain facets locations with an increased likelihood of being or having been associated with an oil producing system.

Still further, the method of dispersed location sample analytical methods comprises identifying two or more groups of samples in an area that are associated with an EEW:combined water of at least about 0.5, such as at least about 0.5, at least about 0.6, at least about 0.7, at least about 0.8, at least about 0.9, or at least about 1 which are separated by one or more samples having an EEW:combined water ratio of less than about 0.5 such as less than about 0.5, less than about 0.4, less than about 0.3, less than about 0.2, or less than about 0.1 and associating the higher ratio area as an area more likely to comprise a petroleum deposit. In aspects such methods can identify oil-wetting rock and in aspects locations with an increased likelihood of being or having been associated with an oil producing system.

In some embodiments, the method comprises identifying an area associated with at least one group of samples in which the ratio of EEW-to-RRW is at least about 1, the EEW-to-combined water ratio is at least about 0.5, or both, such scenarios being associated with a higher probability of the presence of a pay zone at the location from which the representative samples were collected.

In certain embodiments, the method comprises comparison of two or more geographical areas, such as two or more specific geographical locations, such as two or more wells and the specific locations (e.g., depths or spans) therein. In certain embodiments, the method comprises comparison of the wettability characteristics of such locations. In some aspects, the invention provides a method of (1) identifying a geographical area of interest, such as a geological unit, a formation, a sub-formation or member of a formation, a group of formations, a basin, a play, a region or area of a play, or a reservoir; (2) obtaining a first and at least a second set of samples, e.g., 10 or more, 25 or more, 50 or more, 100 or more, 250 or more, or 500 or more samples from at least 2, 5, 10, 20, 50, or at least 100 locations within the geographical area of interest, such as each being from separately drilled wells; (3) identifying, from within the first collection of samples from the first location, a group of samples having a mole fraction of EEW which is greater than the mole fraction of RRW, and identifying such a group of samples as representative of a specific location comprising oil-wetting material; and (4) combining/compiling and/or comparing the results to that from a corresponding group of samples collected from at least a second location. The mole fraction of EEW is represented by the calculation: mole fraction EEW=(Aliquot 1 water)/(Aliquot 1 water+Aliquot 2 water). The mole fraction of RRW is represented by the calculation:

Mole fraction RRW=(Aliquot 2 water)/(Aliquot 1 water+Aliquot 2 water).

In aspects, the resulting analysis can provide a map identifying specific locations of oil-wet rock within the geographical area, the orientation, span, or positioning of petroleum-related geographical features within the geographical area, or any or all thereof. In aspects, the more locations within the area which can be sampled and analyzed, the higher the resolution of such a map. In aspects, such a map can be used to identify areas having a higher probability of petroleum production. In certain aspects, such areas may be identified as having been at one point in time part of an oil production system. In some aspects, samples can be collected from a plurality of laterally or vertically drilled wells and the samples can be cuttings samples from such locations. In aspects, a map oil-wet rock can be used to identify the orientation or positioning of one or more oil-wet features in an area, aiding in one or more decisions on how to address such an area as it relates to petroleum exploration and petroleum production.

As is the case with the use of single sample analytical methods or co-located sample analytical methods, the methods herein can be applied to dispersed sample collections of petroleum cuttings collected from an inactive well, from active petroleum exploration or production drill sites, or previously unexplored, potential petroleum drill sites and used to evaluate the potential value of starting new operations in, from, or around an inactive well or previously undrilled formation or also or alternatively to direct real time petroleum drilling operations at an active drill site.

Sample Processing/Sample Handling

It can be appreciated that the way in which a sample is handled can impact target analyte, e.g., TALs, such as water, analysis results. In some aspects, prior to the step of the method where all readily extractable water ("REW", also referred to herein as "easily extractable water" or EEW) is analyzed, the sample is placed under conditions in which the sample is protected from exposure to or significant exchange with water from the environment. For example, upon collection, soon after collection, or within a reasonable time period after collection, such as for example within about 1 minute, within about 15 minutes, within about 30 minutes, within about 1 hour, within about 2 hours, within about 5 hours, within about 10 hours, within about 18 hours, within about 24 hours, within about 2 days, or within about 1 week from sample collection the sample can be sealed ("sealed-at-the-well"). Such sealing typically comprises placing the samples in a protective container, such as a sealed envelope, sealed bag, sealed plastic, metal or other container capable of protecting the sample from water gain or loss and is maintained under such protected conditions until required for testing and also or alternatively throughout testing though the method of testing may dictate removal of the sample from a first means of protection and application of a second means of storing, e.g., placing within a second means capable of being used within the applied method of testing, such as within a sample vial. In one exemplary aspect the samples are contained in a first container (e.g., a plastic tube) that is placed prior to analysis in a second crushable container (e.g., a sealable brass tube) as described further herein and in my earlier filed patent applications.

In certain aspects, sealing can be accomplished by encapsulating a sample or samples, placing the samples in an encapsulation material to protect the sample(s) from loss of a target analyte such as water. In aspects, encapsulation of a sample means that a sample is sealed within a confined space such that the volume of air space around the material is less than about 5%, less than about 4%, less than about 3%, less than about 2%, or less than about 1% of the volume of the material/sample(s) itself.

In certain aspects, sealing can be accomplished by encapsulating a sample or samples, placing the samples in an encapsulation material to protect the sample(s) from loss of a target analyte such as water. In aspects, encapsulation of a sample means that a sample is sealed within a confined space such that the volume of air space around the material is less than about 0.5%, 0.4%, 0.3%, 0.2%, or for example less than about 0.1%, such as less than about 0.08%, less than about 0.06%, less than about 0.04%, or even less than about 0.02% of the volume of the material/sample(s) itself.

In certain aspects, such an encapsulation method can be characterized as producing sealed-at-the-well samples wherein at least some, most, generally all, substantially all, essentially all, or all detectable environmental air is hermetically isolated from the sample upon collection. In aspects, air is not purged from the sample itself. In facets, the sample(s) i/are sealed within a container with no detectable air or minimal air (e.g., less than about 20%, 10%, 5%, or less than about 1% of the volume of the container is filled with air, such as less than about 0.5% or 0.1% of the volume).

In some aspects of this method, sample volatiles (e.g., TALs), are released by a piercing of a sealed container in which they are housed upon collection. This piercing may or may not be accompanied by, concurrently, preceding or following, a mechanism for physically disrupting the sample, such as by crushing. In aspects a method can comprise use of a trap, such as a liquid nitrogen trap, to capture (e.g., by freezing), released volatiles (e.g., oil, gas, water, and carbon dioxide). In aspects of my previous inventions, non-condensable air is pumped away, and the liquid nitrogen trap is exposed to high vacuum and exposed to an, e.g., mass spectrometer for analysis. In this invention the sample can be, in aspects, isolated from air by encapsulation. The encapsulated sample can be loaded into a chamber and that chamber, containing the encapsulated sample, can be bought under high vacuum. In my previous patents, at least in part, a function of a liquid nitrogen trap was in aspects to remove air. In aspects, if samples are encapsulated in an at least substantially air-free environment, the need for a liquid nitrogen trap can be eliminated; if samples are sufficiently encapsulated, a liquid nitrogen trap will not be required to remove the air. In such aspects, the encapsulated material could be brought into direct high vacuum communication with the, e.g., mass spectrometer, prior to releasing volatile(s) from the sample(s) through piercing and/or crushing or another method of destroying the sealing nature of the encapsulating material. In aspects, direct analysis, e.g., by mass spec of the volatiles released by the material can be attained without the need for the liquid nitrogen trap. In some aspects, absence of a liquid nitrogen chamber reduces or eliminates the separation of one or more compounds prior analysis. In aspects, the method could be conducted without such separation or, alternatively, with incorporation of one or more other suitable means for compound separation in place of a liquid nitrogen trap. In aspects, absence of a liquid nitrogen trap supports the ability to conduct the methods herein more quickly, e.g., in less time, supporting a higher-throughput analysis. In aspects, the gentle vacuum applied extraction is present in a method with or without the presence of a liquid nitrogen trap, and hence the presence of present-day fluids trapped within a sample is maintained.

In certain facets, use of an encapsulation material provides an improvement in the ability to analyze air trapped within a sample (as air exterior to the sample is removed prior to application of a vacuum prior to releasing its volatiles by comprising the encapsulation seal provided by the encapsulation material), such as for example analyzed air has a higher probability of having been extracted from the interior of the sample vs. being extraneous exterior air), results of such having a higher probability of being representative of the air trapped in the sample in the past versus being representative of present day, sample-collection-related air.

In certain aspects, analysis of such air may be applicable to, e.g., climate-related studies. In aspects, any such field of endeavor for which information about what air looked like in the past, when trapped within the material, could benefit from the methods and processes described, e.g., this type of encapsulation and approach to the measurement of air associated within a material.

According to certain embodiments, encapsulation can be a component of a method which analyzes any volatile described herein or in my previous work; that is, not just for water but for all volatiles. In aspects, it can be applied to methods comprising or lacking a liquid nitrogen trapping step (e.g., in devices or systems comprising or lacking a liquid nitrogen trap). In aspects, encapsulation step(s) can be incorporated into methods utilizing a single high vacuum pressure without a liquid nitrogen trap or at any single pressure with the incorporation of a liquid nitrogen trap, and, also or alternatively in methods utilizing multiple pressures with a liquid $N_2$ trap.

In one facet, encapsulation of samples can provide a mechanism for utilizing gentle extraction at faster throughput rates. In applications where higher throughput is advantageous, such as site-located instruments/site-located analysis/analyses, a method can be performed using a single high vacuum pressure with the encapsulated sample exposed directly to a mass spectrometer without the preliminary liquid nitrogen trap separation. In aspects wherein such a method is combined with MS-MS technology, enhanced compound characterization can be attained even without use of a liquid nitrogen trap.

In aspects, an encapsulation material is capable of protecting the sample(s) from loss of more than about 10%, more than about 9%, more than about 8%, more than about 7%, more than about 6%, more than about 5%, more than about 4%, more than about 3%, more than about 2%, or more than about 1% of a target analyte such as water. In aspects, such an encapsulation material is a plastic such as a shrink-wrap plastic. In aspects, an encapsulation material can be a tape in which the sample is sealed under or within layers of tape comprising an adhesive. In certain aspects, the encapsulation material is an epoxy such as a volatile-free epoxy. In aspects, any material utilized for such an encapsulation is a substantially or detectibly volatile-free material or also or alternatively is otherwise inert relative to impacting the results of an analysis of samples held therein. In certain aspects, samples can be submerged in a low volatile liquid such as an oil, or more specifically such as a diffusion pump oil, wherein the oil is later evacuated. In such an aspect, however, loss of potentially important volatiles may be experienced and hence may not be suitable for all applications. In some aspects, a suitable encapsulation material such as a shrink wrap or an epoxy can both eliminate air from impacting the sample and can further be brought under high vacuum, subjected to mechanical disruption leading to the physical disruption of the sample (e.g., subjected to crushing) as may be applied as an element of the methods of the invention, and in doing so no significant loss of volatiles may be experienced, such as for example less than 5%, less than 4%, less than 3%, less than 2%, or less than 1% of volatiles are lost or alternatively no amount of volatiles are lost that would detectibly or significantly alter the analysis of such volatiles.

Another useful aspect of encapsulation is the further expansion or extension of preservation time of, e.g., volatile compounds. In aspects such an ability to extend the time between collection and analysis can, e.g., allow for transport and extended storage before analyses. In certain aspects, the encapsulated material can further be placed within a sealed container. Such an additional step could be particularly important for highly volatile gases, such as for example, Helium.

In aspects, an encapsulation material is capable of protecting the sample(s) from loss of more than about 10%, more than about 9%, more than about 8%, more than about 7%, more than about 6%, more than about 5%, more than about 4%, more than about 3%, more than about 2%, or more than about 1% of a target analyte such as water. In aspects, such an encapsulation material is a plastic such as a shrink-wrap plastic. In aspects, an encapsulation material can be a tape in which the sample is sealed under or within layers of tape comprising an adhesive. In certain aspects, the encapsulation material is an epoxy such as a volatile-free epoxy. In aspects, any material utilized for such an encapsulation is a substantially or detectibly volatile-free material or also or alternatively is otherwise inert relative to impacting the results of an analysis of samples held therein. In certain aspects, samples can be submerged in a low volatile liquid such as an oil, or more specifically such as a diffusion pump oil, wherein the oil is later evacuated. In such an aspect, however, loss of potentially important volatiles may be experienced and hence may not be suitable for all applications. In some aspects, a suitable encapsulation material such as a shrink wrap or an epoxy can both eliminate air from impacting the sample and can further be brought under high vacuum, subjected to mechanical disruption leading to the physical disruption of the sample (e.g., subjected to crushing) as may be applied as an element of the methods of the invention, and in doing so no significant loss of volatiles may be experienced, such as for example less than 5%, less than 4%, less than 3%, less than 2%, or less than 1% of volatiles are lost or alternatively no amount of volatiles are lost that would detectibly or significantly alter the analysis of such volatiles.

Additional means of sample handling can be used to prepare the sample for testing or also or alternatively to maintain or preserve the sample in a form most suitable for water analysis. According to some aspects, the sample, e.g. a petroleum drill cutting, can be subjected to steps comprising one or more washing steps, one or more drying steps, one or more aging steps, or any other one or more steps which reduce or substantially eliminate process water from one or more samples. In embodiments, such any one or more preparative or preservative steps can be performed prior to any water analysis, e.g. prior to analyzing EEW, RRW, or performing any analysis of the results of the same. In embodiments, such any single or combination of preparative or preservative steps can be performed after any water analysis, e.g., after analyzing EEW, RRW, or performing any analyses of the results of the same. In aspects, a sealed-at-the-well samples can be analyzed using the methods described herein, then subjected to one or more preparative or preservative steps, and analyzed according to methods provided herein. In some aspects, such second analysis can be conducted after the sample is physically disrupted, e.g., crushed.

According to one aspect, the sample is subjected to a "dry cleaning," meaning any cleaning step in which undesirable material/debris and other external material, such as external water, is at least in part removed (some, most, substantially all, or all external water is removed) from the sample, without the use of significant amounts of water, or any amounts of water. Methods of the invention including a sample dry cleaning step represent a departure from conventional methods, including methods of focus in my earlier filed applications.

As used herein, "aging" a sample is a term describing storage of one or more samples under conditions where at least most, substantially all, or all of the external water is permitted to evaporate or otherwise be removed from the sample(s), typically over a period of more than 1 day, 2 days, 3 days, or one week. An "aging" step or method can, accordingly, be accomplished naturally, over time, by allowing the water to evaporate from the sample with no additional processing required. Also or alternatively, "aging" can be accomplished by an act of subjecting the samples to one or more artificial aging steps/methods wherein one or more steps are conducted to either a) speed up the water evaporation/removal process, b) increase the amount of external water which is eliminated in the relevant time allowed for aging the sample, or both a) and b) are accomplished. Such a process may be referred to as laboratory- or lab-aging, or laboratory- or lab-induced aging. According to certain embodiments, such aging steps can result in most, substantially all, or all external water to be removed from any one or more samples. In certain facets, substantially all external water is removed by application of one or more such processes. In aspects, sufficient external water is removed from all samples such that a baseline moisture level is obtained for each sample that is within about 10%, within about 5%, or even within about 1% of the baseline moisture level of any other sample to ensure that what is being detected by application of the method is relative amount(s) of water in a sample relative to another.

TALs/SCETALs

According to certain aspects, a tightly-associated liquid (TAL) held within a material can be any tightly-associated liquid which can be extracted and measured according to the methods described herein to provide insight into one or more characteristics of the material with which it is associated. In some aspects, a TAL can be analyzed using the methods described herein to assess the wettability character of a material. Surprisingly, in aspects, the invention describes use of tightly associated water to characterize the wettability nature of a material.

In certain facets, the TAL can be hydrophobic liquid, such as, for example, an oil. In aspects the TAL can be petroleum held within samples of geological material such as rock, e.g., such samples being core samples or petroleum drill cuttings from a petroleum exploration operation. In some embodiments, determining the amount(s) of tightly associated oil within one or more samples can provide insight into the oil-wetting characteristic of a larger substance from which the samples were obtained, such as for example specific oil-wetting rock locations within a geological area, e.g., a formation or a well, wherein the samples are drill cuttings collected at a plurality of locations across such a location.

In aspects, a TAL, in facets water as described herein, is actually contained in the solid material of the sample (e.g., in micro-fissures of the sample). In some facets, a TAL such as water can be bound to or otherwise tightly associated with the surface of the sample, such that it is not easily removed during sample handling or sample processing.

TAF/TAL/TAW in a material can be comprised of, as previously described, an EEF/EEL/EEW and/or an RRF/RRL/RRW. A TAF/TAL/TAW could also comprise NEF/NEL/NEW, however such fluids/liquids/waters (e.g., NEW) are typically not a component of the methods described herein, as the methods described herein typically do not comprise applying EEFEFs/EELEFs/EEWEFs or RRFEFs/RRLEFs/RRWEFs which are capable of extracting such fluid/liquid/water. The TAF/TAL/TAW(s) subject to extraction by the methods described herein are capable of being extracted by one or more EEFEFs/EELEFs/EEWEFs and/or RRFEFs/RRLEFs/RRWEFs. In some aspects, an RRFEF/RRLEF/RRWEF comprises an application of a force sufficient to physically disrupt a material, such as a mechanical force capable of crushing a sample material. In some aspects, release of a TAF/TAL/TAW is only possible after physical disruption of the material being analyzed. In aspects, the methods described herein comprise analysis of some, most, generally all, or all of the TAF/TAL/TAW of a material, such as some, most, generally all, or all of the EEW, and/or some, most, generally all, or all of the RRW of a sample.

In some aspects, a TAL may be referred to as a selected condition-extracted TAL (SCETAL). Such TALs are TALs extracted, at least in part, under specific conditions, such as, for example, upon exposure to select temperature, pressure (e.g., vacuum pressure), or select conditions, such as immediate environmental conditions. One example of a SCETAL is an SRRW, such as RRW-PD, which is extractable only under specific conditions, in the case of RRW-PD wherein the material with which is it associated is physically disrupted. A second example of a SCETAL is a TAL which is extracted upon exposure to a chemical condition such as for example a solution comprising a surfactant, a salt, or polyphenol(s), such that even after subjecting a sample of material to one or more of the methods described herein, placement of the material in a solution comprising such component(s) yields further extraction of a TAL.

Unless otherwise indicated, less than about 15% of any water extracted by the methods described herein, e.g., the total of EEW and RRW, RRW being inclusive of the RRW-PD fraction, extracted upon the application of a method described herein or measured as part of a method described herein is water from fluid inclusions. Fluid inclusion water typically will be resistant to even methods that are capable of extracting RRW, as such water is securely contained in the inclusion until the inclusion is ruptured. However, it is possible that some fluid inclusion water will be released if the sample is subjected to crushing, as required to extract RRW-PD, but even in inclusion-rich samples it is expected that the amount that will be contributed by inclusion water will, on average at least for a collection of samples, be a relatively small amount of the total sample water. According to embodiments, less than about 10% of the sample water such as less than about 5% of the water, e.g., less than about 2% of the sample water, less than about 1% of the sample water, less than about 0.5% of the sample water, less than about 0.2% of the sample water, or even less than about 0.1% of the sample water is attributable to water contained in fluid inclusions. The differences between fluid inclusions and other volatiles, which will include EEW and RRW, is well described in the above-referenced '031 patent publication and related patents, though in my prior applications SRRWs, such as RRW-PD as a specifically identifiable amount of an RRW, is not specified as it was not known or understood at the time of prior applications that such an amount/fraction could be specifically informative and beneficial in identifying the wettability characteristics of a material.

Analytical Methods

The analysis of TALs, such as EEW and/or RRW can generally be performed by any suitable method. In aspects, measurements are performed on extracted TALs, such as extracted EEW, RRW, or both.

In certain aspects, methods described herein can be utilized to extract one or more TALs, such as water, from a material. In aspects, quantifying or otherwise assessing the amount of a TAL(s) released can be accomplished by direct or indirect analysis of the extracted TAL itself, such as, e.g., using mass spectrometry, capacitance manometry, etc. as discussed herein. In one aspect, the measurement of a TAL, e.g., of water, is done in situ, without the extraction of either one or both of EEW or RRW. Such a method can include, for example, Fourier Transform-Infrared Spectroscopy (FTIR). Methods of performing FTIR suitable for the analysis of water content of materials, such as cuttings, are known in the art. Still other methods for in situ analysis of water content, without extract, also are known and can be similarly used, and the scope of this aspect of the invention is not limited to FTIR or any other single technique.

In other alternative aspects, or aspects which can be applied in conjunction with a direct or indirect measure of one or more TALs, an analysis of the differential loss of TAL from a material can be implemented. In certain aspects, comparing a starting condition of a material to the condition of a material after one or more subsequent condition applications, such as one or more vacuum extraction steps; or one or more heating steps; or one or more combination of vacuum and heating steps, could provide a measure of extracted TAL, such as water. In aspects such an analysis can be accomplished by use of FTIR. In certain facets, total water can be analyzed on a sample, prior to the application of any condition. In facets, such a sample can then be subjected to one or more conditions, such as vacuum pressure, heat, or both, releasing EEW however such EEW may or may not be directly measured. In facets, RRW can be analyzed after the application of vacuum pressure, heat, or both. In such a process, EEW can be calculated by subtracting the RRW from the total water measurement. In aspects, application of FTIR with, e.g., attenuated total reflectance capability, (FTIR-ATR), can be applied to measure the differential loss of one or more TALs, e.g., water, from a material, such as from rock samples such as cuttings. In aspects, examination of differential loss from a material could be accomplished using, e.g., a high precision mass balance. In aspects, use of such a technology can be accompanied by one or more steps or methods of confirming that the differential loss is due to loss of the TAL of interest, e.g., due to water loss.

In other aspects, the extraction of one or more TALs such as water from a material is detectibly or significantly enhanced by or dependent upon exposure of the sample to condition(s) or force(s) causing the release of one or more TALs.

In one facet, the invention describes a method of identifying the oil- versus water-wetting characteristic of a material without changing the physical structure of the material being analyzed, comprising subjecting the material to (a) one or more vacuum conditions; (b) one or more temperature conditions; (c) one or more immediate environmental/chemical conditions (e.g., conditions having a polyphenolic, saline or surfactant nature); or (d) any combination of one or more of (a)-(c), wherein modifying one or more of (a)-(d) changes the amount of oil, volatile hydrocarbons, water, or any combination thereof released from the material, and further wherein changes in the amount of oil, volatile hydrocarbons, water, or any combination thereof released from the material by varying any one or more of (a)-(d) is representative of the oil- or water-wetting characteristic of a material.

In one aspect, the invention provides a method of characterizing a material comprising (a) providing an analyzable amount of a material; (b) measuring the amount of easily extracted water in the material; and (c) characterizing the material based on the amount of EEW in the material. In aspects, such characterization is material wettability and the EEW is released upon application of one or more conditions.

In one further aspect, the invention provides methods for analyzing a sample obtained from a geologic area to identify parts of the area with an increased likelihood of containing a petroleum deposit. The steps of such an analytical method can include (a) obtaining one or more samples comprising a solid material from a geologic area; (b) measuring at least substantially all (and desirably all) of the readily or easily extractable water ("EEW") contained in the sample by a first analysis that released by exposure of the sample to at least a first condition, that provides a first measurement corresponding to the amount of EEW in the sample; (c) measuring (i) at least substantially all (and desirably all) of the remaining release resistant water (RRW) in the sample that is released by exposure of the sample to at least a second condition, (ii) the combined water in the sample, or (iii) both, in at least a second analysis that provides at least a second measurement corresponding to RRW, total water, or both; and (d) evaluating the individual measurements or the relationship between the first measurement and second measurement to determine if any of the individual measurements alone or the relationship between the first measurement and $2^{nd}$ measurement is indicative of a higher probability of a petroleum deposit.

In aspects, the methods can yield the release of EEW, RRW or both, sometimes specifically identifying an SRRW such as RRW-PD if such a condition, e.g., such a physical disruption, is applied.

According to some embodiments, the analysis of the relationship between EEW and either RRW and/or combined water can be a simple ratio calculation. E.g., in some aspects to analyze the relationship between EEW and RRW, the following calculation can be performed:

Relationship between EEW and RRW=EEW/RRW

Alternatively stated:

Relationship between EEW and RRW=EEW:RRW

According to embodiments, the analysis of the relationship between EEW and combined water can be expressed as a simple ratio. For example, to analyze the relationship between EEW and combined water, the following ratio/relationship can be used:

Relationship between EEW and COMBINED WATER=EEW/COMBINED WATER

Alternatively stated:

Relationship between EEW and COMBINED WATER=EEW:COMBINED WATER wherein in both cases COMBINED WATER=EEW+ RRW.

The individual amounts of EEW, the amount of combined water, and the relationship between EEW and RRW and/or combined water have been surprisingly demonstrated to be capable of identifying or contributing to the identification of areas of a geologic formation having a high probability of petroleum being in or near the area. Specifically, in contrast to previous disclosure in my earlier discoveries related to RRW, SRRWs such as RRW-PD specifically can provide important sample wettability-characterizing data.

According to certain embodiments, an EEW:RRW (EEW-to-RRW ratio) of at least 1 has been shown to be indicative of an area having a high probability of comprising a petroleum deposit. That is, in some embodiments, an EEW:RRW of at least 1, such as about 1, about 1.1, about 1.2, about 1.3, about 1.4, about 1.5, about 1.6, about 1.7, about 1.8, about 1.9, or about 2 is indicative of the potential presence of a pay zone. In several cases, as reflected in the examples provided herein, higher ratios, such as at least about 2, at least about 2.5, at least about 3, at least about 3.5, at least about 4, at least about 4.5, at least about 5, and higher, are obtained, and the methods of the invention can include using such higher threshold values for indication of a positive analysis if desired.

In further aspects, the present method comprises identification of an area of a geological formation, that is a ratio within a single sample, wherein the EEW:combined water (EEW-to-combined water ratio) is at least about 0.5, such as at least about 0.5, at least about 0.6, at least about 0.7, at least about 0.8, at least about 0.9, or at least 1 and associating the location from which such a sample was taken as a location having a high probability of petroleum being in or near the area.

In some aspects, methods of the invention comprise use of varying sample processing and treatment conditions (e.g., use of one or more select conditions) to distinguish sample characteristics which may not otherwise be apparent. For example, in one aspect, the oil-wetting nature of a sample of material obtained from a geological area can be obtained in order to identify one or more oil-wet locations within the geological area by a method comprising (a) obtaining from two or more locations within a geologic formation (i) two sets of samples, each set having samples collected from the same locations within the geologic formation; one set of samples having been hermetically sealed upon collection, and one set not sealed at the well upon collection, or alternatively (ii) a single set of samples hermetically sealed upon collection which is (1) later divided into two sets of samples such that one set is identifiable as hermetically sealed and one set is identified as unsealed, or (2) first analyzed as a hermetically sealed sample then reanalyzed after further sample preparation; (b) subjecting the second set of samples identified as unsealed or alternatively having first been analyzed as a sealed sample to aging through storage under conditions in which substantially all of the external water is permitted to evaporate ("lab-aged"); (c) measuring two or more volatile hydrocarbons in sealed samples extracted under vacuum conditions by any process capable of applying such conditions and providing such a total oil indication/response, if present, without mechanically disrupting the physical structure of the samples; (d) subjecting the unsealed, lab-aged samples, or alternatively the sealed samples having completed step (c) to physical disruption and measuring the same two or more volatile hydrocarbons extracted under vacuum conditions by any process capable of applying such conditions; (e) collecting a total oil indication/response, if present, from each sample analyzed in (c) and (d); and (f) identifying variations in the responses between the two sample sets of (c) and (d) as measured by (e), wherein a lab-aged sample having a higher total volatile hydrocarbon (oil response) result than that measured in a sealed sample obtained from the same location is indicative of oil wetting rock at that location.

The above-described method, applied as exemplified to geological samples, reveals and illustrates the importance and impact of varying sample conditions one analytical results and interpretation thereof. This particular embodiment of the invention is described further as an Example later in this disclosure.

Further analytical methods and conditions to which samples can be exposed according to such methods, such as temperature conditions, chemical/local environmental conditions, and pressure conditions, under which extraction of one or more TALs may be induced, are described below. According to some embodiments, any one or more such conditions utilized in methods described herein can be performed in combination with a mechanical disruption of the sample. In some aspects, samples can be exposed to a plurality of conditions, such as any combination of conditions described herein, in application of a method. For example, a sample may be exposed to a combination of one or more vacuum pressures in combination with one or more temperature conditions, with or without additional exposure to a condition causing physical disruption. In aspects, any EEW, RRW, or an SRRW such as RRW-PD released under different conditions are each independently measured.

Conditions

In many aspects as exemplified here, the method comprises extracting EEW and/or RRW from some, most, or all the samples, e.g., by applying one or more various conditions (which can comprise one or more forces) that are capable of extracting EEW and/or RRW, as applicable, usually without impairing the extraction and/or analysis of substantially all, or at least predominately all, of the other type of sample water in the sample when the analytical method is undertaken (not including storage time).

According to one embodiment, the first analysis of EEW, the second analysis of RRW or combined water, or both the first and the second analysis are performed by a method comprising FTIR, in-situ, without extraction of TAL, the application of a condition, or both. In other aspects, FTIR analysis is coupled with application of condition(s), such as application of heat, application of vacuum, or both, to the material along with FTIR.

According to some embodiments, at least substantially all EEW is extracted from the sample and the extracted EEW is measured. According to some embodiments, at least substantially all RRW also or alternatively is extracted from the sample and the extracted RRW is measured. In some aspects, each such extraction step results in substantially all of the EEW and the RRW, respectively, being extracted from the sample. In some aspects, each of the two extraction steps occur independently from the other. In some aspects, the two extraction steps occur sequentially. In some aspects, wherein co-located samples are collected, the two extraction steps occur using different, co-located samples. In aspects, the release of water is facilitated by the application of one or more conditions to sample(s).

According to some embodiments, the amount of EEW and RRW released is each respectively measured by a method suitable for measuring water content. Such a method can be any method capable of providing a measurement of water content and capable of yielding interpretable results according to the inventive method. In some aspects, the amount of water released from each extraction is measured by capacitance manometry (e.g., indirectly by capacitance manometry by means of measuring total pressure). In aspects, the amount of water measured is depended on the conditions applied to a sample prior to measurement.

In aspects, in conducting a method disclosed herein, one or more conditions can be applied in various combinations to sample(s) or subsets of sample collections, and in varying sequence, to facilitate the release of one or more target TALs.

Temperature Conditions

In some aspects, extraction of EEF/EEL/EEW and/or RRF/RRL/RRW can be conducted under a wide range of temperature conditions. In aspects, temperatures used in practicing methods of the invention can vary considerably, especially where high temperatures are used to remove material and freezing is used as a trapping method during analytical procedures as described in my earlier work. In this respect, as described therein, the overall system, including a sample container, may see temperatures ranging from about −273 degrees Centigrade (degrees C.) to about 500 degrees C., such as about −195 degrees C. to about 200 degrees C. In many aspects, the temperature in the system will not exceed or even possibly not reach 100 degrees C. In other aspects, the temperature a utilized analytical system will not exceed or possibly not reach 50 degrees C., particularly in the sample container. Further, while more extreme temperatures may be utilized in the practice of the analytical steps of the methods described herein, these extreme temperatures may not be reached in all parts of the analytical device being utilized, e.g., heat may be applied to the sample container but freezing temperatures may only be applied to a trap element of such a device.

In some aspects, extraction of EEW and/or the RRW (or combined water) can comprise trapping extracted water from relevant sample water extraction steps. In some aspects, trapping such water can be accomplished by any kind of trap suitable for releasably trapping extracted water. In some aspects, the trap is a media trap which is capable of releasably capturing a portion or all of the EEW, a portion or all of the RRW or a portion or all of both the EEW and RRW (or combined water). Such a releasable engagement can be by modification of the state of the temperature of the trap, for example controllably cooling the trap to facilitate capture of the extracted water(s) and/or for example controllably heating the trap to release trapped water from a media trap. Such a releasable engagement can also or alternatively be by other means aside such as a physical/mechanical media, chemical media, or other known methods for retaining water. According to certain embodiments of the present invention, the trap is a liquid nitrogen trap, a powered refrigerator, or a dry ice trap. In some aspects, the trap is capable of reducing the temperature of any contacted water to at least about −60 degrees C. (i.e., about −60 degrees C. or lower), such as at least about −65 degrees C., at least about −70 degrees C., such as to at least about −75 degrees C., at least about −80 degrees C., or even lower.

In certain aspects, methods of the present invention are performed without any use of a liquid $N_2$, e.g., in a liquid nitrogen trap.

The application of heat can be via any means suitable of heating the sample so as to cause release of any one or more waters (e.g. an EEW or an RRW, such as by incorporation of a heating element. Methods for external water from samples such as cuttings are known in the art and include simple boiling techniques, at least with respect to the removal of EEW. According to embodiments, such a pressure is a vacuum pressure. My previously filed patent applications provide extensive disclosures relating to the use of pressure extraction of volatiles from geologic samples, such as cuttings, which can be applied to these present methods.

Pressure Conditions/Vacuum Pressure

In some aspects, a condition applied to a sample as part of the methods of the invention can be a vacuum pressure. In aspects, application of a pressure can cause or aid in the extraction of EEW or RRW or both EEW and RRW (combined water) can comprise the application of any kind of pressure suitable for forcing the extraction of the target water (e.g., a high pressure, a vacuum pressure, or different application of both). In aspects, the amount of a TAL released upon application of a vacuum pressure is released after each discrete vacuum pressure application. In aspects, a continuous range of vacuum pressures may be applied.

In some particular aspects, a physical disruption of the sample is accompanied by or followed by an application of a pressure such as a vacuum pressure. In other aspects, vacuum pressure is used to extract EEW, RRW, or combined water, regardless of whether or not the sample has been first subjected to mechanical disruption. In some aspects, one or more vacuum pressures can be applied to a sample prior to a physical disruption of a sample. In some aspects, one or more vacuum pressures can be applied to a sample after a physical disruption of a sample. In some aspects, one or more vacuum pressures can be applied to a sample both prior to and following a physical disruption of a sample.

The vacuum pressure applied in any application of vacuum pressure for sample water extraction can be any suitable pressure capable of forcing the extraction of one or more of EEW, RRW, or both, as dictated by context and the nature of the sample and water.

In aspects, vacuum pressures utilized in the extraction steps of methods described herein can be less than about 100 millibars, e.g., between about 1 millibar to approximately 100 millibars, in certain aspects between about 10 and about 100 millibars. In aspects, methods can comprise application of one or more different vacuum pressures. In aspects, varying the vacuum pressure modifies the TAL release.

In some aspects, the method comprises applying a vacuum pressure during a first extraction step is sufficient to extract substantially all of the EEW. In some aspects, such a vacuum pressure for removing EEW can range between about 10 millibars and about 100 millibars, such as, e.g., between about 10 millibars and about 75 millibars, between about 12 millibars and about 60 millibars, or between about 15-60 millibars, e.g., between about 12.5-50 millibars, between about 10-50 millibars or 15-45 millibars, e.g., about 17.5-35 millibars, or 17-42 millibars, e.g., about 15-25 millibars, such as about 20 millibars.

Such vacuum pressures can be applied for any suitable amount of time. Examples of suitable times for the application of such vacuum pressures in the extraction of volatiles, including water, are described in previously filed patent applications. According to aspects, the time of vacuum application for the extraction of EEW, RRW, or both is about 1-15 minutes, about 1-12 minutes, about 2-12 minutes, about 3-12 minutes, about 4-12 minutes, about 1-10 minutes, about 2-10 minutes, about 3-10 minutes, about 4-10 minutes, about 2-8 minutes, about 3-8 minutes, about 4-8 minutes, or about 5-9 minutes, or about 5-8 minutes.

In some aspects of the methods described herein, a second vacuum pressure is applied in the step extracting RRW. Such a vacuum pressure is typically significantly lower than the vacuum pressure applied in the extraction of EEW (and accordingly provides a significantly stronger extraction). According to some aspects, the vacuum pressure applied during the extraction of RRW is less than about $2/5^{ths}$, less than about $1/3^{rd}$, less than about $1/4^{th}$, or less than about $1/5^{th}$ of the pressure applied in the extraction of EEW (e.g., less than about $1/6^{th}$, less than about $1/7^{th}$, less than about $1/8^{th}$, or less than about $1/10^{th}$ of the pressure applied in the extraction of EEW—such as about $1/3^{rd}$-$1/8^{th}$ of the pressure, about $1/3^{rd}$-$1/7^{th}$ of the pressure, about $1/3^{rd}$-$1/6^{th}$ of the pressure, or about $1/3^{rd}$-$1/5^{th}$ of the pressure, e.g., about $1/4^{th}$-$1/8^{th}$ about $1/4^{th}$- about $1/7^{th}$ or about $1/4^{th}$-$1/6^{th}$ of the pressure).

According to some aspects, a vacuum pressure applied in the extraction of RRW is less than about 6 millibars, such as about 5 millibars or less, about 4.5 millibars or less, about 4 millibars or less, about 3.5 millibars or less, about 3 millibars or less, or even about 2.5 millibars or less (e.g., about 1.5-6 millibars, such as about 1.75-4.25 millibars, such as about 1.8-5.4 millibars, about 1.9-3.8 millibars, about 1.8-3.6 millibars, about 1.75-3.5 millibars, about 1.5-4.5 millibars, or about 1.5-3 millibars).

In certain aspects, the methods herein comprise application of two or more, three or more, four or more, or five or more vacuum conditions. In some aspects, vacuum conditions are applied as a continuous gradient of vacuum conditions. A gradient of vacuum conditions is a set of two or more vacuum conditions (e.g., a first and a second condition), one condition being higher and one condition being lower than the other, separated by at least one vacuum condition in between, wherein the vacuum condition is continuously modified from the first to the second condition, and, accordingly, any vacuum condition between the first and second conditions are also applied (such that a slope of conditions between the first and second vacuum conditions is created). In certain aspects, any first and second vacuum pressures applied as part of the method vary by at least 5× (e.g., one is at least five times the other). In some aspects, an amount of extracted material-associated water released from the material is measured at predetermined intervals across such a gradient of vacuum conditions, such as for example every change of about 0.5 millibars, change of about 1 millibar, change of about 2 millibars, change of about 5 millibars, or e.g., such as for example change of every about 10 millibars. In some aspects, an amount of extracted material-associated water released from the material is measured continuously across a gradient of vacuum conditions. According to some embodiments, detectibly or significantly different data or clusters of data are obtained when a gradient of vacuum pressures are applied from that obtained by the utilization of at least two distinct pressures without a gradient in between. In some aspects, such use of a gradient of pressures may yield different peak TAL release points which otherwise would not be visible. In some aspects, such identifiable spikes or increases in TAL at specific vacuum pressures can identify different TAL characteristics or material characteristics which would not be revealed if such measurements were not taken at such specific vacuum pressures, and, accordingly, such a technique may yield further insights into the character of the material, such as, e.g., a degree of oil- or water-wettability.

Environmental Conditions/Selected Conditions

Samples can be exposed to various immediate environmental conditions which impact the amount of any one or more TALs released. As used in this context, an environmental condition is a select condition defining the immediate area surrounding a sample, such as, e.g., a chemical or composition in which a sample can be submersed. In aspects, an environmental condition is a SCETAL.

In some aspects, samples can be exposed to chemicals/compositions which enhance or replace the extraction of TALs accomplished by other conditions such as, e.g., vacuum pressures. In aspects, exposure to one or more selected conditions comprises exposure to a chemical or composition having properties which enhance the release of one or more TALs, such as water or oil, from a material.

Chemical extraction of water from the sample can be accomplished by any known such means in the art, such a chemical extraction method requiring that the chemicals used in the method do not create nor destroy nor alter in any appreciable manner an EEW or RRW to be analyzed (e.g., by use of a desiccant such as Drierite™ brand products).

In some aspects, a selected condition-extracting material can be referred to as an extraction-modulating substance. Extraction-modulating substances demonstrating a particularly fast-acting effect of extracting a TAL from a material may be referred to as a fast-acting tightly-associated liquid (TAL)-releasing substance (FATALRS). In some aspects, an extraction-modulating substance and/or FATALRS can be selected from a group comprising but not limited to one or more of a compound or composition characterizable as having a/an surfactant, salt, polyphenolic, acid, base, organic, inorganic, polar, non-polar, oxidizing, or reducing nature, or any combination of any or all thereof.

In some aspects, a material can be exposed to an extraction-modulating substance, e.g., a surfactant or a salt, prior to any physical disruption which may be applied to the material. In some aspects, a material can be exposed to such an extraction-modulating substance after any physical disruption which may be applied to the material.

In some aspects, an extraction-modulating substance and/or FATALRS can be a surfactant (such as an ionic (including anionic or cationic surfactants) or non-ionic surfactants, such as, e.g., (a) non-ionic surfactants such as ethoxylated and alkoxylated fatty acids, ethoxylated amines, ethoxylated alcohol, alkyl and nonyl-phenol ethoxylates, ethoxylated sorbitan esters, or castor oil ethoxylate; (b) ionic surfactants, e.g., as sodium lauryl sulfate, sodium laureth sulfate, ammonium lauryl sulfate, ammonium laureth sulfate, sodium stearate, or potassium cocoate; or (c) both (a) and (c).

In some aspects, an extraction-modulating substance and/or FATALRS can be a salt, e.g., an organic or inorganic, strong, or weak salt, and can include alkali salts, acid salts, or neutral salts.

In some aspects, an extraction-modulating substance and/or FATALRS can be or comprise a polyphenolic compound(s), e.g., chlorogenic acid (CGA), one or more diterpenes, or trans-cinnamic acids (e.g., caffeic, ferulic and p-coumaric acids). In aspects an extraction-modulating substance or FATALRS can comprise one or more of caffeine, trigonelline, fiber (soluble or insoluble), protein, one or more lipids, minerals, and/or melanoidins. In some aspects, an extraction-modulating substance and/or FATALRS can share one or more components with those found in coffee.

According to certain specific facets, the oil-wetting nature of a material can be quickly assessed by exposing a sample to an effective amount of one or more FATALRSs, or to an effective amount of one or more ingredients in TAL-extracting/TAL-releasing compounds or compositions in a FATALRS. In some aspects, the material can be exposed to one or more of a FATALRS (e.g., to a panel of FATALRSs), whereby the exposure results in the detectible release of at least a portion of a TAL, if present in the material. In some aspects, in such a scenario, a TAL may be a TAF as alternatively described herein. In aspects, the TAL may be a gas, e.g., a volatile in a gaseous state, such as one or more volatile hydrocarbons.

In aspects, a material can be any material described herein. In certain embodiments, the material is a petroleum drill cutting. In aspects evaluation or detection of released TAL(s) is performed visually or also or alternatively may be performed using one or more instruments, such measurement by instrumentation in aspects being part of an automated detection system.

According to certain aspects, any one or more FATALRSs can be provided for assessing the presence of one or more TALs of a material. In one aspect, a single FATALRS is provided. In alternative aspects, two or more, such as a panel of about 5, about 10, about 20, about 30, about 40, about 50, about 60, about 70, about 80, about 90, or about 100 or even more FATALRSs can be provided (e.g., one could provide a panel of FATALRSs using an multi-well plate, such as, e.g., an ELISA plate or microtiter plate having a plurality of wells, e.g., 96 wells each comprising an FATALRS). In aspects, a baseline measurement of one or more characteristics of the FATALRSs can be provided, such as a baseline measurement of visual appearance, concentration, color, viscosity, oil content, light absorbance, light reflectance, osmolality or osmolarity, uniformity of mixing, or an element related to petroleum oil content (e.g., is capable of changing if petroleum oil is added) or the like using any known measurement tool or techniques for analyzing the same. In aspects, one or more samples of a material can be added to one or more FATALRSs and allowed to remain in contact for a period of time, allowing TAL within the material an opportunity to be extracted by the FATALRS.

In aspects, such a time period can be, e.g., less than about 3 hours, such as less than about 2.5 hours, less than about 2 hours, less than about 1.5 hours, or even less such as less than about 1 hour (e.g., less than 30 minutes or 15 minutes). After the passing of a given period of time, the material can optionally be removed, and the FATALRS reanalyzed.

In aspects, detectible or significant changes from the baseline measurements and the final measurement of the selected characteristic(s) in one or more FATALRS can indicate the release of one or more TALs from the material. In aspects, the material is a petroleum drill cutting(s) and the TAL is oil. In aspects, the extraction of oil detected by application of this method is indicative of the oil-wetting nature of such cuttings, which can indicate the oil-wetting nature of the rock from which it was sampled, which can further indicate the possible current or past presence of a petroleum-producing location or the high probability of such a location being a part of a petroleum producing system within the geological area.

In some aspects, the characterization of a FATALRS at baseline and after having been exposed to a material can comprise use of visual inspection. In aspects, visual inspection comprises use of a microscope. In some aspects, evaluation can utilize instrumentation, which can comprise use of technology(ies) selected from a group comprising but not limited to microscopy, spectroscopy, spectrophotometry, colorimetry, photometry, viscometry, and osmometry.

In some aspects, a TAL released by a release-enhancing substance, such as a FATALRS, can be such that it separates from the FATALRS into which it is released, creating a layer of TAL which can be measured. In some aspects, for example, the TAL is an oil, and the amount of such an oil can be calculated based upon the size (e.g., volume) of the layer or the size (e.g., volume) of a film of oil created on top of the substance upon its release from a material in contact with the substance.

In one embodiment, a volume of a release-enhancing substance can be provided. In one aspect the substance is a FATALRS. In aspects a plurality of release-enhancing substances, e.g., FATALRSs, can be provided as a panel. For the sake of simplicity this exemplary concept of measuring oil content of a material will be provided using language describing a single FATALRS capable of releasing an oil from a material.

In one embodiment, a volume of a FATALRS can be maintained within such a confined space that the amount of TAL released by a material placed in contact with it is sufficient to cover the complete exposed surface area of the FATALRS. In aspects, such a surface area can be known; e.g., for example, a FATALRS can be placed in a well of a microtiter plate, the area of the surface of the FATALRS within the well being measurable/known. In aspects, a material comprising one or more oils can be put into contact with the FATALRS, e.g., added to the well. Prior to contact, the FATALRS can comprise no layer of oil. In aspects, upon contacting the FATALRS, the material can begin to release oil. In aspects, after an established period of time, the thickness of any layer of oil created in the FATALRS can be measured. This could be established, for example, using techniques such as microscopy (obtaining an image of a cross section of the well and its contents and observing any oil layer on the top of the FATALRS and applying automated or manual methods of measuring the same), light reflection or absorbance (identifying which depths of the well have particular light reflection or absorbance characteristics), or similar or equivalent techniques. Knowing the surface area of the well and knowing the thickness of the oil layer produced, the amount of oil extracted from the material by the FATALRS can be determined.

In an alternative aspect, an amount of an oil released from a material placed into contact with an FATALRS capable of releasing the oil can be insufficient to cover a complete surface are of a FATALRS with which it makes contact. In such aspects, the oil can create what might be described as an oil slick, or an area of oil floating within the surface area of the FATALRS. In aspects, the area of such a slick can be measured and from that, the volume of the slick mathematically derived.

In one aspect, upon placing a material in contact with an FATALRS, a video recording can be taken over the course of an established period of time, during which the video can record the development and growth of such a film of oil. In another aspect, after a given period of time a photograph of the film could be taken. In aspects, application of a mathematical analysis of the video, or also or alternatively a mathematical analysis of the photograph, could, utilizing the known average thickness of oil molecules, derive the volume of the oil expelled from the material. This is based on the fact that the oil will create a monolayer of oil molecules upon the FATALRS if possible, only creating layers of molecules if forced to based on spatial confinement (as would be the case in the preceding example). Knowing the average thickness of a molecule of oil released by the material, one can, in aspects, manually or in an automated fashion, calculate the volume of oil released by the material.

Knowing the volume of material placed within the FATALRS, one can determine the percent composition of the material comprising oil, which could further be applied in a calculation of the volume of oil held within an oil-wetting rock. For example, if it were determined that a cuttings sample comprised 5% oil, it could be extrapolated that the rock from which it was obtained comprised 5% oil, and if the area comprising the particular rock from which the sample was taken is known, the total volume of oil held within an oil wetting rock may be ascertained.

In certain aspects, the invention provides a method of screening for FATALRSs for use in such an assay as described above. In some aspects, the invention provides a method of screening for fast-acting tightly-associated liquid (TAL)-releasing substances ("FATALRSs") capable of releasing a visually detectable amount of TAL from a material within a given period by (a) providing a panel of at two potential FATALRSs, each varying from one another based upon one or more chemical properties, concentration, or both, for which one or more initial ("baseline") characteristic is known; (b) obtaining a sufficient amount of a material; (c) combining a sample of the material with each of the potential FATALRSs of the panel; and (d) measuring the change in the at least one baseline characteristic of the potential FATALRSs. In aspects, potential FATALRSs screened are selected from a group comprising substances having a polyphenolic, saline, surfactant, acid, base, organic, inorganic, polar, non-polar, oxidizing, or reducing nature (e.g., alkane, alkene, alkyne, alkyl halide, alcohol, ether, amine, benzene ring, aldehyde, ketone, carboxylic acid, carboxylic derivative) or any combination of any or all thereof. In aspects, the given time period is less than about 3 hours, less than about 2 hours, or less than about 1 hour.

In certain aspects, methods utilizing FATALRSs can comprise use of one or more indicators. Such an indicator may be used to indicate suitable FATALRSs in an FATALRS screening assay or may be used to indicate the extraction of TAL from a material in an established FATALRS assay, e.g., by color, fluorescence, or other detectible change in the FATALRS if it releases a TAL from the material. In aspects, such an indicator may be capable of indicating the amount of a TAL released. For example, in some aspects use of an indicator providing a detectable change in one or more characteristics when a specified condition changes can be variably changed such than an amount of indicator change (e.g., as a simple example, a degree of color change) is indicative of an amount of TAL released. In aspects, an indicator may simply indicate that TAL has been released, such that when used in a screening assay it can aid in the identification of a suitable FATALRS or when used in assessing one or more materials, it can aid in identifying material releasing a TAL, and, in aspects, accordingly aid in the characterization of the material, e.g., identify the material as oil-wet.

According to certain aspects, one or more changes in one or more FATALRSs (or in an indicator if utilized) after receiving the material is an increased content of oil. In aspects, a detectible or significant increase in the content of oil of a substance after having contacted the material is indicative of the material releasing oil and indicative of the oil-wetting nature of the material.

In some aspects, an extraction-modulating substance and/or FATALRS is an aqueous solution comprising about 0.1-1.5% of one or more compounds such as those described above, e.g., comprising about 0.1-1.5% of one or more polyphenolic compounds. In some aspects, the water content of the FATALRS is at least about 80%.

Physical Disruption

In some respects, physical disruption is a condition which can be applied to a material. As described previously, in some facets physical disruption can be applied before, after, or in between application of one or more other conditions, such as, e.g., a vacuum condition. In some aspects, physical disruption releases RRF/RRL/RRW from a material which would not otherwise be released under other one or more conditions. In aspects, the RRW released upon physical disruption of a material (RRW-PD) can alone or in combination with other TAL measurements or calculations thereof be informative about the wettability characteristics of a material.

In some aspects, the methods described herein comprise no physical disruption of at least a portion of the material. In some aspects, some, most, generally all, or all of the physical integrity of the sample is maintained in applying one or more methods of the invention.

In some aspects, the application of one or more extraction methods suitable for extracting either or both of an EEW or RRW can be accompanied (typically preceded) by a physical disruption of the sample. Such a physical disruption can be any disruption capable of causing or promoting release of sample water form for analysis. According to embodiments, the mechanical disruption of a sample typically does not compromise the amount of water being extracted. In some embodiments, such physical disruption is a grinding, crushing, or otherwise breaking apart of the solids of the sample. Such physical disruption, as well as such other extraction methods, such as for example the application of a vacuum pressure, has been described in detail in my earlier applications and patents previously referenced within this document.

In some aspects, physical disruption is accomplished by crushing a material held within a sealed container, such crushing occurring without incurring any substantial loss of volatiles, including water, from the material prior to measurement. In some aspects, any amount of RRW-PD released from a material after physical disruption increases the total amount of extracted material-associated water released from the material over that of the sum of EEW and RRW obtained without physical disruption.

According to certain aspects as previously described, wherein co-located samples are analyzed, one set of samples may be subjected to physical disruption while another may not, and differences in the results between the two samples or sample sets may identify an oil-wet nature of the material. Similarly, as also previously described, in some aspects, a set of sealed-at-the-well samples can undergo a first analysis according to a method described herein, then allowed to dry or be subjected to one or more artificial aging methods, then subjected to physical disruption and reanalyzed, the differences in the analyses being capable of identifying an oil-wet nature of the material.

According to specific embodiments, a collection of samples is subjected to physical disruption after the collection of EEW and RRW, releasing RRW-PD, and wherein, either (a) within the collection of samples, results of water analysis from one or more groups of samples in the collection vary from the results of the same analysis performed on one or more other groups of samples in the collection, (b) within the collection of samples, results from petroleum-related volatiles analysis from one or more groups of samples in the collection vary from the results of the same analysis performed on one or more other groups of samples in the collection, or (c) both (a) and (b), such that the variation in the groups of samples identifies differences in oil- and/or water-wettability in the samples. In certain facets, a total oil measurement as indicated by the analysis of rock volatiles in one group of samples that is greater in samples having undergone physical disruption that in samples not having undergone physical disruption is indicative of such a group of samples being oil wetting in their nature.

Analysis of TAL Content

The analysis of the relationship between classes of TAL (s), such as EEW and either RRW and/or combined water measured by the methods described herein can provide useful information in directing petroleum production or exploration operations and assessing material characteristics. The analysis of the relationship between the EEW and RRW can be performed by any suitable methods, which may be a manual method or a computer-implemented method (e.g., by programming an algorithm for any of the relationships exemplified in the listed aspects of the invention contained herein). Such an analysis can be performed in an automated manner, e.g. performed immediately and automatically by, for example, a computer program, upon receipt of the pieces of data required for the analysis, or can be initiated on an as-needed or intentionally triggered basis.

According to certain aspects of the invention, the extraction methods as described herein can yield one or more water samples suitable for analysis via mass spectrometry. In some aspects, such one or more samples are analyzed via a suitable method using a mass spectrophotometer. In many aspects, however, the extracted water is not subjected to mass spectrometry. In some aspects, water is subjected to assessment/evaluation/indirect measurement using capacitance manometry (use of a capacitance manometer) as described previously.

In some aspects, the methods described herein can incorporate cryogenic mass spectrometry volatiles analysis ("CMSVA") prior to performing certain steps of the present method. In some aspects, CMSVA analysis can be applied prior to measuring the EEW by a first analysis, prior to measuring the RRW by a second analysis, and prior to evaluating the relationship between the first measurement and the second measurement.

As noted, it may be advantageous in certain embodiments to analyze any one or more extracted water sample, e.g. an EEW or a RRW via a method which is not mass spectrometric (e.g. not analyzed by mass spectrometry). In some aspects, the first measurement, e.g. the measurement of EEW is not obtained by mass spectrometry, the second measurement, e.g. the measurement of RRW is not obtained by mass spectrometry, and/or neither the first measurement nor the second measurement is obtained by mass spectrometry. This can be advantageous in circumstances wherein facilitating onsite (e.g. at the drill site) analysis is desired as housing a mass spectrometer at a drill site can be difficult to facilitate. Moreover, as reported elsewhere herein, mass spectrometry methods often cannot be suitably applied to extracted water from relevant samples given the abundance of even sample water in such materials and the impact thereof on the functioning of most mass spectrometers.

In embodiments wherein the method comprises CMSVA analysis, the sample obtained for analysis can be housed in a sealed container. The sealed container can be a container capable of protecting the sample from DOS contamination and/or water loss or gain and may also or alternatively be suitable for use in CMSVA analysis. According to certain aspects, the cryogenic mass spectrometry analysis is performed on the sealed sample, that is, on the sealed sample within the container. According to certain embodiments, the container is a crushable container capable of withstanding a physical disruption of the sample contained inside without DOS releasing volatiles released by the physical disruption. In some aspects, the container is a crushable container, and the method comprises crushing the sample, and the container in which it is held, prior to performing CMSVA, without any substantial loss of volatiles.

Exemplary Applications

It should be understood that while the focus of this disclosure is on the application of the invention to geological endeavors, the invention described herein can be applied to any endeavor for which the invention is suitable or advantageous. The scope of the invention should not be interpreted as being limited only to those applications and endeavors described herein.

Geological Applications—E.g., Petroleum Exploration & Production

According to certain embodiments, the method of the present invention comprises directing petroleum production or exploration operations. In some aspects, the methods described here can be of particular interest as a tool in geological locations challenged by existing well logging technologies, such as for example but not limited to freshwater plays and low visibility plays. However, the methods herein can be applied to areas/locations that more traditional well logging tools can also be employed, as an alternative tool or also or alternatively as an added tool. In certain embodiments, the method of the present invention comprises directing petroleum production or exploration operations based on the relationship between the first measurement of the present methods (e.g., the measurement of the amount of EEW in a sample), and the second measurement of the present methods, e.g., the measurement of the amount of RRW and/or the combined water content in a sample. In some aspects, the EEW alone, or the combined water alone, is capable of revealing the oil-wetting characteristics of a sample or set of samples, or, further, indicate the likelihood of the sample or set of samples being associated with a petroleum producing system.

In some aspects, the total amount of EEW measured, the sum of EEW and RRW measured, the relationship between EEW and RRW, or any combination of any or all thereof derived from the application of the methods described herein are used to direct real time petroleum drilling operations. In some aspects, use of any indicator of oil-wettability obtained from the application of methods described herein are used to direct petroleum drilling operations in real time or to inform operational activity and/or decision making related to a petroleum prospecting, drilling, or extraction operation within a geological area.

The data collected from the methods of the present invention can be used alone or in conjunction with other well site data to inform drilling operations. In some aspects, the analysis of a first measurement (e.g. the amount of EEW in one or more samples), analysis of a second measurement (e.g. the amount of RRW in one or more samples), analysis or calculation of the combined water, or the relationship between any such two measurements, obtained by the present methods is compared to information obtained through other analytical methods performed on the sample (or on co-located material), such as for example CMSVA, gamma ray analysis, fluid inclusion analysis, conventional well logging analysis (e.g., well log Sw), conductance data (e.g., wireline resistivity log data), or other similar or equivalent analysis or common well-site analysis techniques and methods known in the art or any combination of any or all thereof to provide further insight into the petrochemical status of drill site from which the sample(s) was/were collected.

The collection, analysis, and reporting of such information can be performed manually or can be facilitated by the use of computer equipment using standard techniques but encompassing the unique algorithms of the methods provided herein. Methods of the invention comprise, e.g., relaying such information over distances by way of the internet, wireless signals (e.g., Bluetooth or Wi-fi signals), and the storage of such information, e.g., in databases of similar information, which can further include other petrophysical data and/or actual petroleum production data associated with a site, similar sites, a collection of sites, a region, etc.

In aspects, wettability characteristics of the material from an oil well as determined by the application of the methods herein can be used to identify higher probabilities of the oil well comprising a pay zone. In certain aspects, application of the method to multiple samples is capable of identifying a pay zone within an oil well, within a geological area or geological formation, or both. In some aspects, methods of producing or extracting oil from an oil accumulation, e.g., a method of secondary recovery of oil, is/are selected at least in part based upon the wettability properties of the rock in which the well is drilled as identified by the application of the method. According to certain facets, decision(s) to abort or maintain operation within a geographical area is/are made at least in part based on the wettability characteristics of rock within the area as identified by the application of the method. In some aspects, a material is from an inactive well and the method comprises using the information to start new operations in, from, or around the inactive or non-producing well.

Non-Geological Materials

In some aspects, methods are applied to non-geologic/non-petroleum-related material. I have now invented methods of assessing materials outside of such domains, such as determining the wettability of such materials, including artificial materials and biological materials. Accordingly, in some aspects the invention can be applied to evaluate whether a material is suitable for a particular application. In some aspects, evaluation of a material may be conducted as part of quality control measures for a material or to otherwise assess whether a material meets a specific standard related to wettability.

In some aspects, the methods herein can be applied to determining wettability of electronic devices or materials used in electronics devices. This can span a diverse spectrum of materials and devices, ranging from, as examples, the water-proofing materials used in optoelectronics and high frequency microelectronics, comprising semiconductors such as indium phosphide (InP) and gallium arsenide (GaAs). Use of such materials spans lasers for telecommunications, imaging, photodetectors, sensors, and solar cells ("Controlling and modelling the wetting properties of III-V semiconductor surfaces using re-entrant nanostructures, Ng, Nature, 2018). Further waterproofing is important in consumer electronics such as mobile phones, computers, gaming devices, and laptops. Other exemplary materials wherein wettability characteristics have been studied include liquid metal ("Interface design for enhancing the wettability of liquid metal to polyacrylate for intrinsically soft electronics", Wu et. al., Journal of Materials, 2018), polyimides ("Surface wettability controllable polyimides by UV light irradiation for printed electronics", Tsuda, Journal of Photopolymer Science and Technology, 2016), engineered patterned surfaces of different materials ("Enhanced pool boiling of ethanol on wettability-patterned surfaces", Shen et. al., Applied Thermal Engineering, 2019 (related for electronic cooling applications)), and, e.g., graphene/graphene films ("Wettability and surface free energy of graphene films", Wang et. a., Langmuir, 2009, among others.

Wang 2009 (above), discussing the wettability of graphene films, is a good example of a material, graphene, having found use in a number of fields, including electronics and medical instrumentation (e.g., see also "Temperature-tunable wettability on a bioinspired structured graphene surface for fog collection and unidirectional transport", Song, Nanoscale, 2018). Wetting can be important in the field of medical devices as it can, for example, impact the bonding or adherence of two materials as in, e.g., surgical adhesives. Further examples of materials utilized in medical devices wherein wettability is important include porous polydimethylsiloxane (Wettability of porous polydimethylsiloxane surface: morphology study", Khorasani et. al., Applied Surface Science, 2005), nanofiber membranes ("Controllable broadband optical transparence and wettability switching of temperature-activated solid/liquid-infused nanofibrous membranes", Manabe, ACS 2016), bioinspired surfaces ("Bioinspired surfaces with wettability for antifouling application", Li et. al., 2019), and e.g., ceramics ("Wettability and surface free energy of polarized ceramic biomaterials", Nakamura, Biomedical Materials, 2015), among others.

In aspects, wettability is important in building materials, as such characteristics impact performance and longevity. Appropriate wettability characteristics of a material can slow down material aging, improve antifouling properties, and enhance the ease of washing or cleaning such materials. Examples include material wettability studies include analysis of such materials as wood and modified woods ("Aspects on wettability and surface composition of modified wood", Bryne, DiVAportal.org, 2008), automobile and architectural glass incorporating TiO2 ("Photocatalytic activity and photo-induced wettability conversion of TiO2 thin film prepared by sol-gel process on a soda-lime glass", Watanabe, Journal of Sol-Gel Science and Technology, 2000), and, e.g., cement ("Bonding-strengthening technology in coalbed cementing through wettability improvement", Wang et. al., Natural Gas Industry, 2018), among others.

Wettability characteristics are also important in the development of pharmaceuticals, as such characteristics impact product performance. Wettability characteristics of materials impact manufacturing processes, properties of final products, and interactions between materials during the formulation and manufacture process. Examples of applications of wettability within the field of pharmaceuticals include application to powders ("Correlation between wettability and dissolution rate of pharmaceutical powders", Lippold et. al., International Journal of Pharmaceutics, 1996), solids ("Wettability of pharmaceutical solids: its measurement and influence on wet granulation", Zhang, Colloids and Surfaces, 2002), and, e.g., polymer membranes ("Continuous purification of active pharmaceutical ingredients utilizing polymer membrane surface wettability", Imbrogno, Royal Society of Chemistry, Chem. Commun., 2018), among others.

Another field where wettability characteristic determination has found relevance is in the arena of biological materials. Wettability characteristics of materials is important as it can impact response to an implanted material, and affect absorption of compounds and compositions, as discussed in "Role of water wettability, water transport, and adhesion in vision", Holly, Journal of adhesion science and technology, 1993; "Role of surface charge on wettability on early stage mineralization and bone cell-materials interactions of polarized hydroxyapatite", Bodhak, Acta Biomaterialia, 2009; "Contact angles and wettability of human skin", Schott, Journal of Pharmaceutical Sciences, 1971.

Contact angle is a common method of measuring wettability; however, it is not always best suited for certain applications; see for example, "Water contact angle is not a good predictor of biological responses to materials". In aspects, methods of assessing wettability herein are associated with detectably or significantly better assessment of wettability of materials than contact angle wettability assessments. In aspects, both contact angle assessments and assessments through TAL measurements are performed and compared in evaluating wettability characteristics of a material.

Devices

In certain aspects, the invention described herein is a device or system for analyzing likelihood of association of petroleum with a geologic formation comprising (a) means for analyzing EEW, (b) means for analyzing RRW, (c) means for summing and/or comparing EEW to RRW and/or total water, and (d) means for displaying results of an analysis. In aspects, the invention provides a method of analyzing a group of samples from a geologic formation comprising (a) step for measuring EEW, (b) step for measuring RRW, (c) step for summing EEW and RRW and/or comparing EEW to RRW and/or total water, and (d) step for relaying results of a comparison.

Still further yet, in aspects, the invention provides devices and/or systems for performing any of the herein-described analyses. In one exemplary aspect the invention provides, e.g., an analytical device or system for analyzing samples obtained from a geologic formation comprising (a) component for receiving a sample, (b) (i) an analyzer capable of analyzing a first aliquot of a target analyte such as EEW from a sample after the application of a first condition to the sample, (ii) an analyzer capable of analyzing a second aliquot of target analyte (such as RRW) from a sample after the application of at least a second condition to the sample, (iii) optionally an analyzer capable of analyzing a third aliquot of target analyte (such as an SRRW such as RRW-PD) from a sample after the application of a third condition to the sample, or (iv) an analyzer capable of analyzing aliquots collected after each application of a plurality of conditions, such as indirectly via use of a capacitance manometer; (b) a processor for computing the sum and/or relationship between any two or more aliquots or calculations based on aliquots of target analyte measured, e.g., the relationship between EEW and RRW, and (c) a display for displaying results of any aliquot analysis and the results of any calculations made therefrom, such as the relationship between EEW and RRW. Specific details for all of these various aspects are provided in the listed aspects of the invention enclosed herein.

In aspects, the invention herein provides a device or system comprising software. In aspects, software can be used for operating the device and/or system in which a device may be one component, controlling any one or more components of a device or system, recording results of analysis, reporting results after analysis, storing results after analysis, after reporting, or any or all thereof, or any other purpose related to application of the methods described herein. In aspects, the device or system comprises software capable of directing the capable of capturing one or more results generated by the device. In aspects, the device or system device/system can be capable of receiving input, either manually or via an automated fashion, such as results from other types of analysis. In aspects software of the device/system can capture one or more results inputted or received by an interface (e.g., a manual interface or an interface with one or more other devices or systems from which data can be received), software capable of performing calculations using device-collected or device-received (e.g., by external receipt or input) data or both, and communicating results. In aspects the device or system comprises a mass spectrometer. In further aspects, the device comprises a capacitance manometer. In aspects, the device and/or system comprises both a mass spectrometer and a capacitance manometer, and software to perform any of the functions herein described. In aspects, the device or system comprises components comprising communicating results locally (e.g., on/within the device or system where the software resides, via, e.g., a monitor or the like), remotely, e.g., via a network or the web, or also or alternatively by wireless communication such as a Bluetooth connection to one or more locations, devices, or systems, located a distance away. In certain aspects, the device or system can display the results of analyses or results of data processing. In aspects results can be displayed on a locally positioned monitor. In aspects results can be shared electronically or via wireless connection to a secondary location. In aspects results can be shared with a central location compiling results from one or more other analytical methods and a compilation and/or comparison of such results can be displayed in such a location. In aspects, results can be displayed via a receiving device directly related to a drilling operation, such as, for example, a drilling rig, or within a facility close to a drilling operation such as a mud shack.

In certain aspects, the system or device can comprise software and processing capability for comparing results received from one or more other analytical methods to results of application of the analytical methods described herein, such as comparing results to traditional well log data.

In certain aspects, the device or system comprises a mechanism or component for receiving one or more samples. In aspects, the samples can be received in a container. In some aspects, the container can be a sealed container which remains effectively sealed unless specifically unsealed as a step in the analysis (e.g., such as when punctured by a needle to extract released material).

In some aspects, the device or system optionally comprises a component capable of physically disrupting a sample and/or a container containing a sample. In aspects, such a physical disruption promotes the release of one or more TALs.

In some aspects, the device or system comprises an element for applying vacuum pressure. In aspects, a vacuum component is present capable of applying one or more vacuum pressures to promote the extraction of one or more TALs.

In certain aspects, the device or system further comprises an extractor capable of extracting a first aliquot upon the application of a first condition, an extractor capable of extracting a second aliquot upon the application of a second condition, or an extractor capable of extracting a plurality of aliquots upon each of the applications of a plurality of conditions.

In certain aspects, the device or system comprises a mechanism for capturing released TAL. In one aspect, such a mechanism is a media trap. In aspects, a device or system can comprise a plurality of traps, each capable of capturing one or more TALs, and in some aspects each trap capable of capturing a different one or more TALs than another trap. In aspects, a media trap captures and concentrates an aliquot of TAL released by application of one or more conditions. In some aspects, the trap is a freezing trap, mechanism, or media. In certain aspects, the trap is a liquid nitrogen trap or a dry ice trap. In aspects, the trap is a cryogenic trap.

In aspects, the device comprises an element for cooling a sample, such as, e.g., components for mechanical refrigeration or cooling (e.g., a powered refrigerator or a Kelvinator or other cryogenic device).

In some aspects, the device or system comprises an element for heating a sample. In some aspects, heat is applied to release one or more TALs from one or more traps such as a cryogenic trap.

According to some facets, the device or system is incorporated into or otherwise in communication with a device or system configured for performing cryogenic mass spectrometry volatiles analysis of samples. In some aspects, the device or system comprises a mass spectrometer. In some aspects, the device comprises a capacitance manometer. In aspects a capacitance manometer is used to assess the content (e.g., to indirectly measure) an amount of one or more TALs, such as EEW or RRW, via measurement of total pressure. In some aspects, analysis of an EEW, RRW, or both can be accomplished by means other than mass spectrometry or capacitance manometry, such as for example use of tensiometry, volumetric sensors, moisture sensors, and other types of technology known in the art. In some aspects, the invention provides a method for using capacitance manometry to identify the wettability characteristics of a material comprising subjecting an analyzable amount of a material to one or more environments sufficient to cause the release of a detectable amount of water, if present. In aspects, the one or more environments can be selected from the group of environments comprising an environment characterizable as being under vacuum pressure, an environment characterizable as being saline, an/or an environment characterizable as having surfactant properties. In aspects, such released water is captured, and the amount of water is assessed via use of a capacitance manometer. In aspects, the capacitance manometer measures total pressure, such a pressure being caused by the evaporation of condensable volatiles, wherein at least about 95%, at least about 96%, at least about 97%, at least about 98%, at least about 99%, at least about 99.5%, or at least about 99.5% of the pressure from the evaporating condensable volatiles is caused by water release. In aspects, the wettability properties of the material can be characterized based on the measurement of the extracted material-associated water. In certain facets, the invention provides a method of using capacitance manometry to identify the wettability characteristics of an area of rock comprising analyzing the water content of rock cuttings or core samples taken therefrom.

In certain aspects, a device or system comprises a protection component or system for isolating samples from environmental exposure to water while in the device or system. In aspects, the device or system lacks any mass spectrometer, lacks any liquid nitrogen container, or lacks both.

In some aspects, a device or system can be any device or system described in my prior work, such as the devices and systems disclosed in international application number PCT/US2017/065921 (published as WO/2018/111945).

According to certain aspects, the invention provides a device for assessing the wettability characteristics of a material via use of FATALRSs to release one or more TALs. In some aspects, the invention provides an analytical device or system for analyzing the tightly-associated liquid characteristics of a material, comprising (a) a component for receiving one or more samples of material, (b) (i) an analyzer capable of establishing a baseline value for one or characteristics related to one or more FATALRS(s), and (ii) an analyzer capable of detecting the change in one or more characteristics of one or more FATALRS(s); wherein (i) and (ii) can optionally be the same analyzer; (b) a processor for analyzing the change in one or more characteristics related to the FATALRS(s) between the baseline value and a final value; and (c) a display for displaying results of any direct analysis and the results of any processed data resulting therefrom.

In some aspects, such a device can receive a plurality of samples of a material, so as to facilitate the screening of multiple samples at a time. In some aspects, such an analysis may be compared to a high-throughput screening assay or assays wherein multi-well plates or an array of sample or test reagents are used to make multiple assessments in a single analysis. In some aspects, such a device or system can comprise a means of dispensing the one or more FATALR(s) into the one or more samples of material, such as automated pipettors, dispensation tubes accessing stored material, syringes holding sampled material, or other dispensation mechanisms utilized in analytical techniques and technologies wherein one or more samples or reagents are dispensed in an automated fashion. In some aspects, samples may be manually added to such a device or system. In certain aspects, the device or system can comprise a means of controlled mixing of the combined FATALRS(s) and sample(s) of material. In aspects, the device can comprise, e.g., a stir plate and associated mixing bars, one or more rod mixers, a shaker or rocking plate or table providing a consistent vibration, rocking or rotational movement causing stirring, or other stirring mechanisms utilized in analytical techniques and technologies wherein two or more components are mixed.

In certain aspects, the device or system can comprise a component capable of tracking a programmable or established time period or the passage of time, such that each application of an analytical method is performed using a consistent test period. In certain aspects, a manually set timer can be utilized. In certain aspects, the device or system comprises a programmable timer, clock, or other timekeeping instrument.

In certain aspects, the device or system can comprise a means of detecting a characteristic of a FATALRS(s) prior to the addition of a material and again after the addition of a material. In certain aspects, such a characteristic can be any characteristic which changes the FATALRS if an added material contains a TAL which is released by one or more FATALRS(s). In aspects, the device or system comprises one or more detectors selected from a group of technologies comprising spectroscopy, spectrophotometry, colorimetry, photometry, viscometry, and osmometry.

According to certain specific embodiments, (a) upon the combination of one or more FATALRS(s) with one or more samples, (i) a predetermined period of time is allowed to pass; (ii) one or more detectors are applied to analyze one or more characteristics of the one or more FATALRS(s); and (iii) the results of (ii) are compared to baseline values for the one or more characteristics of the FATALRS(s); wherein any statistically significant change in the one or more characteristics from baseline is indicative of the release of a TAL from the sample. In some aspects, the device or system is capable of receiving a plurality of samples of material, and the material provided is petroleum drill cuttings, wherein the plurality of drill cutting samples are representative of the rock present at a plurality of locations across a drilled oil well, and wherein the device or system is capable of detecting differences in the characteristics of the rock based upon the TAL released from the cuttings samples analyzed by the device, wherein the TAL is oil.

In aspects, the device or system can comprise a mechanism for quantifying the size of a film floating on the surface of a liquid, e.g., a TAL film (e.g., an oil) floating on one or more FATALRSs. In certain facets, the device or system can comprise one or more photograph or video graphic components. In one aspect, the device can comprise software capable of image recognition such that it can detect an area of a TAL within an FATALRS within a video or photographic image, identify the area as that which should be measured, apply analytical rules which allow for the area to be measured, and calculating the volume of TAL released based upon one or more additional pieces of data (e.g., the thickness of an oil molecule).

In some aspects, the device or system is capable of receiving additional data about each sample, such as but not limited to a sample identifier, the location where a sample was collected, a time of collection, or the like. In aspects, such additional data, such as for example volume of any one or more samples added to the device, can be used to calculate the percent composition of the material comprising TAL (e.g., TAL content of the material). In aspects, the device or system can receive data related to a larger substance from which one or more samples were collected. In facets, the device or system comprises software capable of translating results of the analysis of one or more samples to a report which comprises one or more characterizations of the larger substance from which one or more samples were collected. In certain aspects, the device or system comprises a processor which is capable of generating a report based upon data available about each sample and the results of sample analysis, such a report in aspects identifying locations within an oil well comprising oil-wet rock.

Additional Embodiments and Principles

The invention described here provides a new, novel, and unique method that includes using water contents analyzed using multiple aliquots, to determine the locations and evaluate the quality of oil and gas reservoirs in vertical and horizontal wells from drill cuttings and core, and to also or alternatively identify oil- or water-wetting characteristics of materials including drill cuttings to evaluate the petroleum production characteristics of the location from which the samples were taken or the potential of a larger petroleum system in which it may reside.

As exemplified above, the technique has been applied to old and new cuttings and core samples. The process has been applied to samples obtained from wells drilled using Oil Based Mud (OBM) and from samples obtained from Water Based Mud (WBM) wells. Even cuttings from Air drilled wells have proven to provide useful data using this analytical technology. The process is applicable to washed and dried cuttings samples.

Sealed at the well samples can also be analyzed if following the preliminary analyses, before squeezing the sample (subjecting it to crushing), the sample is then artificially aged by direct pumping on the sample (to remove formation water and production water) and discarding of vapors outside the apparatus, followed by isolating the sample, crushing the sample, and analyzing the volatiles released from the samples. Suitable conditions and details concerning several suitable exemplary aspects of the procedure are described in my previously filed patent applications and patents. Such techniques can also be applied to cores, including aged cores, or even new core samples, taken and sealed at the well.

An exemplary technique for washed and dried cuttings samples, and for old core samples, where "old" means core samples not sealed at the well regardless of their age, is as follows. A cuttings sample is obtained from a drilling well using normal practices routinely employed of allowing the cuttings sample to exit the flow line into the possum below and then to transit the shaker table to be dropped into a sample trough from which a sample is taken on a regular basis, usually ever 10' to 90' depending on the well. A somewhat superior cuttings sample can be obtained, as described in our previous submissions, by not allowing the sample to traverse across the shaker table. Instead, the cuttings sample is caught using a sieve-like device or device serving as a sieve, such as that similar or equivalent to a kitchen strainer, from the mud after it is discharged from the flow line and before it enters the possum belly. The sample is then usually washed and dried. Drying using high heat may compromise the sample. As such, air drying may be advantageous in some aspects. Washing using soap, detergents, solvents, or diesel is not recommended. A simple water-based wash is typically better. Alternatively, the cleaning step may simply comprise cleaning cuttings using mild brushing/abrasion, such as using a toothbrush or other similar device. Such dry-cleaning methods may be very advantageous where salt makes up part of the geologic formation, as washing such samples in water removes an actual part of the rock by the dissolution of the salt.

The washed and dried cuttings samples, or the samples of core, are typically loaded into plastic tubes until the tubes are completely filled. The tubes are shaken and tapped on hard surfaces to try to get the cuttings to settle and pack the tube as fully as possible. Not including pore spaces between the pieces of cuttings or core, our sample tubes hold about 400 micro-liters of rock.

The filled plastic sample tubes are loaded into metal (e.g., brass) tubes that are sealed at the bottom. Cotton is put over the sample to prevent rock dust from entering the instrument. A nitrile cap is put on top of the brass tube to hermetically seal the sample. A tight-fitting aluminum ring can be squeezed onto the nitrile cap to make a more perfect seal. The aluminum ring is usually used primarily for sealed at the well samples.

For washed and dried cuttings samples, and old core samples, the analyses typically proceed by loading the ready to be analyzed sample tube onto an autosampler. A needle is lowered into the autosampler through the nitrile cap making a vacuum-tight seal. The sample is crushed with an air piston driven ram. A valve is opened to the needle allowing gas to exit the sample and enter a static vacuum volume. This reduces the pressure on the sample from atmospheric to about 20 millibars, or about $\frac{1}{50}^{th}$ of an atmosphere. Volatiles are frozen onto the liquid nitrogen (LN2) cryogenic trap ("Cryo Trap"), providing the cryogenic aspect to cryogenic mass spectrometer volatiles analysis (CMSVA). After about 7 minutes, the Cryo Trap is evacuated to hard vacuum, about $10^{-5}$ Torr, opened to the mass spectrometer, and allowed to warm and release volatiles into the mass spectrometer for analyses. The temperature range during warming goes from about −194 to −20 degrees centigrade. As the Cryo Trap warms gases are released in a generally predictable manner (expected to be according to their sublimation temperatures).

The method is believed to be advantageous, at least in part, given the different properties of water, as compared to oil, at relevant depths for modern petroleum production (typically well below surface). Oil and gas are very much prone to leaving the cuttings samples as they are brought to the surface from depths often between 5,000' to 10,000' below surface to the surface. This is because of the tendency of oil and gas to expand as pressure is reduced. For oils this is more of a problem for good quality light oils than for degraded volatile-poor degraded oils.

Water does not suffer from volume expansion as cuttings and core samples come to the surface as does oil and gas in that water is very incompressible. As such the density of water at 10,000' is like the density of water at the Earth's surface. This is in stark contrast to oil and gas which experience large volume increases, causing loss from cuttings during transport, as pressure is released during transport of cuttings to the surface.

Water is by far the most abundant volatile in most petroleum cuttings, especially cuttings sealed at or analyzed at or near a well site. It also is released from cold traps (e.g., LN2 traps) after almost all other volatiles (e.g., C4-C6 hydrocarbons).

There is so much water released from cryogenic trapping that direct analyses by the mass spectrometer usually causes the mass spectrometer to malfunction as the pressure becomes so high as to prevent ionization, transport, and separation of charged ions. In order to overcome these difficulties with mass spectrometric analyses of water we have developed an alternative method for analyzing water.

As the mass spectrometer cannot handle the pressure from all the evolved water, we have instead developed the system to transport and analyze the water using a capacitance manometer (e.g., a 0-0.1 Torr capacitance manometer) to measure total absolute pressure. The manometer is monitored and the volatiles flow is directed away from the mass spectrometer and instead passes near the capacitance manometer and is then pumped away (see the indicated point for switching analysis away from the mass spectrometer in a method combining CMSVA and the water analysis methods of this invention in a single analysis in FIG. 29).

Excellent water release curves are obtained in this manner (see FIG. 29) and analyzing water in this fashion from samples of a geologic formation, such as petroleum cuttings, is, itself, an aspect of the invention provided here. The use of total pressure measurement by capacitance manometers in the temperature region of water evolution from a water trap, such as a cooled trap, such as a Cryo Trap, as a means of obtaining quantitative water analyses from cutting, cores, and any other samples for which water analyses can be useful or necessary is still another aspect of this invention. The capacitance manometer is currently believed to be the only medium to high vacuum gauge technology that measures absolute pressure, without regard to gas species. As such data obtained from use of such a device are quantifiable for absolute amounts of water.

The invention provided herein also is generally embodied in comparing the water analyses from the same rock for the 2 separate analytical aliquots obtained under different conditions (one to obtain EEW and a second to obtain RRW). We have exemplified this by collection of a first aliquot (Aliquot 1) at about 20 millibars of pressure, and a second aliquot (Aliquot 2) at about 2 millibars of vacuum pressure.

The invention includes using the relationship of such EEW and RRW/combined water data (e.g., as plotted in curves as in the figures provided herein) to find oil pay zones that are characterized by higher Aliquot 1 water compared to Aliquot 2 water, by convergence of the water curves from each aliquot, whether or not the Aliquot 1 curve becomes greater than the Aliquot 2 curve, or both.

EXAMPLES, EXEMPLARY APPLICATIONS, DATA, AND THE FIGURES

1. FIGS. 1-29 and Associated Analysis and Data

FIGS. 1-29 provided in this disclosure show the results of the application of certain examples of the inventive methods described herein to 3 vertical wells and 1 horizontal petroleum well. (Note that a description of FIGS. 30-35 is described within the context of Examples provided to further illustrate exemplary applications of the methods described herein.)

Where not indicated, the methods described in my above-referenced previously filed, published, and patented patent applications and patents were used. In general, the analyses provided below began by loading the ready to be analyzed sample tube onto an autosampler, such as that described in connection with the devices of the above-referenced '031 patent publication. A needle was lowered into each of the sample containers loaded onto the autosampler through a nitrile cap making a vacuum-tight seal. The samples were crushed with an air piston driven ram. An associated valve was opened to the needle allowing gas to exit the sample and enter a static vacuum volume. This step reduced pressure on the sample from atmospheric to a gentle vacuum condition of about 20 millibars, or about $\frac{1}{50}$th of an atmosphere, resulting in the extract of volatiles, including EEW, in a first "aliquot" (Aliquot 1).

In these methods, cuttings associated volatiles, including EEW, were frozen onto a liquid nitrogen ($LN_2$) cryogenic trap. After about 7 minutes, the cryogenic trap was evacuated by application of hard vacuum, about $10^{-5}$ Torr, the flow path from the cryogenic trap was opened to the mass spectrometer, and the trap was allowed to warm and release volatiles into the mass spectrometer for analyses. The temperature range during warming went generally in each case from about −194 to −20 degrees centigrade ("C"). As the trap warmed, gases were released from the trap (presumably according to their sublimation temperatures; generally, lighter compounds evolve at lower temperatures, and heavier compounds at higher temperatures, however water, by its unique nature, is an exception to this rule being a light compound that sublimates at higher temperatures). Following the 20 millibar "Aliquot 1" (A1) analysis, a second extraction of volatiles, including RRW, and analysis (an "Aliquot 2" (A2) analysis) was performed using the sample by applying a vacuum pressure at about 2 millibars, or about 1/500th of an atmosphere, to each of the samples that were subjected to the Aliquot 1 analysis.

Figure 2:
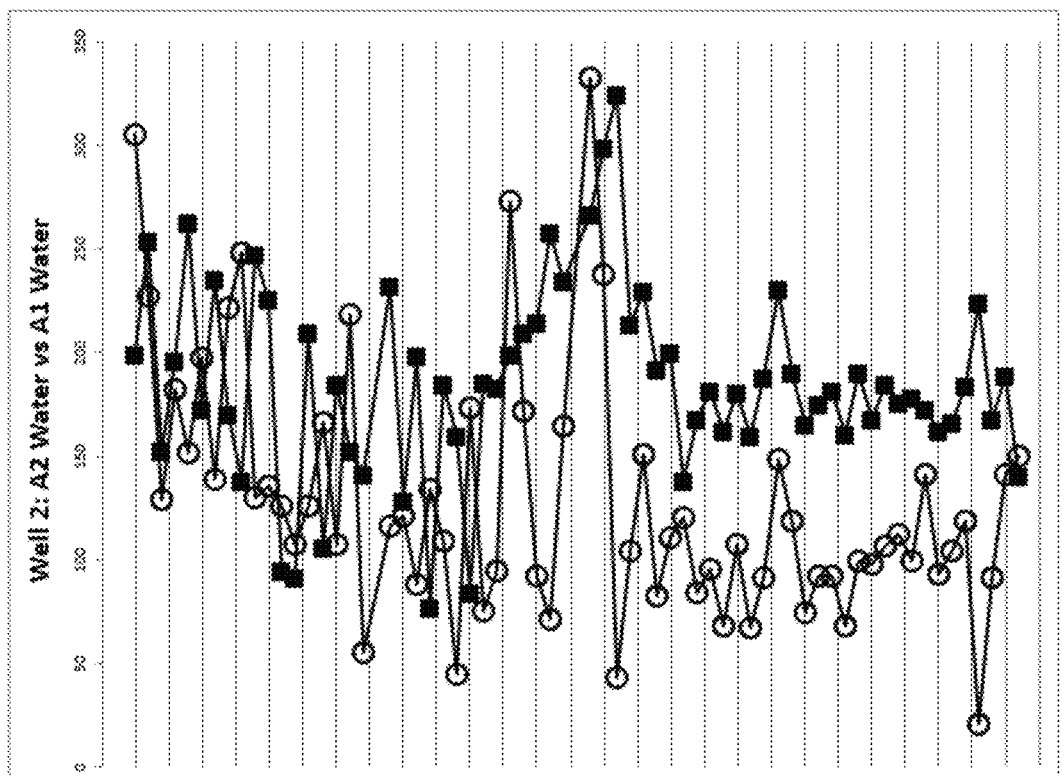
FIG. 2 illustrates the combined water release of samples from a $2^{nd}$ producing vertical oil well (well 2) having low visibility oil pay zones.
Figure 1:
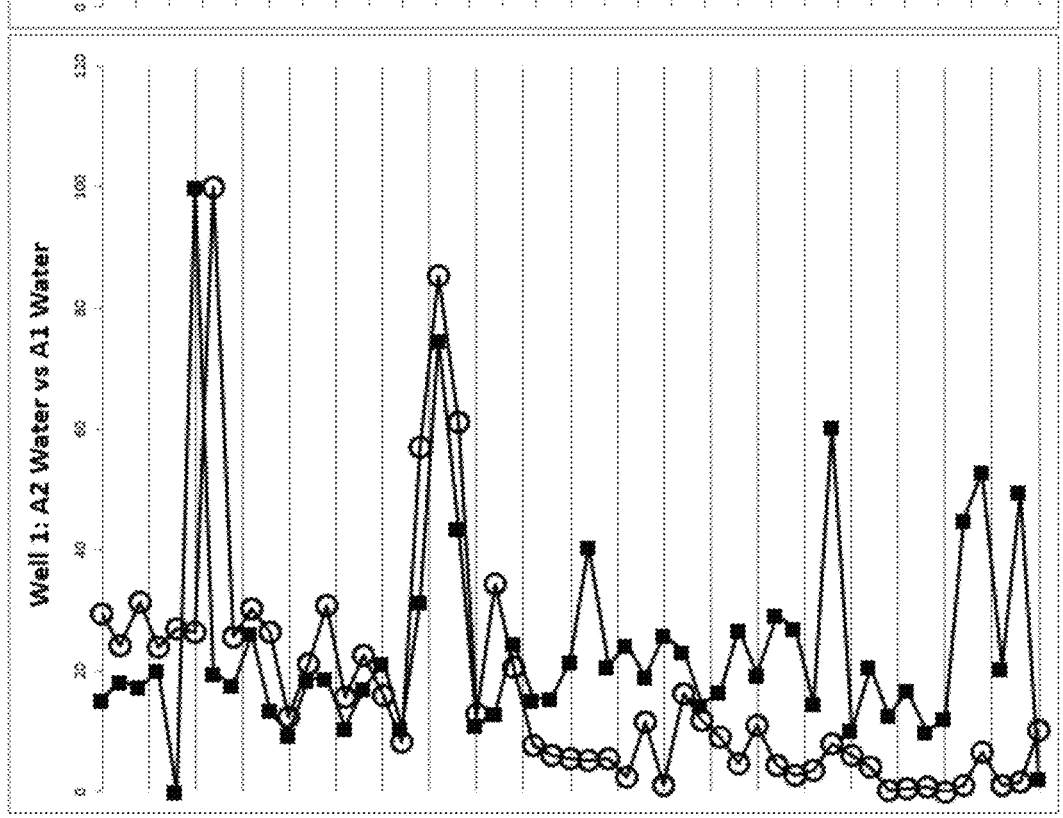
FIG. 1 illustrates the combined water release of samples from a producing vertical oil well (well 1) having low visibility oil pay zones.

Water data (EEW, RRW, and/or combined water) are shown versus depths (specific depths not shown) that the cuttings were estimated to have originated from for two wells in FIGS. 1 to 8. FIGS. 1 and 2 show the combined water release analyzed for these wells. In these figures and generally throughout all the applicable figures, the Aliquot 1 data is shown as open circles and Aliquot 2 data is shown as filled squares.

These 2 wells are producing vertical oil wells. Both have low visibility oil pay zones. The well on the left in FIG. 1 is low visibility as its pay zones are thin sand beds not easily seen in well logs. The well on the right is low visibility because it has fresh formation water that has resistivity about as high as the oil. The plots of combined water for both aliquots do not lend to easily locating the oil pay zones.

Figure 4:
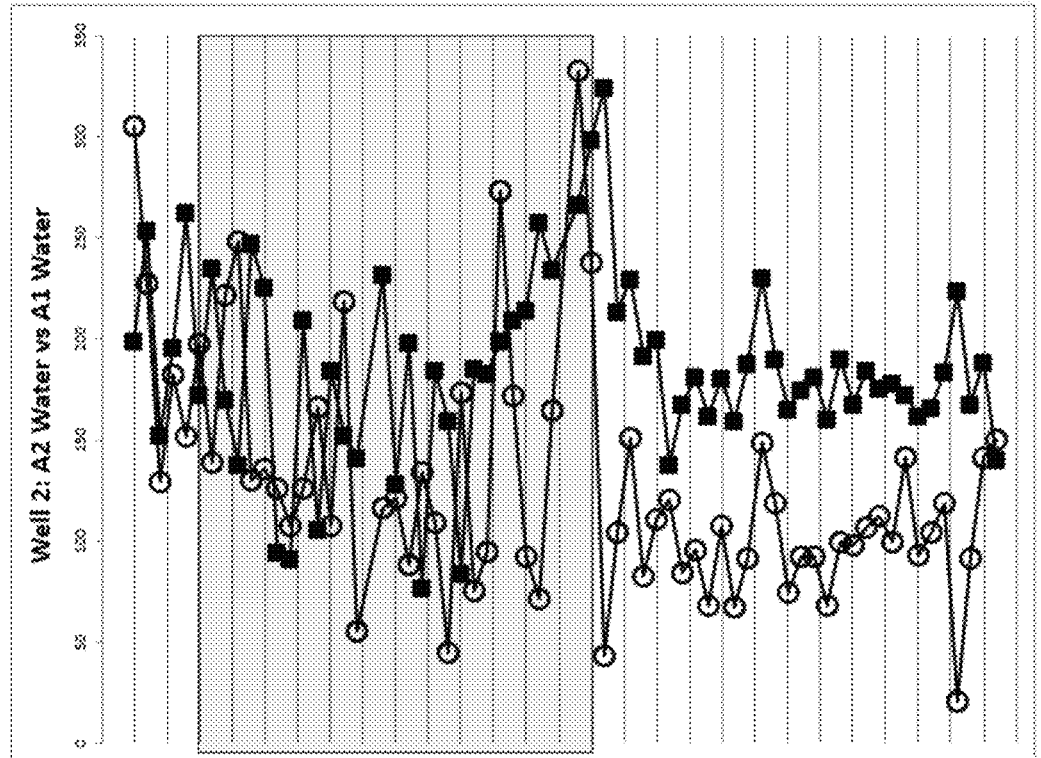
FIG. 4 illustrates zones of expected oil production of the well from FIG. 2, the shading identifying areas which are oil-wet.
Figure 3:
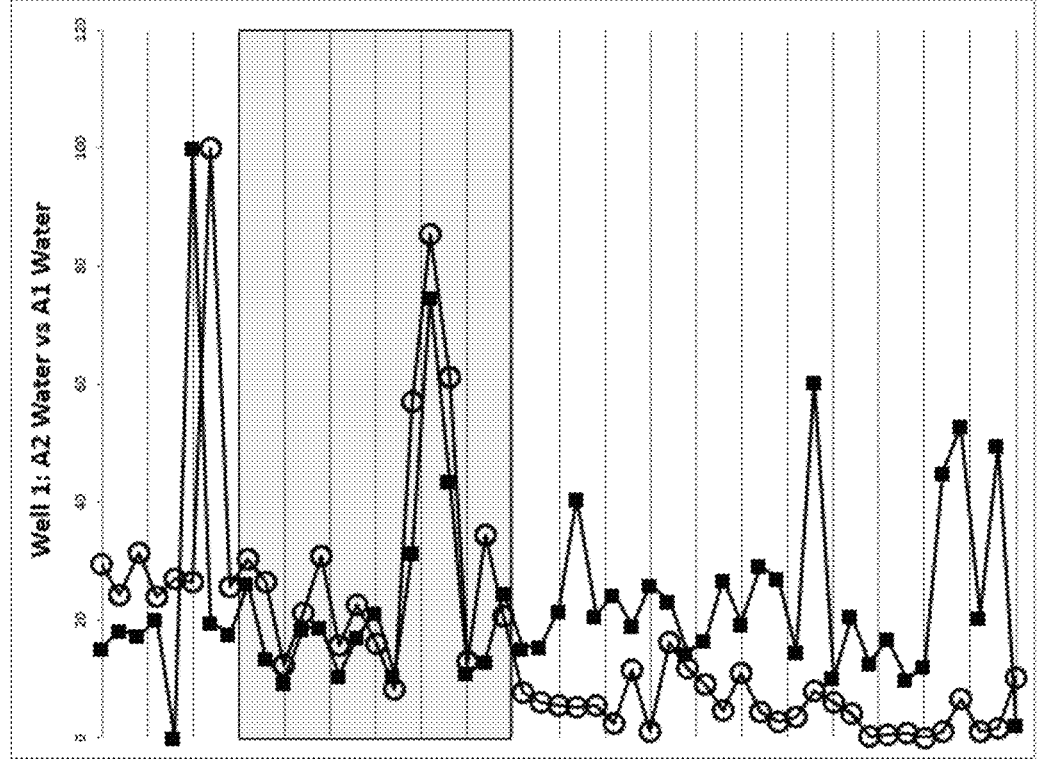
FIG. 3 illustrates zones of expected oil production of the same well as described in FIG. 1, the shading identifying areas which are oil-wet.

FIGS. 3 and 4 show shaded zones for each well that indicate the areas of where oil-wet rock is present, and correspondingly indicate areas of oil production in each well. In FIG. 3, the Aliquot 1 and Aliquot 2 curves are closer to one another in the shaded, pay zone-related areas than in the non-shaded, non-productive zones. This is even more apparent in FIGS. 5 and 6. This demonstrates that the relationship of EEW and RRW is associated with water-wet rock characterization and pay zones, even pay zones that are difficult to otherwise identify, including even using my previously described methods.

FIGS. 5 and 6 show the Aliquot 1 and Aliquot 2 water curves each as a fraction of water released in each aliquot divided by the sum of the water released from both aliquots, in other words each curve shows the mole fraction of water released by each aliquot for each depth. For each depth, the sum of the 2 aliquots is in approximate unity, or about 1. This also reflects how the relationship between EEW and combined water is an indicator of oil-wetting, present day petroleum associated pay zones, or of oil wetting zones that were filled with oil in the past but have since lost their oil.

The shallower sections of each well shows the convergence of the two curves (again, Aliquot 1 water indicated as open circles and Aliquot 2 water indicated by filled squares), with Aliquot 1 water often in excess of Aliquot 2 water. Deeper in the well the curves diverge, and the Aliquot 2 water exceeds the Aliquot 1 water. Again, this reflects how the relationship of these values can be used to identify oil wetting/pay zone-associated areas, versus the water wetting zones of a formation from cuttings.

FIGS. 7 and 8 show these same curves, but now with the zones that incorporate oil-wet rock and corresponding oil production are clearly indicated. In the zones of known oil production, the two curves approach each other, and often the Aliquot 1 water data exceeds the Aliquot 2 water data. These data are from old washed and dried cuttings.

For the purpose of making comparisons clearer, many figures presented herein have been presented in a side-by-side manner. A set of two figures presented side-by-side is often referred to herein as a panel (e.g., FIGS. 7 and 8 are presented together, as a panel of Figures comprising FIG. 7 and FIG. 8).

Figure 8A:
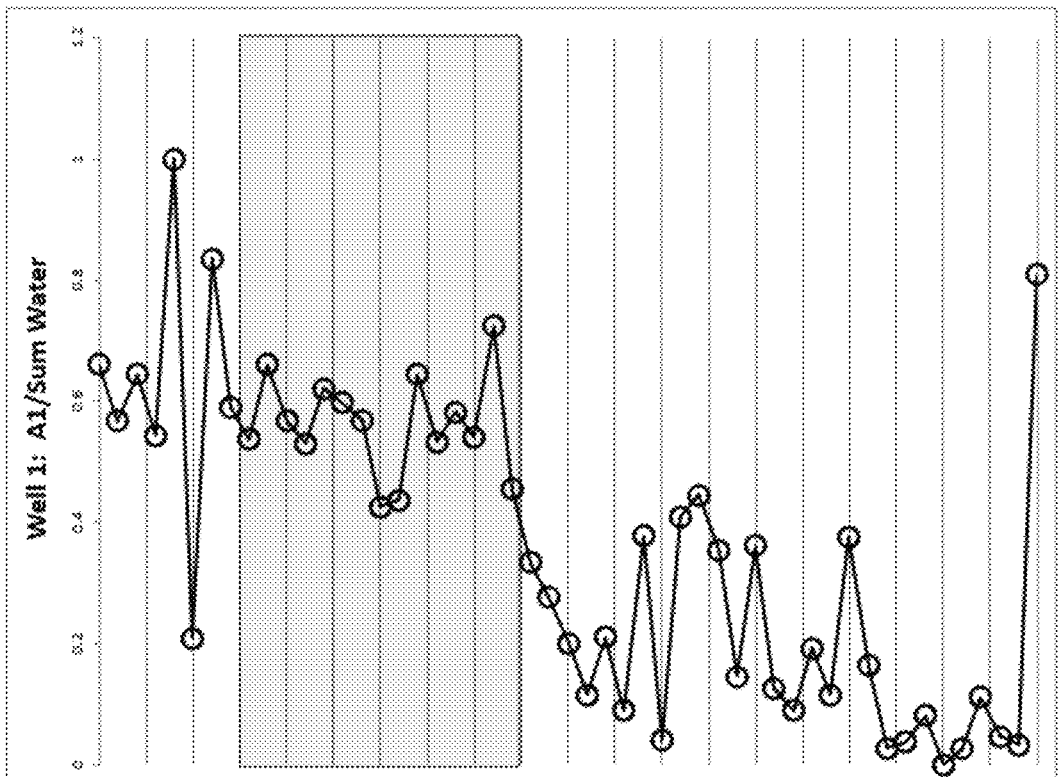
FIG. 8A illustrates the same curve of FIG. 7 with mole fraction water curves for both Aliquot 1 and Aliquot 2, with the oil wetting/pay zone indicated by shading (FIG. 8A is provided as a panel with FIG. 7A to facilitate comparison).
Figure 7A:
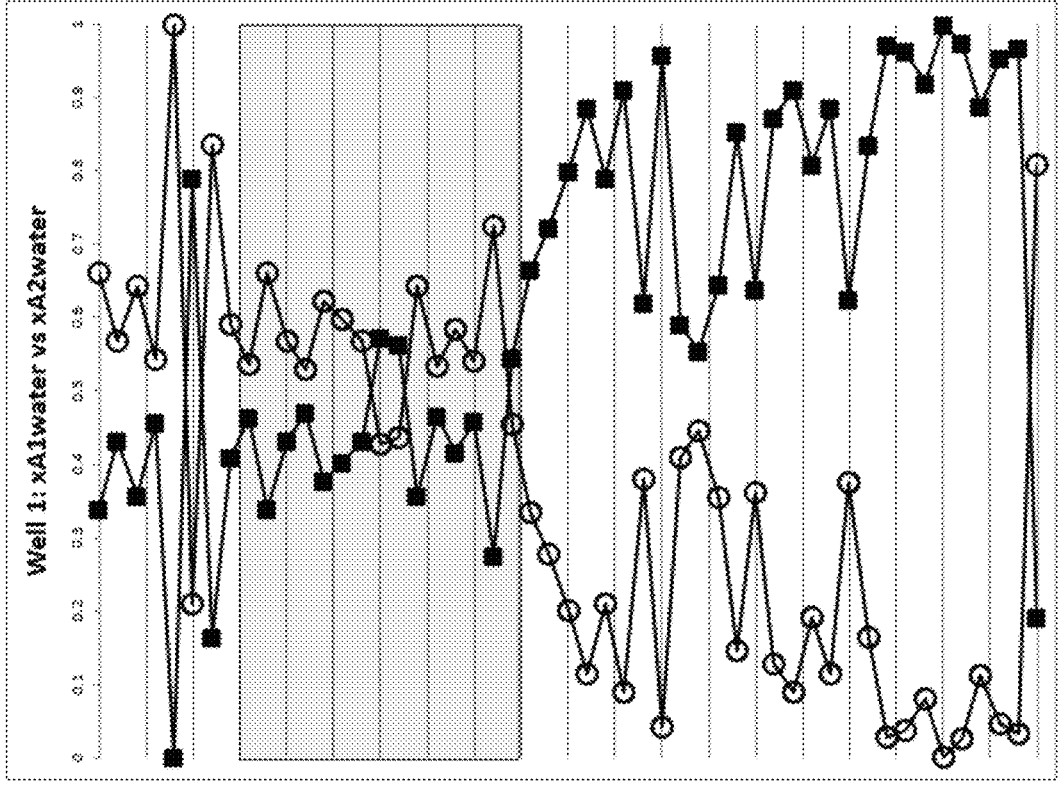
FIG. 7A illustrates the same curve of FIG. 7 showing the mole fraction water curves for both Aliquot 1 and Aliquot 2, with the oil wetting/pay zone indicated by shading (FIG. 7A is provided as a panel with FIG. 8A to facilitate comparison).

FIGS. 7A-7B and FIGS. 8A-8B also show data for the first well, which in FIGS. 1 through 8 was shown on the left in each panel, e.g., the well of FIG. 1 of FIGS. 1/2, the well of FIG. 3 of FIGS. 3/4, the well of FIG. 5 of FIGS. 5/6, and the well of FIG. 7 of FIGS. 7/8. FIGS. 7A and 8A show the mole fraction water curves for both Aliquot 1 and Aliquot 2, with the oil wetting/pay zone indicated by shading. FIGS. 7A and 8A are the same figure as FIG. 7.

FIGS. 7B and 8B show two other ways of presenting the water release data shown in FIGS. 7, 7A, and 7B. FIG. 7B shows just the Aliquot 1 water divided by the sum of the Aliquot 1 water plus the Aliquot 2 water, FIG. 7B shows the mole fraction of Aliquot 1 water relative to the total analyzed water. FIG. 7B is the same as FIG. 7A without showing the Aliquot 2 water, showing that the oil wetting sections of the well can be identified as those locations having mole fraction Aliquot 1 water of values about or greater than 0.5. FIG. 8B shows yet another way of visualizing the same data as the ratio of Aliquot 1 water to Aliquot 2 water. FIG. 8B shows that oil wetting sections of the well have ratios of Aliquot 1 water to Aliquot 2 water about 1 or higher.

Figure 8C:
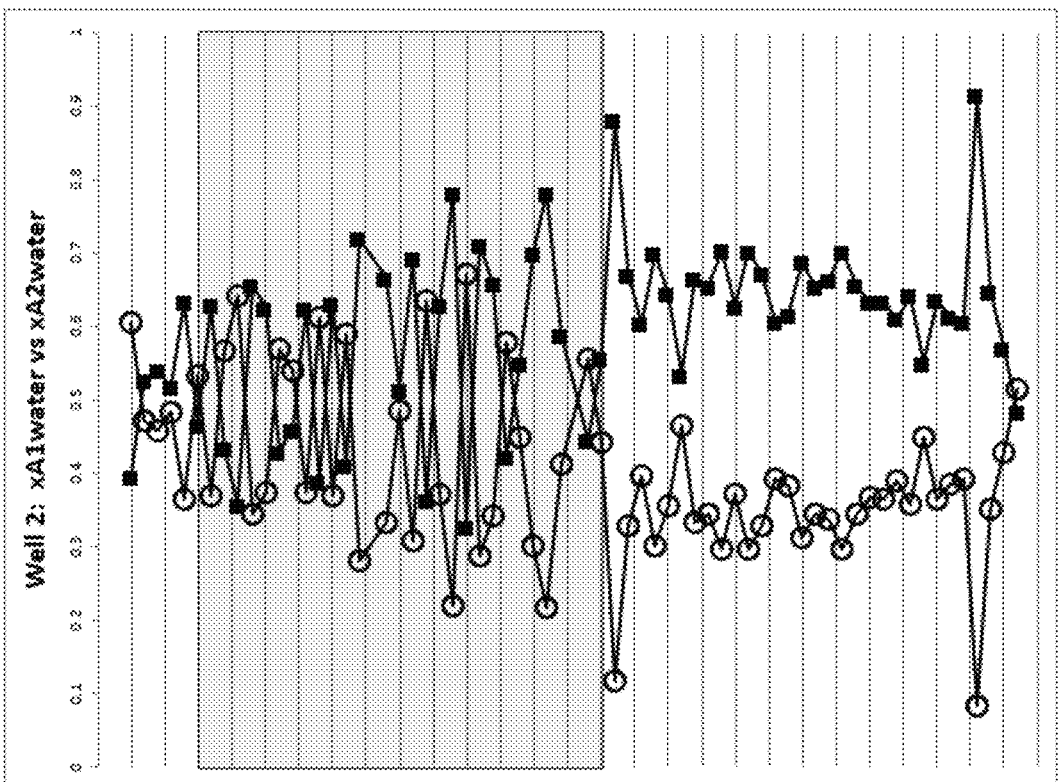
FIG. 8C illustrates the same curve of FIG. 8 with the mole fraction water curves for both Aliquot 1 and Aliquot 2 with the oil wetting/pay zone indicated by shading (FIG. 8C is provided as a panel with FIG. 7C to facilitate comparison).
Figure 7C:
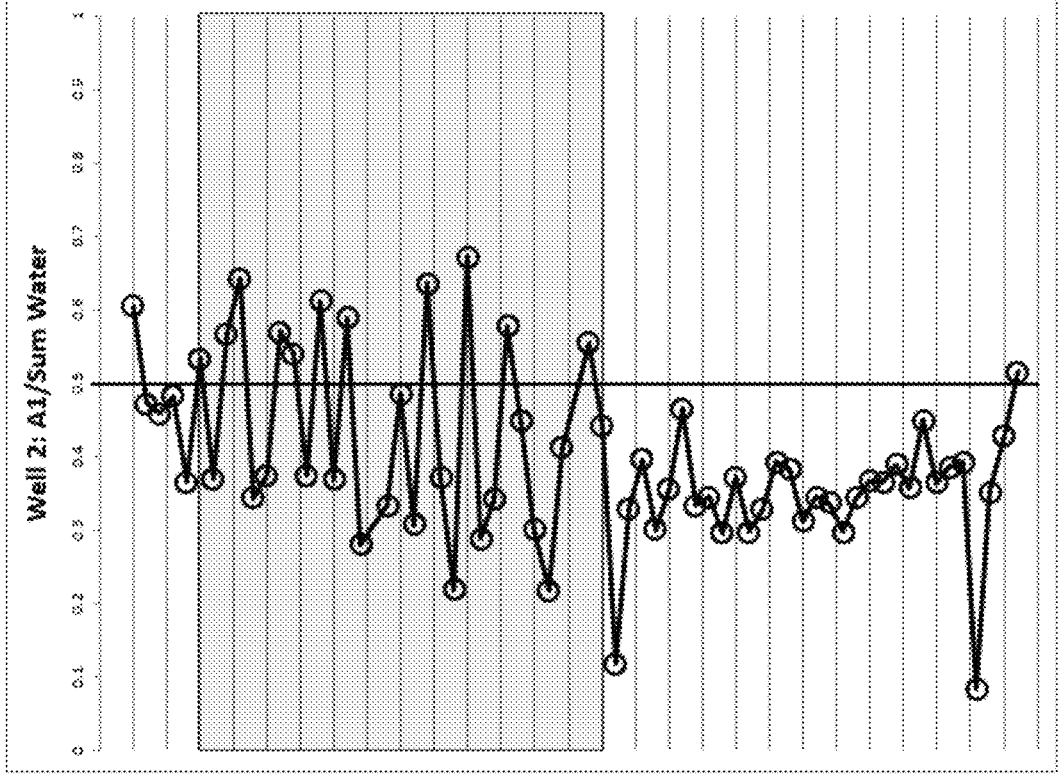
FIG. 7C illustrates the same curve of FIG. 8 with the mole fraction water curves for both Aliquot 1 and Aliquot 2 with the oil wetting/pay zone indicated by shading (FIG. 7C is provided as a panel with FIG. 8C to facilitate comparison).

FIGS. 7C-7D and FIGS. 8C-8D show data for the second well, which in FIGS. 1 through 8 was shown on the right in the presented panels (e.g., FIG. 2 of FIGS. 1/2, FIG. 4 of FIGS. 3/4, FIG. 6 of FIGS. 5/6, and FIG. 8 of FIGS. 7/8). In both of these panels (7C/8C and 7D/8D), the left figures, FIGS. 7C and 8C, show the mole fraction water curves for both Aliquot1 and Aliquot 2 with the oil wetting/pay zone indicated by shading. FIGS. 7C and 8C are the same figure as FIG. 8. FIGS. 7D and 8D show two other ways of presenting the water release data shown in FIGS. 8, 8A, and 8B. FIG. 7D shows just the Aliquot 1 water divided by the sum of the Aliquot 1 water plus the Aliquot 2 water, FIG. 7D shows the mole fraction of Aliquot 1 water relative to the total analyzed water. FIG. 7D is the same as FIG. 7C without showing the Aliquot 2 water, showing that the oil wetting sections of the well can be identified as those locations having mole fraction Aliquot 1 water of values about or greater than 0.5. FIG. 8D shows yet another way of visualizing the same data as the ratio of Aliquot 1 water to Aliquot 2 water. FIG. 8D shows that oil wetting sections of the well have ratios of Aliquot 1 water to Aliquot 2 water about 1 or higher.)

Figure 9:
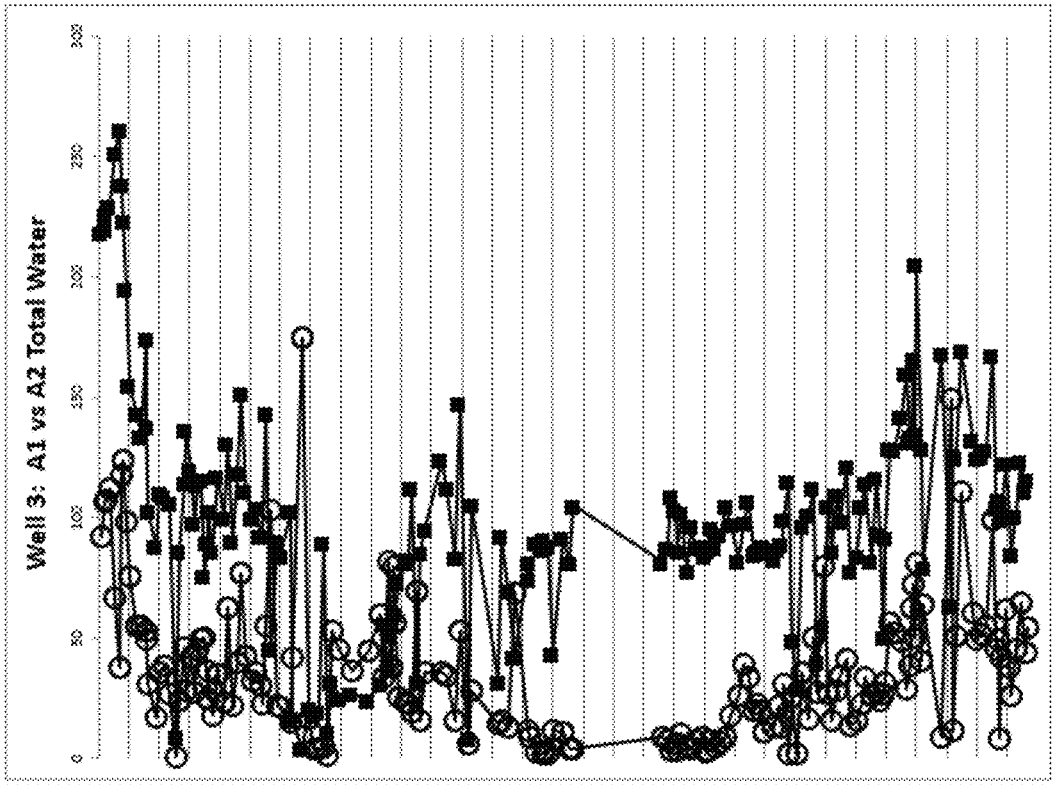
FIG. 9 illustrates Aliquot 1 and Aliquot 2 mole fraction of old cutting samples (note that FIGS. 9-22 represent data from the same well).
Figure 10:
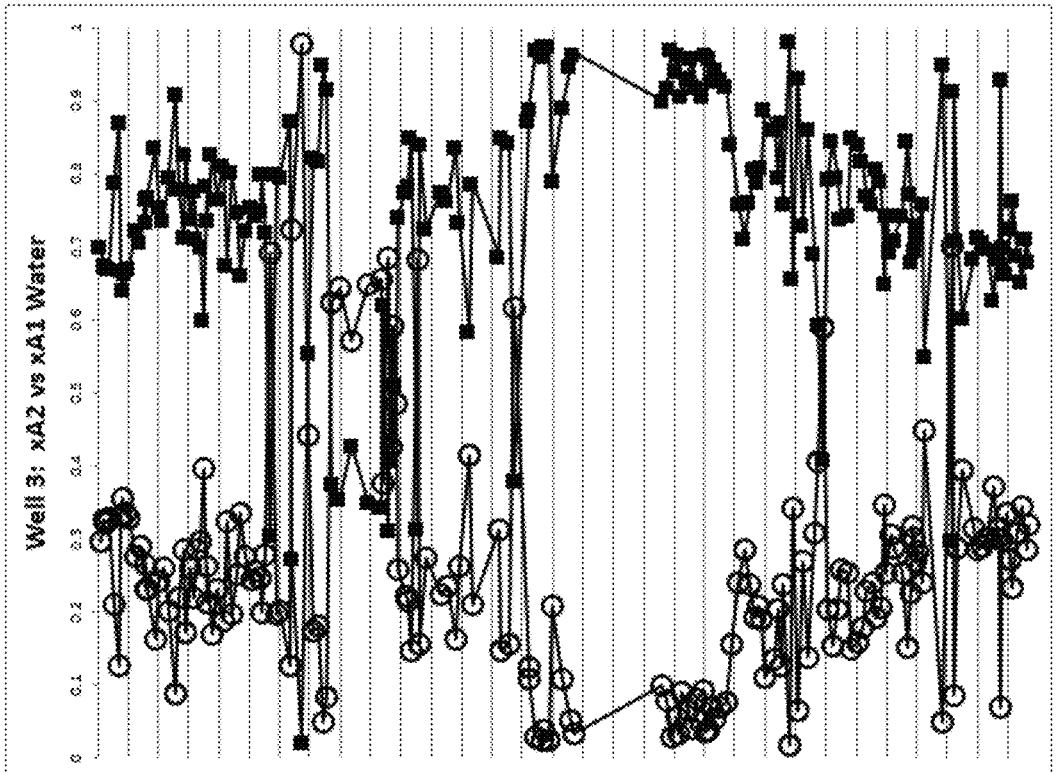
FIG. 10 illustrates Aliquot 1 and Aliquot 2 combined water volumes from old petroleum cutting samples.

FIGS. 9 to 22 all focus on the same well (again—specific depths not shown in most figures). These samples are old core samples. FIGS. 9 and 10 show the Aliquot 1 (open circles) and Aliquot 2 (filled squares) mole fractions (FIG. 9) and the combined (absolute analyzed) water volumes (not normalized to the sum of both Aliquot 1 plus Aliquot 2 water, as the values are normalized in FIG. 9) (FIG. 10). Most of the samples shown in FIG. 9 are widely spread apart, with Aliquot 2 water significantly in excess of Aliquot 1 water. This behavior indicates water wetting samples. However, a zone starting just above 7590' and extending below 7615' (specific depths not shown) has the 2 curves coming closer together with the Aliquot 1 water in excess of the Aliquot 2 water. These data reflect additional examples of how water relationship data obtained by the inventive method can be used to identify oil wetting and pay zones, as well as sections of a well that were charged with oil in the past, but which have since lost the bulk of their oil.

FIGS. 11 and 12 show the same plots but now with 2 shaded bands to indicate 2 potential, oil wetting/oil pay zones in the zones with Aliquot 1 water in excess of Aliquot 2 water. In such zones, data indicate that rock is oil wet.

FIGS. 11A and 12A are the same as FIG. 11 showing the mole fractions of Aliquot 1 water and Aliquot 2 water each relative to the sum of Aliquot 1 water plus Aliquot 2 water. FIGS. 11A and 11B are presented for direct comparison with FIGS. 12A and 12B, respectively. FIG. 12A shows the mole fraction Aliquot 1 water which equals Aliquot 1 water divided by the sum of Aliquot 1 water plus Aliquot 2 water. FIG. 12A is like FIG. 11A without the mole fraction Aliquot 1 water plotted. In FIG. 12A, sample values of about or more than 0.5 are oil wetting. FIG. 12A shows that it is not necessary to plot both mole fractions of both Aliquot 1 water and Aliquot 2 water to identify oil wetting zones. FIG. 12B shows another method of viewing this data for this well using the ratio of Aliquot 1 water to Aliquot 2 water. Samples having values about 1 or greater than 1 are oil wetting.

Figure 14:
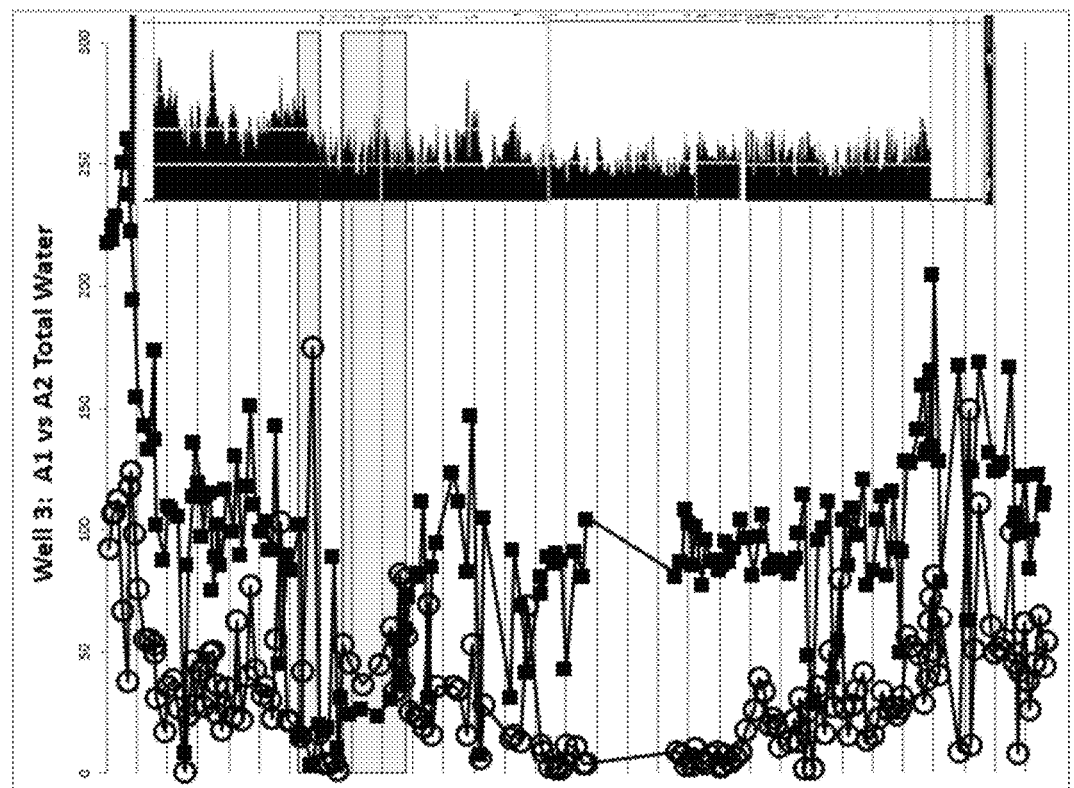
FIG. 14 is essentially the same figure as FIG. 12 but with the water saturation from well logs (Sw) curve for the well added; shading identifying areas which are oil-wet.
Figure 13:
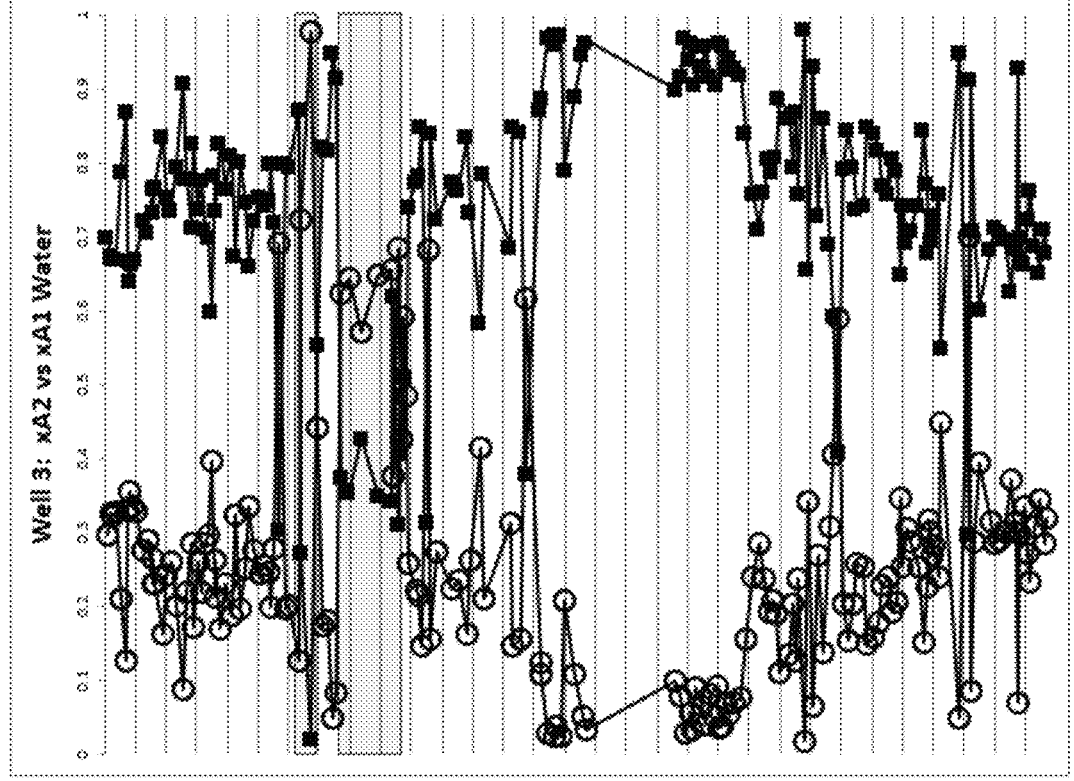
FIG. 13 is similar to FIG. 11 but with the water saturation from well logs (Sw) curve added to the panel view with FIG. 14 (with the Sw curve present within FIG. 14); shading identifying areas which are oil-wet.

FIGS. 13 and 14 are similar to FIGS. 11 and 12, but now the Sw (water saturation) curve determined by petrophysics has been added. The Sw curve shows significant oil saturation, as indicated by low Sw values throughout most of the curve, but no discrete pay zones are indicated by petrophysics. However, the Aliquot 1 and 2 curves do indicate the shaded areas as 2 oil wetting/oil pay zones. If the Aliquot 1 and 2 water interpretation is correct, as expected, then this would be an example of low visibility pay zones, as they are not resolved by petrophysics of the well logs (production confirmation has not yet been obtained for this aspect of the wellsite). In the shaded areas of FIGS. 13 and 14, samples are identifiable as oil-wet.

Figures 15, 16:
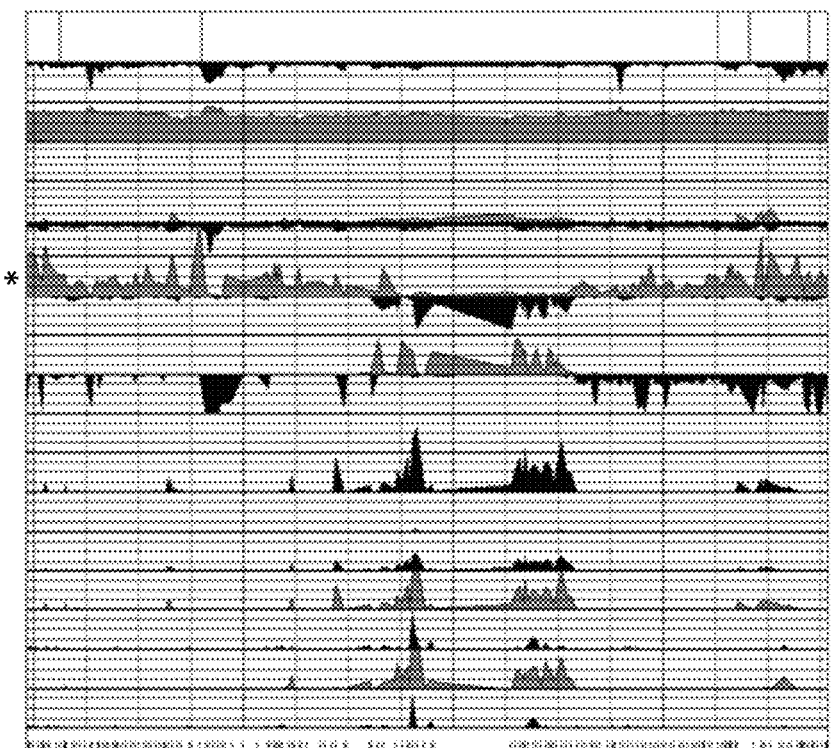
FIG. 15 illustrates Aliquot 1 data with volatiles property logs.
FIG. 16 illustrates Aliquot 2 data with volatiles property logs.

FIGS. 15 and 16 show the Aliquot 1 and 2 data displayed in combination with the volatiles property logs that reflect the rock volatiles analyses of my prior patent applications and patents. Water is shown as the curve in each diagram labeled with an asterisk (*). This exemplifies the combination of my previously invented methods with the inventive methods described in this disclosure.

FIGS. 17 and 18 show the same property logs shown as FIGS. 15 and 16, but now with the 2 shaded oil wetting/pay zone indicator bars from FIGS. 13 and 14. Viewing the water curves indicated asterisks (*), one can see that these zones are the only location in this core where the Aliquot 1 water is higher than the Aliquot 2 water.

Figure 20:
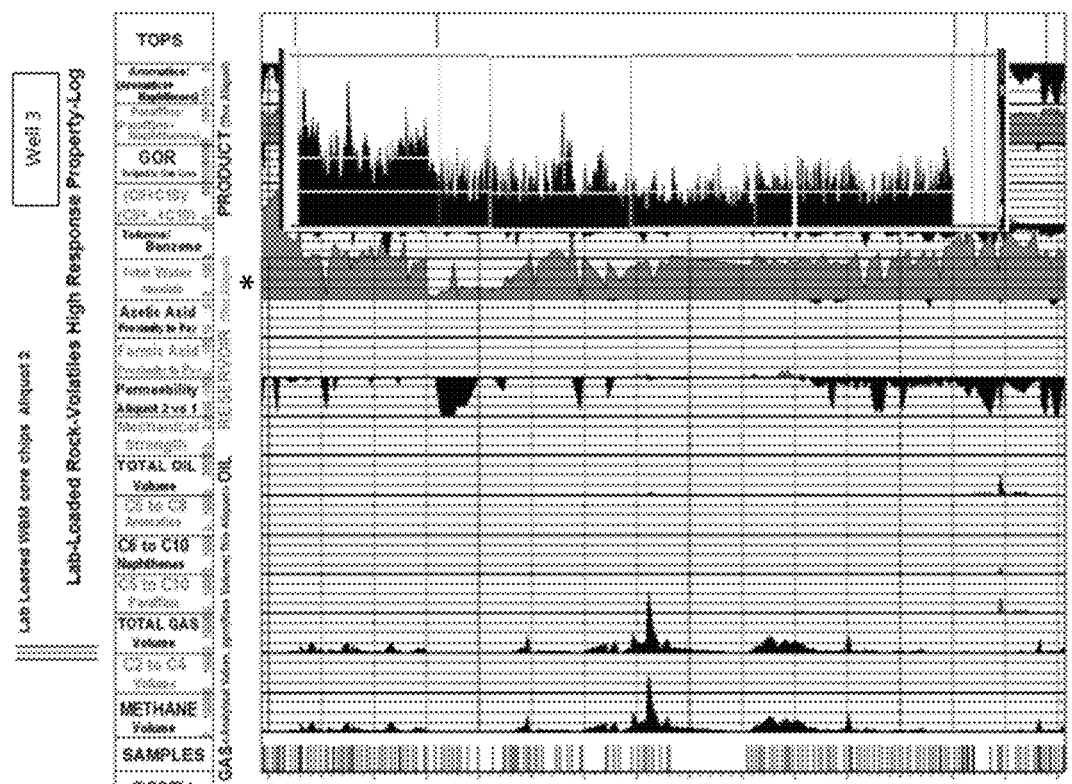
FIG. 20 is the same property log as shown in FIG. 18 with the water saturation (Sw) data included.
Figure 19:
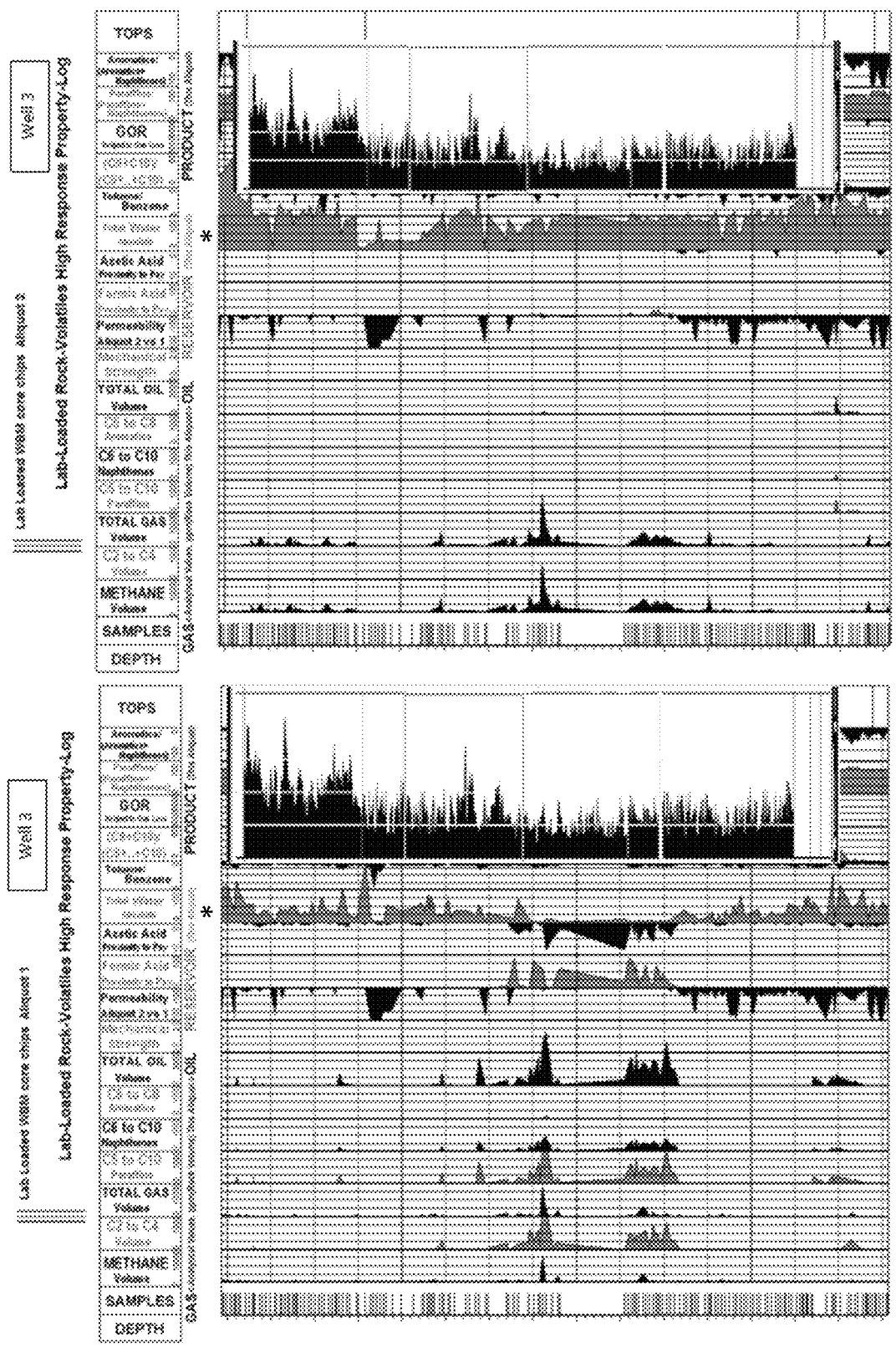
FIG. 19 is the same property log as shown in FIG. 17 with the water saturation (Sw) data for the well also included.

FIGS. 19 and 20 are the same as FIGS. 17 and 18, but now the Sw petrophysics curve has been added. It is clear for both Aliquots 1 and 2 that there is significant structure in the water curve on each property log that is not reflected in the Sw log, although the water curve in the Aliquot 2 property log shows more features in common with the Sw petrophysics curve than does the water curve in the Aliquot 1 property log.

Figure 22:
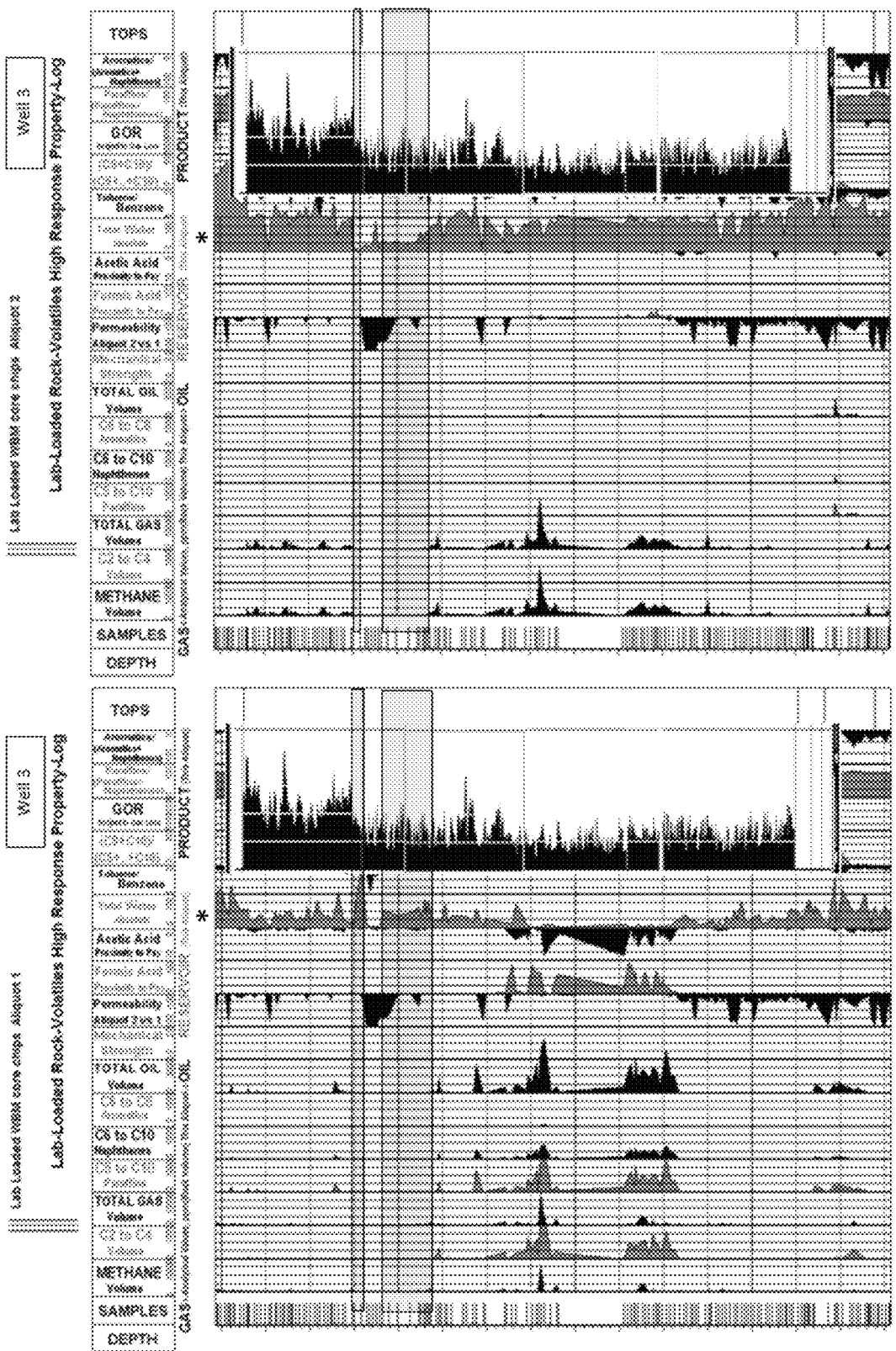
FIG. 22 is the same as FIG. 20 with added pay zone indication.
Figure 21:
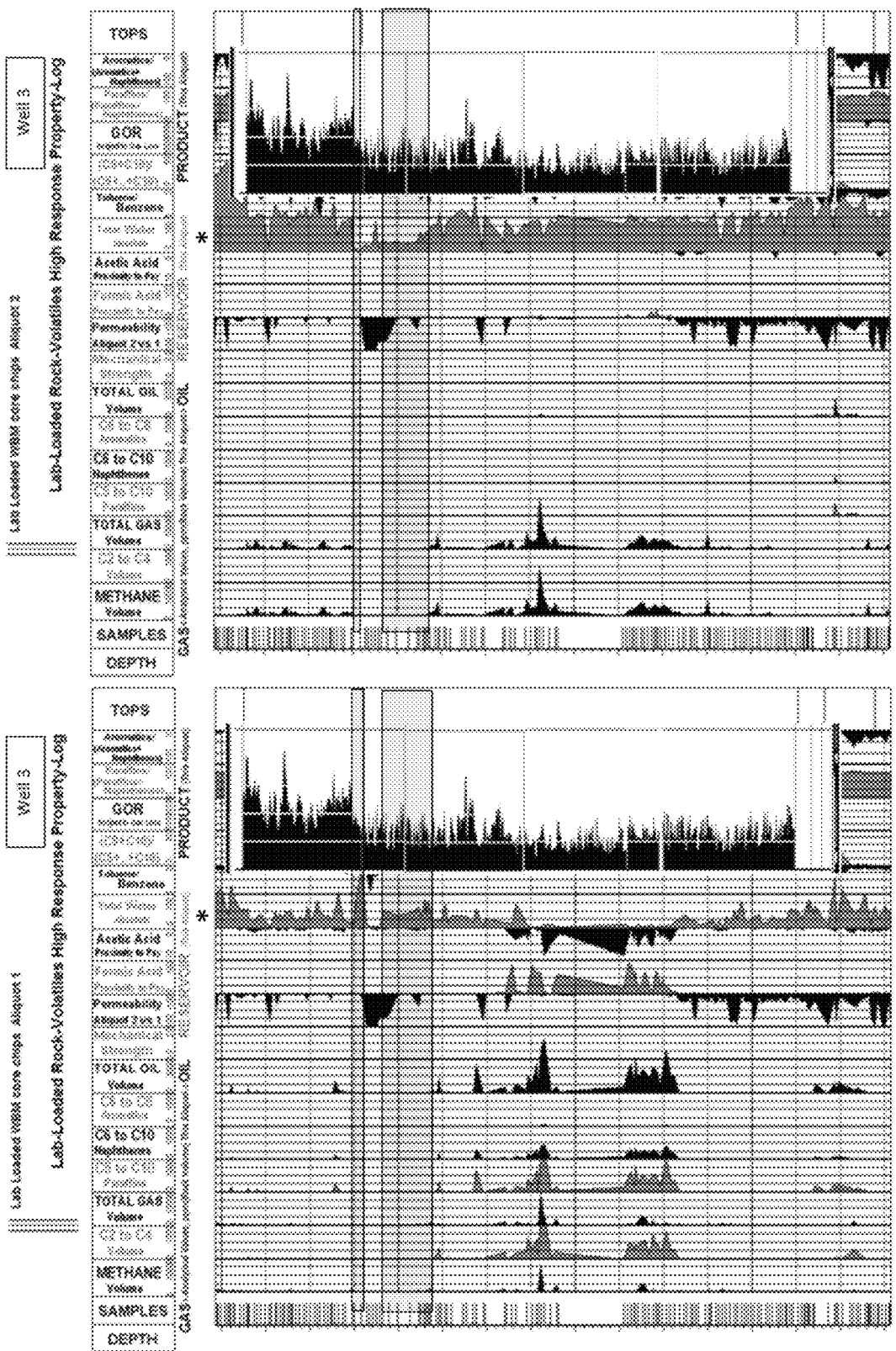
FIG. 21 is the same as FIG. 19 with added pay zone indication.

FIGS. 21 and 22 are the same as FIGS. 19 and 20, but now I have added the 2 shaded oil wetting/pay zone bars as determined in FIGS. 13 and 14. Note there is nothing in the Petrophysics Sw curve to indicate the oil pay zones (designated by shading) as suggested by FIGS. 13 and 14.

FIGS. 23 through 28 all show data from a lateral drilled off the vertical well shown in FIGS. 13-22 (specific depths not shown). Aliquot 1 data is again shown as open circles and Aliquot 2 data is shown as filled squares.

FIGS. 23 and 24 show the combined water curves on the right, and the mole fraction water curves on the left for this well.

Figures 25, 26:
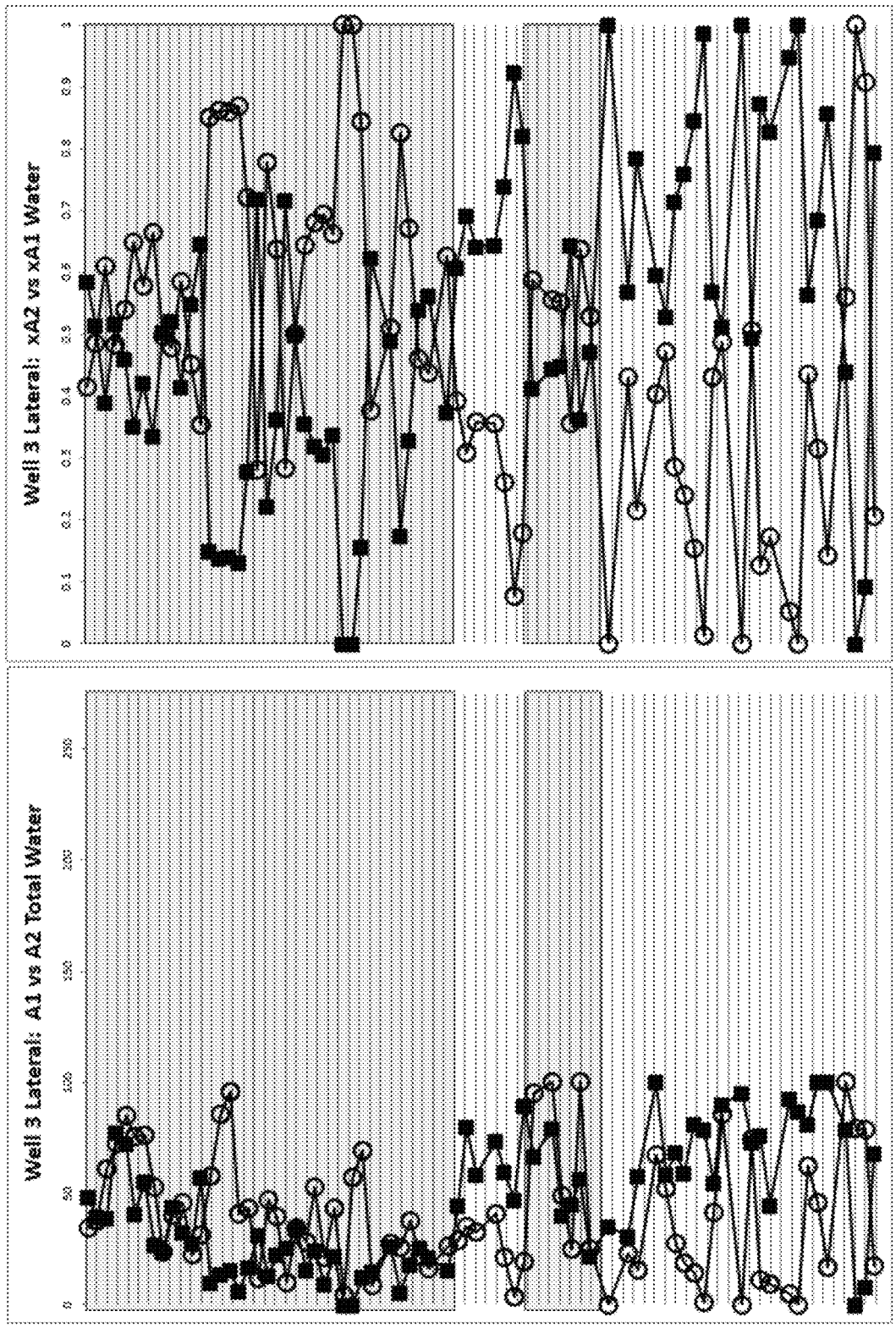
FIG. 25 illustrates Aliquot 1 and Aliquot 2 mole fraction water convergence indicating zones of oil production in well 3, the shading identifying areas which are oil-wet.
FIG. 26 illustrates Aliquot 1 and Aliquot 2 mole fraction water convergence indicating zones of oil production in well 3, the shading identifying areas which are oil-wet.

FIGS. 25 and 26 show shaded zones of Aliquot 1 and Aliquot 2 mole fraction water convergence indicating these are zones in which rock is oil wet and oil production occurs.

Figure 28:
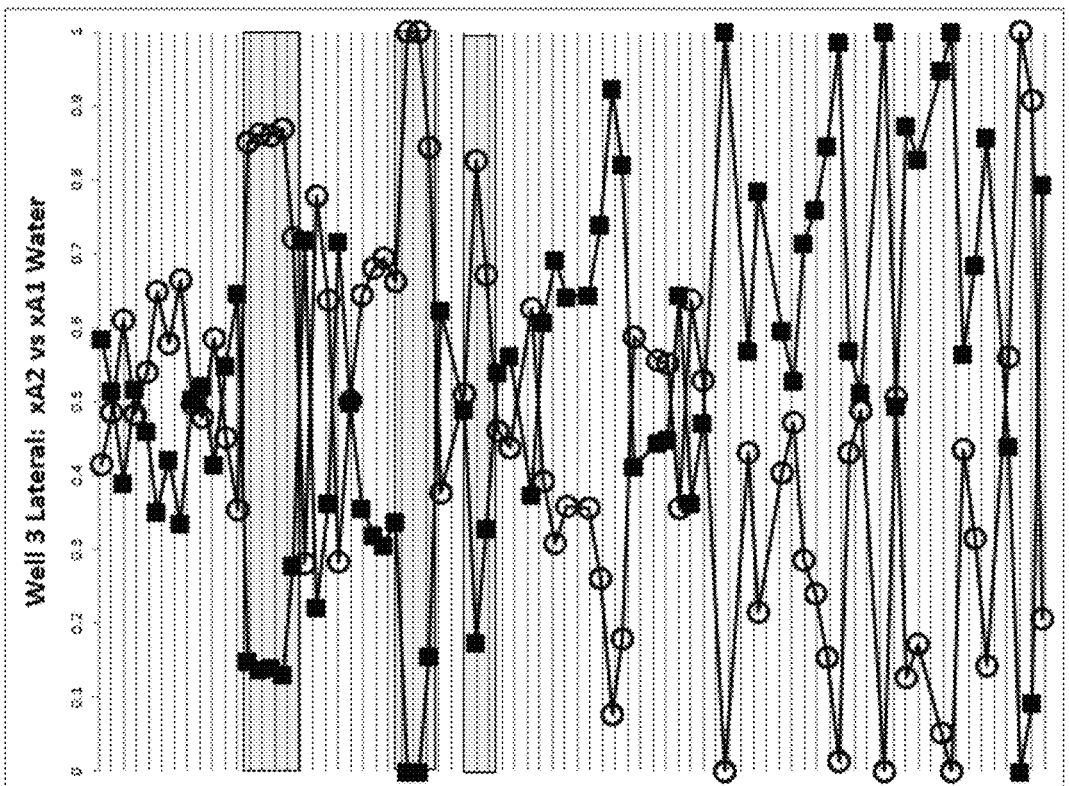
FIG. 28 illustrates zones of Aliquot 1 to Aliquot 2 mole water fraction of 0.8 or greater indicating zones of primary oil production in a horizontal well, the shading identifying areas which are oil-wet.
Figure 27:
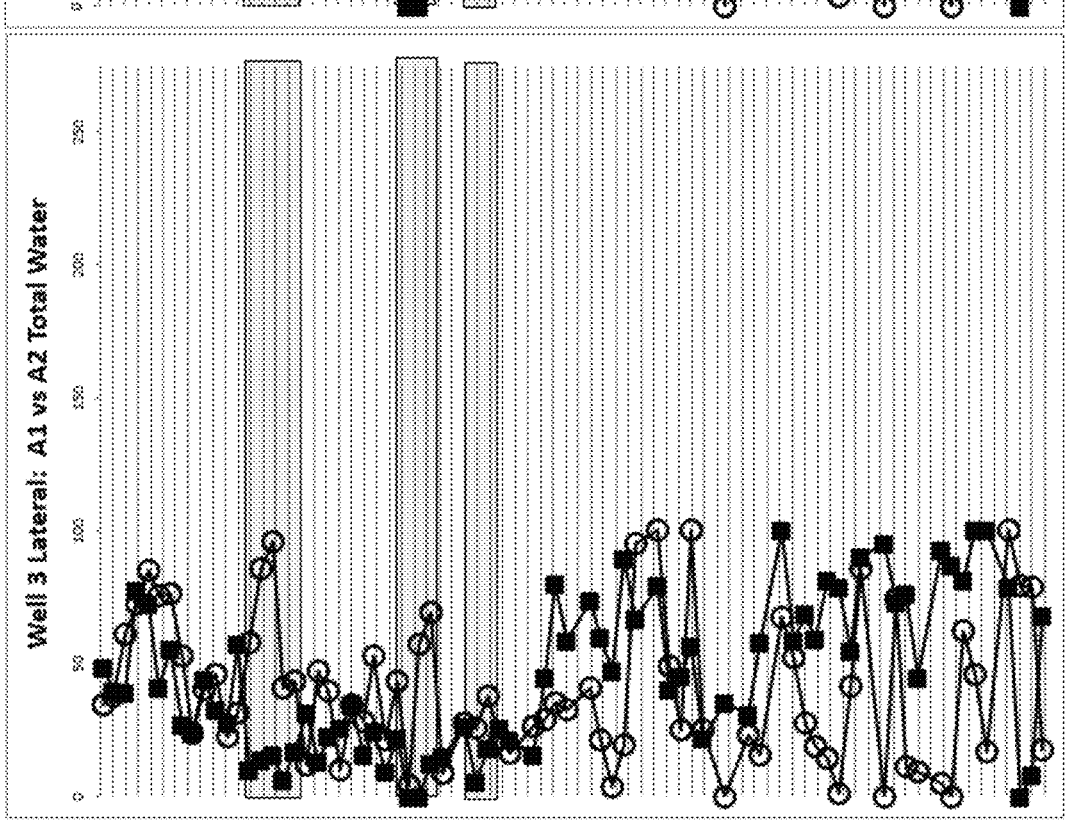
FIG. 27 illustrates zones associated with Aliquot 1: Aliquot 2 measurements of 0.8 or greater indicating zones of primary oil production in a horizontal well, the shading identifying areas which are oil-wet.

In FIGS. 27 and 28, 3 zones have Aliquot 1 mole fraction (indicated by open circles) water of 0.8 or greater as indicated by shading. These are thought to be the zones of oil-wet rock and primary oil production in this horizontal well. No petrophysics data is available for this well. This well was a low performing oil well producing about 70 MBO (thousand barrels of oil) in the first 3.5 years of production. In general, a good quality 1-mile lateral in this area produces in excess of 200 MBO. The 3 zones have a net thickness of about 1200'. This is close to ¼th the length of a "1-mile" lateral, which is usually about 4700'. If we multiply the present-day cumulative production of 70 MBO by 4 the result is 280 MBO, which would be considered a very successful 1-mile lateral oil well in this area. Using the data from the vertical well to land in the good oil pay zone, this lateral may have been a much better well.

FIGS. 28A and 28B are the same as FIG. 28 showing the mole fractions of both Aliquot 1 and Aliquot 2 water and showing 3 shaded oil wetting pay zones having values about or more than 0.8. FIGS. 28A and 28B are shown to offer direct comparisons with FIGS. 27A and 27B, respectively. FIG. 27A shows the mole fraction of Aliquot 1 water which is the ratio of Aliquot 1 water to the sum of Aliquot 1 water plus Aliquot 2 water. FIG. 27A is like FIG. 28B without plotting the mole fraction of Aliquot 2 water. FIG. 27 demonstrates that the 3 oil- wetting pay zones can be delineated using just the mole fraction of Aliquot 1 water. Not shown is a Figure of only mole fraction of Aliquot 2 water which could also be used with showing the Aliquot 1 water to delineate the 3 oil-wetting pay zones by their low mole fractions of Aliquot 2 water. FIG. 27B shows the ratio of Aliquot 1 water to Aliquot 2 water. The 3 oil-wetting pay zones all show values of this ratio well in excess of 1, indicating their oil wetting nature.)

Figure 29:
FIG. 29 illustrates output obtained from a capacitance manometer for sample water obtained by methods of the invention.
Figure 30:
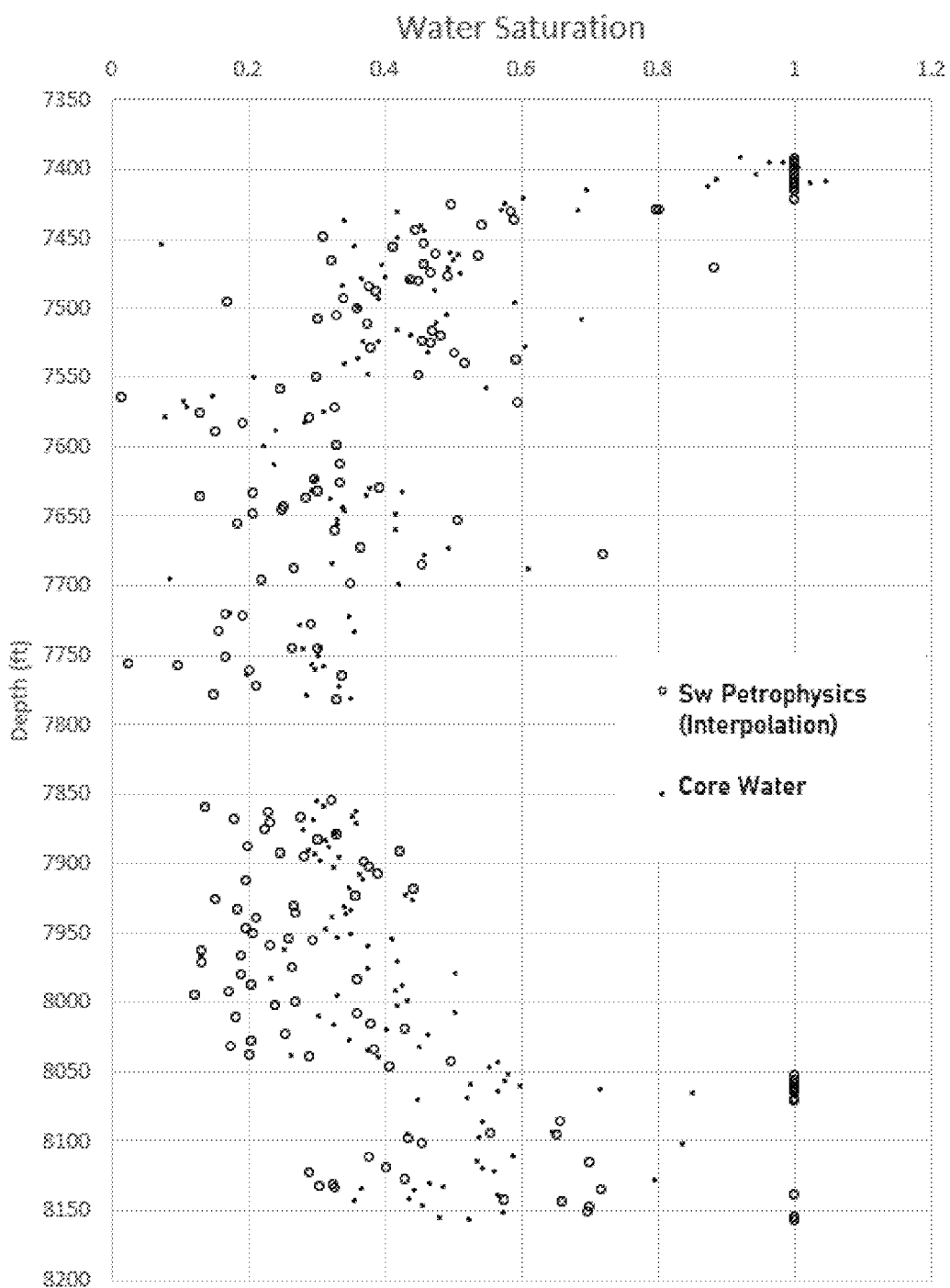
FIG. 30 is an interpolation of the well log Sw of the well shown in FIGS. 9-22 and illustrates a foot-by-foot comparison of the Sw data with the combined water data of the present invention.

FIG. 29 illustrates a method of combining CMSVA and the water analysis methods of this invention in a single analysis, alleviating the limitation of a mass spectrometer in addressing the pressure from some amounts of evolved water. During operation/application of the analysis, volatiles flow is at a point directed away from the mass spectrometer and is directed only to pass near the capacitance manometer; in earlier methods, the water and other volatiles have been directed so as to be monitored by both the mass spectrometer and the capacitance manometer. The capacitance manometer then takes over the analysis from the mass spectrometer, measuring total absolute pressure. The point on the curve indicated by the dashed arrow is the point at which the volatiles are directed away from the mass spectrometer and toward the capacitance manometer, at which point the capacitance manometer takes over the analysis and measures total absolute pressure. This demonstrates the usefulness of incorporating and applying capacitance manometry in TAL analysis methods.

These examples demonstrate the how the application of various methods of the invention can be used to identify pay zones, even in areas where conventional logging cannot adequately map low visibility pay zones.

2. FIGS. 30-35 and Associated Analysis and Data

Descriptions of FIGS. 30-35 are provided by means of Examples of select applications of the methods described herein.

Example 2A

Well log Sw data for the well described in FIGS. 9-22 and discussed above was interpolated and collected along with the combined water (sum of EEW and RRW) data as measured by the methods discussed herein. These data are co-presented in a single graph in FIG. 30, wherein the x-axis of the FIG. 30 graph indicates water saturation, and the y-axis of the graph indicates well depth. Normalized combined water data, represented by dots, correlates strongly with interpolated Sw petrophysics data, represented in the graph by open circles. As this example indicates, water content analysis as described herein can be representative of more traditional well log Sw data, and because the water data described herein may be more feasibly collected, the methods described herein may represent a replacement or supplementation of existing, more expensive technology for the identification of pay zones or locations associated with a petroleum producing system.

Example 2B

Figure 31:
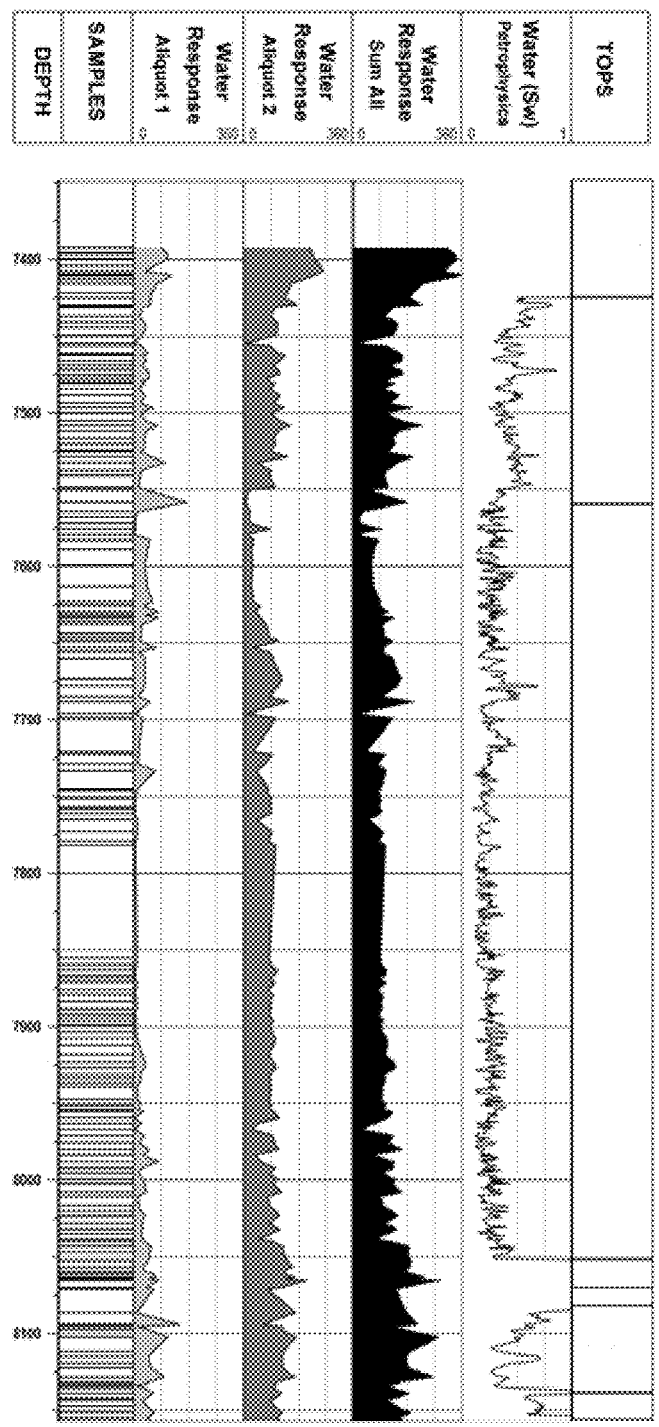
FIG. 31 illustrates a comparison of Aliquot 1, Aliquot 2, and combined water as measured in the present invention to the Sw from well logs, illustrating their strong correlation.

A set of samples collected from the same oil well shown in FIGS. 9 through 22 and FIG. 30 were analyzed according to the methods herein and the results of Aliquot 1 water (EEW) indicated by the lightest gray shading in FIG. 31, Aliquot 2 water (RRW) indicated by the darker gray shading in FIG. 31, and combined water (sum of EEW and RRW) indicated by the black shading in FIG. 31, were compared to petrophysics Sw data (white/no shading in FIG. 31) across a well. Water content was measured indirectly using a capacitance manometer. FIG. 31 presents this data side-by-side for comparison. As the FIG. 31 illustrates, the combined water data as measured indirectly by a capacitance manometer correlates strongly with the well log Sw data. As a result, this example indicates that the combined water as measured indirectly by a capacitance manometer can be representative of total water saturation and may be used for the identification of pay zones or locations associated with a petroleum producing system.

Example 2C

Two sets of samples from two horizontal wells (Well A and Well B) were provided for analysis. The production status of the two wells were unknown at the time of the analysis; that is, the production status was blinded to those performing the analysis but known by those providing the samples. The aim of this experiment was to analyze the two sets of samples and to identify the higher producing well of the two (e.g., identify the producing well vs. the non- or lower producing well).

Samples were analyzed using the methods described herein and Aliquot 2 (RRW) data were measured indirectly using capacitance manometry and graphed for each well. These data are presented in FIGS. 32A and 32B, with FIG. 32A providing a graph of Aliquot 2 data along the lateral from the heel of the lateral (left) to the toe of the lateral (right), and FIG. 32B providing a graph of Aliquot 2 water data sorted by response. As indicated by the graphs, the two wells demonstrate different Aliquot 2 (RRW) patterns. Well A samples demonstrate a lower RRW water content than sample from Well B. As lower water content of such samples is indicative of higher oil content in the samples, Well A was identified as the higher producing well while Well B was identified as the lower producing well. This determination was confirmed by the sample providers.

This example serves as a validation that the use of water analyzed using the methods of the present invention and analyzed indirectly using capacitance manometry can distinguish between strong- and poor-oil producing wells.

Example 2D

Samples were collected from a well along with the conductance data for the same well. Samples were analyzed using the methods described herein and the combined water (sum of EEW and RRW) measurement collected on the samples was compared to the inverse of the wireline resistivity log data (representing conductance). This data is presented in FIG. 33, wherein the x-axis represents wireline conductance (1/Ohms), and the y-axis represents well depth in feet. The combined water data is represented by the black circles/dashed line and the inverse resistivity wireline data is represented by the solid gray line of the FIG. 33. As shown, the combined water data as measured by the methods herein correlate strongly with the conductance data. As this example indicates, water content analysis as described herein can be representative of more traditional wireline resistivity log data, and because the water data described herein may be more feasibly collected, the methods described herein may represent a replacement or supplementation of existing, more expensive technology for the identification of pay zones or locations associated with a petroleum producing system.

Example 2E

A further experiment was conducted to determine if a comparison of data collected on samples from the same location within a well, treated differently after collection and both prior to and during analysis using methods described herein, could aid in the identification of oil- vs. water wetting characteristics of the rock within a formation from which the samples were obtained.

Two sets of drill cuttings samples were collected along the depth of a well, both sets of samples comprising samples collected at the same locations along the depth of the well. Both sets of samples were hermetically sealed immediately upon collection ("sealed samples"). The second of the two sets of samples were unsealed at the laboratory, allowed to air dry, and were subjected to laboratory-induced aging as described herein ("lab-aged samples"). The first set of hermetically sealed samples which remained sealed were analyzed for volatile hydrocarbons indicative of oil content, utilizing low vacuum techniques as described herein and in prior applications. The lab-aged samples were crushed after lab-induced aging and then analyzed for volatile hydrocarbons indicative of oil content, using the same vacuum techniques as the sealed samples. The data for the two sample sets are presented in FIG. 34. Results for sealed samples are shown as open circles. Results for lab-aged samples are shown as black squares. The y-axis of the graph is indicative of well depth, the shallowest portion of the represented well depths being at the top of the graph and the deepest portion of the represented well depths being at the bottom of the graph (closest to the x-axis). Volatile hydrocarbon analysis (Total Oil) results are represented on the x-axis.

The sealed at the well samples which remained sealed, indicated by the open circles, as expected, tended to indicate a higher total oil (volatile hydrocarbons indicative of oil content) than that of the lab-aged samples across the depth of well. This is an expected, as it is intuitive that sealed samples would be better at retaining volatile hydrocarbons and would yield a higher response in this analysis. However, within a lower portion of the well, as indicated by the third or bottom set of peaks on the graph of FIG. 34, the lab-aged samples show a higher release of volatile hydrocarbons than the sealed samples. This is an unexpected result, as one would presume that the majority of volatile hydrocarbons present in the sample would have evaporated during the lab-induced aging process. This indicates that the properties of the rock in the lower portion of the well are different than the properties of the rock in the upper portion of the well; more specifically, the properties of the rock in this lower portion of the well are highly oil wetting. The sealed samples collected at that depth, even though subjected to significant vacuum pressures as a function of the volatiles analysis, are not releasing volatile hydrocarbons; whereas the lab-induced aging of the samples modified the structural properties of the rock, e.g., "stiffened" the rock, and the crushing of the samples then led to the release of the hydrocarbons.

This experiment indicates that in oil wetting rock, one is unable to obtain volatile hydrocarbon release simply by application of vacuum pressure. This example further indicates that mechanical disruption of the sampled rock material can provide important information related to the petroleum production capabilities of the location of a formation from which rock samples are obtained that would be missed if only vacuum analysis is applied. FIG. 35 provides the same data as FIG. 34, however is shaded and labeled to clearly present this phenomenon. Solid shading indicates areas of water wetting rock; the diagonally shaded area indicates rock with a high degree of oil wetting.

EXEMPLARY EMBODIMENTS & ASPECTS OF THE INVENTION

The following is a non-limiting list of exemplary aspects of the invention, which is intended to highlight some of the various embodiments of the invention:

In aspects, the invention provides a method of identifying the wettability characteristics of a material comprising (a) providing an analyzable amount of a material; (b) subjecting the material to one or more vacuum pressure conditions of between about 1 millibar and about 100 millibars ("gentle vacuum pressures") for one or more periods to cause the release of a detectable amount of material-associated water; (c) capturing and measuring the amount of the extracted material-associated water released from the material; and (d) characterizing the wettability properties of the material based on the measurement of extracted material-associated water (aspect 1).

In aspects, the invention provides the method of aspect 1, wherein the material is a sample of a larger substance (aspect 2).

In aspects, the invention provides the method of aspect 2, wherein the method comprises obtaining a plurality of samples from different parts of an area of the substance (aspect 3).

In aspects, the invention provides the method of aspect 3, wherein the method comprises obtaining at least 3, 5, or 10 samples from different parts of an area of the substance (aspect 4).

In aspects, the invention provides the method of aspect 4, wherein the method comprises obtaining at least 50 or 100 samples from different parts of an area of the substance (aspect 5).

In aspects, the invention provides the method of aspect 5, wherein the method comprises obtaining at least 250 samples from different parts of an area of the substance (aspect 6).

In aspects, the invention provides the method of any one of aspects 1-6, wherein the substance is rock from a reservoir within a site of an oil production play, such a play optionally being a low visibility oil play (aspect 7).

In aspects, the invention provides the method of aspect 7, wherein the rock is from an oil well drilled in the reservoir (aspect 8).

In aspects, the invention provides the method of aspect 8, wherein the sample is a core sample from an oil well, including but not limited to a sidewall core (aspect 9).

In aspects, the invention provides the method of aspect 9, wherein the samples are petroleum drill cuttings samples (aspect 10).

In aspects, the invention provides the method of aspect 10, wherein the petroleum drill cuttings are rock bit cuttings or PDC cuttings (aspect 11).

In aspects, the invention provides the method of aspect 11, wherein the petroleum drill cuttings are PDC cuttings (aspect 12).

In aspects, the invention provides the method of any one of aspects 5-12, wherein at least some of the samples in the collection are co-located samples, being obtained from an area that is no more than about 100 meters wide in any single direction (aspect 13).

In aspects, the invention provides the method of aspect 13, wherein the co-located samples are obtained from an area that is no more than about 50 meters wide in any single direction (aspect 14).

In aspects, the invention provides the method of aspect 14, wherein the co-located samples are obtained from an area that is no more than about 30 meters wide in any single direction (aspect 15).

In aspects, the invention provides the method of any one of aspects 10-15, wherein at least some, substantially all, or all of the samples are not sealed at the well upon collection (aspect 16).

In aspects, the invention provides the method of any one of aspects 10-15, wherein at least some, substantially all, or all of the samples are hermetically sealed at the well upon collection (aspect 17).

In aspects, the invention provides the method of aspect 17, wherein at least some, substantially all, or all of the samples are hermetically sealed by encapsulation upon collection (aspect 18).

In aspects, the invention provides the method of aspect 18, wherein the encapsulation is accomplished using an encapsulation material which is detectibly or significantly volatile-free encapsulation material (aspect 19).

In aspects, the invention provides the method of any one of aspect 18 or aspect 19, wherein the encapsulation material is selected from the group comprising shrink wrap, tape, or epoxy (aspect 20).

In aspects, the invention provides the method of any one of aspects 1-20, wherein prior to performing step (b) of aspect 1, the material is subjected to a process comprising (1) washing and drying, (2) aging through storage under conditions in which some, most, substantially all, or all of the external water is permitted to evaporate, (3) artificial aging methods that cause substantially all of the external water to be removed from the sample, (4) any other method that removes some, most, substantially all, or all of the external water, or (5) a combination of any or all thereof (aspect 21).

In aspects, the invention provides the method of any one of aspects 10-21, wherein the samples are representative of the rock composition across the depth of an oil well (aspect 22).

In aspects, the invention provides the method of any one of aspects 1-22, wherein the method comprises no physical disruption of at least part of the material (aspect 23).

In aspects, the invention provides the method of any one of aspects 1-22, wherein the method comprises physical disruption of at least part of the material after the application of one or more vacuum pressure conditions (aspect 24).

In aspects, the invention provides the method of aspect 24, wherein the physical disruption occurs after the application of two or more vacuum pressure conditions (aspect 25).

In aspects, the invention provides the method of any one of aspects 1-22, wherein the method comprises physical disruption of at least part of the material prior to the application of at least one vacuum pressure condition (aspect 26).

In aspects, the invention provides the method of aspect 26, wherein the physical disruption occurs prior to the application of two or more vacuum pressure conditions (aspect 27).

In aspects, the invention provides the method of any one of aspects 24-27, wherein physical disruption is accomplished by crushing within a sealed container without incurring any substantial loss of volatiles from the material from the container prior to measurement (aspect 28).

In aspects, the invention provides the method of any one of aspects 1-28, wherein the method comprises the application of 3, 4, 5, or more vacuum conditions (aspect 29).

In aspects, the invention provides the method of any one of aspects 1-29, wherein the method comprises the application of a gradient of vacuum conditions (aspect 30).

In aspects, the invention provides the method of any one of aspects 1-29, wherein an amount of extracted material-associated water released from the material is measured after the application of each vacuum condition, after the application of a physical disruption to the material, or both (aspect 31).

In aspects, the invention provides the method of aspect 30, wherein an amount of extracted material-associated water released from the material is measured at predetermined intervals across a continuous gradient of vacuum conditions (aspect 32).

In aspects, the invention provides the method of aspect 30, wherein an amount of extracted material-associated water released from the material is measured continuously across a gradient of vacuum conditions (aspect 33).

In aspects, the invention provides the method of any one of aspects 1-33, wherein the material comprises minimal fluid inclusions, such that less than about 5%, less than about 3%, or less than about 2% of the water associated with the material originates from inclusions (aspect 34).

In aspects, the invention provides the method of aspect 34, wherein less than about 1%, less than about 0.5%, less than about 0.25%, or less than about 0.1% of the water associated with the material originates from inclusions (aspect 35).

In aspects, the invention provides the method of any one of aspects 1-35, wherein the method comprises exposing the material to an extraction-modulating substance (aspect 36).

In aspects, the invention provides the method of aspect 36, wherein the extraction-modulating substance is a fast-acting tightly-associated liquid-releasing substance (FA-TALRS) (aspect 37).

In aspects, the invention provides the method of any one of aspect 36 or aspect 37, wherein the extraction-modulating substance is a surfactant or a salt (aspect 38).

In aspects, the invention provides the method of any one of aspects 36-38, wherein the material is exposed to an extraction-modulating substance prior to any physical disruption which may be applied to the material (aspect 39).

In aspects, the invention provides the method of any one of aspects 36-38, wherein the material is exposed to an extraction-modulating substance after any physical disruption which may be applied to the material (aspect 40).

In aspects, the invention provides the method of any one of aspects 1-40, wherein the method is performed without extracting easily extracted water (EEW), release resistant water (RRW), or both, from some, most, substantially all, or all samples (aspect 41).

In aspects, the invention provides the method of any one of aspects 1-41, wherein the amount of the extracted material-associated water released from the material comprises at least substantially all of the easily extracted water (EEW) (aspect 42).

In aspects, the invention provides the method of any one of aspects 1-42, wherein the amount of the extracted material-associated water released from the material comprises at least substantially all release resistant water (RRW) capable of being released without physical disruption of the material (aspect 43).

In aspects, the invention provides the method of any one of aspects 1-43, wherein the extracted material-associated water comprises at least some, most, substantially all, or all SRRW, such as RRW-PD (aspect 44).

In aspects, the invention provides the method of any one of aspects 1-44, wherein the amount of the extracted material-associated water released from the material comprises easily extracted water (EEW) and release resistant water (RRW) (aspect 45).

In aspects, the invention provides the method of any one of aspect 24 or aspect 25, wherein the amount of the extracted material-associated water released from the material comprises easily extracted water (EEW), release resistant water (RRW), and at least substantially all release resistant water released upon physical disruption (RRW-PD) (aspect 46).

In aspects, the invention provides the method of any one of aspects 42-46, where each of any EEW, RRW (without physical disruption of the material), or RRW-PD are released under different conditions and each are independently measured (aspect 47).

In aspects, the invention provides the method of aspect 47, wherein the method comprises capturing at least a portion of any EEW, RRW, or RRW-PD by contacting the extraction with a media trap (aspect 48).

In aspects, the invention provides the method of aspect 48, wherein the media trap is cooled to facilitate capture of the extraction(s) and the method optionally comprises a step of heating the trap to release trapped water in a controlled manner (aspect 49).

In aspects, the invention provides the method of aspect 49, wherein the trap reduces the temperature of any contacted water to at least about −65 degrees C. (aspect 50).

In aspects, the invention provides the method of any one of aspects 48-50, wherein the method is performed without cryogenic trapping or any media trapping (aspect 51).

In aspects, the invention provides the method of any one of aspects 1-51, wherein step (b) of the method comprises applying a first vacuum pressure of about 10-50 millibars to the samples to extract EEW, applying at least a second vacuum pressure that is less than about $\frac{1}{3}^{rd}$-$\frac{1}{8}^{th}$ such as about $\frac{1}{3}^{rd}$-$\frac{1}{7}^{th}$, such as about $\frac{1}{4}^{th}$-$\frac{1}{8}^{th}$ or about $\frac{1}{4}^{th}$-$\frac{1}{6}^{th}$ of the pressure applied in a first application of vacuum pressure, and wherein step (c) comprises independently measuring each amount of water released after the application of the first vacuum pressure and second vacuum pressure (aspect 52).

In aspects, the invention provides the method of aspect 52, wherein the at least second vacuum pressure is less than about $\frac{1}{5}^{th}$ of the pressure applied in the first application of vacuum pressure (aspect 53).

In aspects, the invention provides the method of any one of aspect 52 or aspect 53, wherein the at least second vacuum pressure is less than about 5 millibars (e.g., less than about 4 millibars, less than about 3.5 millibars, or less than about 2.5 millibars) (aspect 54).

In aspects, the invention provides the method of any one of aspects 1-54, wherein at least two vacuum pressures are applied to the material, including a first and second vacuum pressures applied as part of a continuous gradient of vacuum pressures, the first vacuum pressure being at least five times greater than the ending vacuum pressure or another vacuum pressure of the gradient, and whereby detectibly or significantly different data or clusters of data are obtained from that obtained by the independent use of the two pressures (aspect 55).

In aspects, the invention provides the method of any one of aspects 45-55, wherein the wettability characteristics of the material are determined (a) based directly upon any one or more of EEW; RRW (without RRW-PD); (b) based on RRW (including RRW-PD); (c) based upon the sum of any two or more of (a); or (d) based on the relationship between any at least two or more of (a) or (b) (aspect 56).

In aspects, the invention provides the method of aspect 56, wherein any one or more measurements are not obtained by mass spectrometry (aspect 57).

In aspects, the invention provides the method of aspect 56, wherein some, most, or all of the material or material samples are initially subjected to cryogenic mass spectrometry volatiles analysis ("CMSVA") prior to performing the measurement of released water (aspect 58).

In aspects, the invention provides the method of any one of aspects 41-58, wherein the measurement of the material-associated water for some, most, substantially all, or all of the samples, is performed by a method comprising Fourier Transform-Infrared Spectroscopy (FTIR), optionally including the application of one or more vacuum pressures, heat, or both (aspect 59).

In aspects, the invention provides the method of any one of aspects 1-59, wherein the measurement of the extracted material-associated water released from the material for some, most, substantially all, or all of the samples is performed by a method comprising, primarily comprising, consisting essentially of, or consisting of the use of capacitance manometry (aspect 60).

In aspects, the invention provides the method of any one of aspects 8-60, wherein the method comprises using the total amount of EEW measured, the sum of EEW and RRW measured, or both, to aid in determining the likelihood of whether a location being or having previously been part of an oil producing system (aspect 61).

In aspects, the invention provides the method of any one of aspects 8-61, wherein the wettability of the material from an oil well indicates a higher probability of, or a higher probability of an increased correlation with, or both, one or more parts of the oil well comprising a pay zone or a well comprising a zone that at one time in the past was a pay zone (aspect 62).

In aspects, the invention provides the method of any one of aspects 17-62, wherein the application of the method to multiple samples is capable of identifying a pay zone or a zone which at one time in the past was a pay zone within a reservoir, within an oil well, within a well that would have been an oil well if the past pay zone was still charged, or any or all thereof (aspect 63).

In aspects, the invention provides the method of any one of aspects 8-63, wherein methods of extracting oil from the oil well are selected at least in part based upon the wettability properties of the rock in which the well is drilled as identified by the application of the method (aspect 64).

In aspects, the invention provides the method of any one of aspects 1-63, wherein decision(s) related to aborting or maintaining operation (prospecting, drilling, extraction, or other petroleum-production-related activity) is made at least in part based on the wettability characteristics of rock within the area as identified by the application of the method (aspect 65).

In aspects, the invention provides the method of any one of aspects 8-65, wherein the method comprises directing petroleum production or exploration operations based on the results of the application of the method (aspect 66).

In aspects, the invention provides the method of any one of aspects 8-66, wherein the material is from an inactive well and the method comprises using the information to start new operations in, from, or around the inactive or non-producing well (aspect 67).

In aspects, the invention provides the method of any one of aspects 8-66, wherein the water analysis is performed at any point in time after of sample collection, such as 1 year, 5 years, 10 years, 25 years, 50 years, 75 years, 100 years, 125 years, or e.g., 150 years after sample collection (aspect 68).

In aspects, the invention provides the method of aspect 68, wherein the water analysis is performed within 1 month of sample collection (aspect 69).

In aspects, the invention provides the method of aspect 69, wherein the water analysis is performed within 1 week, e.g., within 6 days, within 5 days, within 4 days, or within 3 days of sample collection (aspect 70).

In aspects, the invention provides the method of aspect 70, wherein the water analysis is performed within 48 hours of sample collection (aspect 71).

In aspects, the invention provides the method of aspect 71, wherein the water analysis is performed within 24 hours of sample collection (aspect 72).

In aspects, the invention provides the method of aspect 72, wherein the water analysis is performed within 12 hours of sample collection (aspect 73).

In aspects, the invention provides the method of any one of aspects 68-73, wherein the water analysis is performed within 0.5 kilometer or less from the point of collection (aspect 74).

In aspects, the invention provides the method of any one of aspects 66-74, wherein the method comprises using the total amount of EEW measured, the sum of EEW and RRW measured, the amount of RRW-PD measured, the relationship between EEW and RRW (with or without RRW-PD), or any combination of any or all thereof, to direct real time petroleum drilling operations (aspect 75).

In aspects, the invention provides the method of any one of aspects 1-75, wherein the method further comprises comparing the relationship between the results of the application of the method to information obtained through other analytical methods performed on the material or sample(s) or co-located material or samples, such as CMSVA, gamma ray analysis, fluid inclusion analysis, conventional well logging analysis, or any or all thereof (aspect 76).

In aspects, the invention provides the method of aspect 76, wherein one or more measurements obtained by the method correlate with well log Sw, conductance data (e.g., correlate with the inverse of the wireline resistivity log of the sample or co-located material), or both (aspect 77).

In aspects, the invention provides the method of any one of aspects 45-77, wherein the method comprises identifying an area associated with at least one group of samples having an EEW to RRW ratio of at least about 1 or approaching about 1 as having a high probability of petroleum being in or near the area or having been in or near the area in the past (aspect 78).

In aspects, the invention provides the method of any one of aspects 45-77, wherein the method comprises identifying an area associated with at least one group of samples having an EEW to RRW ratio of at least about 1 or approaching about 1 as being indicative of oil wetting rock and having a high probability of the area being a part of an oil producing system (aspect 79).

In aspects, the invention provides the method of aspect 79, wherein the presence of oil wetting rock is indicative of a higher probability of the area being or having been a part of an oil production system (aspect 80).

In aspects, the invention provides the method of any one of aspects 1-80, wherein the method comprises (a) identifying a geographical area of interest; (b) obtaining a first and at least a second set of samples from at least 2, 5, 10, 20, 50, or at least 100 locations within the geographical area of interest, such as each being from separately drilled wells; (c) identifying, from within a first collection of samples from the first location, a group of samples having a mole fraction of EEW which is greater than the mole fraction of RRW, and identifying such a group of samples as representative of a specific location comprising oil-wetting material; (d) combining/compiling and/or comparing the results to that from a corresponding group of samples collected from at least the second location; (e) and using the compilation and/or comparison to determine specific locations of oil-wet rock within the geographical area, the orientation, span, or positioning of petroleum-related geographical features within the geographical area, or any or all thereof (e.g., as may be presented by a map), indicating a higher probability of petroleum production (aspect 81).

In aspects, the invention provides the method of aspect 81, wherein the method is indicative of a high probability of the identified area being or having been at one point in time part of an oil production system (aspect 82).

In aspects, the invention provides the method of any one of aspects 78-82, wherein the area comprises identifying two or more groups of samples in the area that are associated with an EEW to RRW ratio of at least about 1 which are separated by one or more samples having an EEW to RRW ratio of less than about 1 (aspect 83).

In aspects, the invention provides the method of any one of aspects 45-83, wherein the method comprises identifying an area associated with at least one group of samples in which the ratio of EEW to the sum of EEW and RRW is at least about 0.5 or approaching about 0.5 as having a high probability of petroleum being in or near the area (aspect 84).

In aspects, the invention provides the method of aspect 84, wherein the method comprises identifying two or more groups of samples in the area that are associated with an EEW to sum of EEW and RRW ratio of at least about 0.5 or approaching about 0.5 which are separated by one or more samples as having an EEW to sum of EEW and RRW ratio of less than about 0.5 (aspect 85).

In aspects, the invention provides the method of any one of aspects 45-85, wherein the method comprises analyzing whether the samples contain any groups of samples associated with an EEW to RRW ratio of at least about 1, an EEW to sum of EEW and RRW ratio of at least about 0.5, or both (aspect 86).

In aspects, the invention provides the method of any one of aspects 46-85, wherein a collection of samples are subjected to physical disruption after the collection of EEW and RRW, releasing RRW-PD, and wherein within the collection of samples (a) results of water analysis from one or more groups of samples in the collection vary from the results of the same analysis performed on one or more other groups of samples in the collection, (b) results from petroleum-related volatiles analysis from one or more groups of samples in the collection vary from the results of the same analysis performed on one or more other groups of samples in the collection, or (c) both (a) and (b), wherein the variation in the groups of samples identifies differences in oil- and/or water-wettability in the samples (aspect 87).

In aspects, the invention provides the method of aspect 87, wherein a total oil measurement as indicated by the analysis of rock volatiles in a first group of samples is greater than a second group of samples, indicating the first group of samples is oil wetting in their nature (aspect 88).

In aspects, the invention provides a method of identifying the wettability characteristics of rock within an oil reservoir comprising (a) providing an analyzable amount of well-associated material selected from a group comprising petroleum drill cutting(s), core, side wall core, or outcrop rock samples; and (b) subjecting the material to one or more environments selected from the group environments comprising i) an environment characterizable as being under vacuum pressure; ii) an environment characterizable as being saline; and/or iii) an environment characterizable as having surfactant properties, such environment(s) sufficient to cause the release of a detectable amount of material-associated water if present; (c) measuring the amount of the extracted material-associated water released from the cuttings; and (d) characterizing the wettability properties of the material and hence the substance of the reservoir from which they were obtained based on the measurement of extracted material-associated water (aspect 89).

In aspects, the invention provides the method of aspect 89, wherein the method further comprises any steps of one or more of aspects 10-88 (aspect 90).

In aspects, the invention provides a method of using capacitance manometry to identify the wettability characteristics of a material comprising (a) providing an analyzable amount of a material; (b) subjecting the material to one or more environments selected from the group environments comprising (i) an environment characterizable as being under vacuum pressure; (ii) an environment characterizable as being saline; and/or (iii) an environment characterizable as having surfactant properties, such environment(s) sufficient to cause the release of a detectable amount of cuttings-associated water if present; (c) evaluating, via use of capacitance manometry to measure total pressure, the amount of the extracted material-associated water released from the material; and (d) characterizing the wettability properties of the material, and hence the wettability properties of the larger substance/location from which the material was collected, based on the assessment of extracted material-associated water (aspect 91).

In aspects, the invention provides the method of aspect 91, wherein the material is petroleum drill cuttings (aspect 92).

In aspects, the invention provides the method of any one of aspect 91 or aspect 92, wherein the one or more conditions comprises one or more vacuum pressure conditions of between about 1 millibar and about 100 millibars ("gentle vacuum pressures"), e.g., between about 10 and about 100 millibars (aspect 93).

In aspects, the invention provides the method of any one of aspects 91-93, wherein the method further comprises any one or more steps of any one or more of aspects 10-88 (aspect 94).

In aspects, the invention provides the method of aspect 91, wherein the method further comprises any one or more steps of any one or more of aspects 2-88 (aspect 95).

In aspects, the invention provides a method of characterizing a material comprising (a) providing an analyzable amount of a material; (b) measuring the amount of easily extracted water (EEW) in the material; and (c) characterizing the material based on the amount of easily extracted water (EEW) in the material (aspect 96).

In aspects, the invention provides the method of aspect 96, wherein the method comprises characterizing the wettability of the material (aspect 97).

In aspects, the invention provides the method of any one of aspect 96 or aspect 97, wherein the material is a sample of larger substance (aspect 98).

In aspects, the invention provides the method of aspect 98, wherein the method comprises obtaining a plurality of samples from different parts of an area of the substance (aspect 99).

In aspects, the invention provides the method of aspect 99, wherein the method comprises obtaining at least 3, 10, 20, or 50 samples from different parts of an area of the substance (aspect 100).

In aspects, the invention provides the method of aspect 100, wherein the method comprises obtaining at least 75, at least 100, or at least 200 samples from different parts of an area of the substance (aspect 101).

In aspects, the invention provides the method of any one of aspects 98-101, wherein the substance is rock from a reservoir within a site (e.g., a freshwater petroleum site) of an oil production play, such a play optionally being a low visibility oil play (aspect (102).

In aspects, the invention provides the method of aspect 102, wherein the area is an oil well drilled in the reservoir (aspect 103).

In aspects, the invention provides the method of aspect 103, wherein the sample is a core sample from an oil well, including but not limited to a sidewall core (aspect 104).

In aspects, the invention provides the method of aspect 103, wherein the samples are petroleum drill cuttings samples (aspect 105).

In aspects, the invention provides the method of aspect 105, wherein the petroleum drill cuttings are rock bit cuttings or PDC cuttings (aspect 106).

In aspects, the invention provides the method of aspect 106, wherein the petroleum drill cuttings are PDC cuttings (aspect 107).

In aspects, the invention provides the method of any one of aspects 105-107, wherein at least some of the samples in the collection are co-located samples, being obtained from an area that is no more than about 100 meters wide in any single direction (aspect 108).

In aspects, the invention provides the method of aspect 108, wherein the co-located samples are obtained from an area that is no more than about 50 or no more than about 30 meters wide in any single direction (aspect 109).

In aspects, the invention provides the method of any one of aspects 105-109, wherein at least some, substantially all, or all of the samples are not sealed at the well (aspect 110).

In aspects, the invention provides the method of any one of aspects 105-109, wherein at least some, substantially all, or all of the samples are hermetically sealed at the well (aspect 111).

In aspects, the invention provides the method of aspect 111, wherein at least some, substantially all, or all of the samples are hermetically sealed by encapsulation upon collection (aspect 112).

In aspects, the invention provides the method of aspect 112, wherein the encapsulation is accomplished using an encapsulation material which is detectibly or significantly volatile-free encapsulation material (aspect 113).

In aspects, the invention provides the method of aspect 113, wherein the encapsulation material is selected from the group comprising shrink wrap, tape, or epoxy (aspect 114).

In aspects, the invention provides the method of any one of aspects 96-114, wherein prior to performing step (b) of aspect 96, the material is subjected to a process comprising (1) washing and drying, (2) aging through storage under conditions in which substantially all of the external water was permitted to evaporate, (3) artificial aging methods that cause substantially all of the external water to be removed, (4) any other method that removes some, most, substantially all, or all of the external water, or (5) a combination of any or all thereof (aspect 115).

In aspects, the invention provides the method of any one of aspects 105-115, wherein the samples are representative of the rock composition across the depth of an oil well (aspect 116).

In aspects, the invention provides the method of any one of aspects 96-116, wherein prior to step (b), the method comprises application of at least one vacuum condition (aspect 117).

In aspects, the invention provides the method of aspect 117, wherein the method comprises the application of at least two vacuum conditions (aspect 118).

In aspects, the invention provides the method of any one of aspect 117 or aspect 118, wherein the method comprises the application of vacuum condition(s) of between about 1 millibar and about 100 millibars ("gentle vacuum pressures") for one or more periods to cause the release of a detectable amount of water (aspect 119).

In aspects, the invention provides the method of aspect 119, wherein the method comprises the application of at least 2 vacuum conditions (aspect 120).

In aspects, the invention provides the method of aspect 120, wherein a first vacuum pressure of about 10-50 millibars is applied to the samples to extract EEW, and at least a second vacuum condition is applied that is less than about $\frac{1}{3}^{rd}$ of the pressure applied in the first application of vacuum pressure, and wherein step (c) of the method comprises measurement of each amount of water released after the application of the first and second vacuum pressures (aspect 121).

In aspects, the invention provides the method of aspect 121, wherein the at least second vacuum pressure is less than about $\frac{1}{5}^{th}$ of the pressure applied in the first application of vacuum pressure (aspect 122).

In aspects, the invention provides the method of any one of aspects 121-122, wherein the at least second vacuum pressure is less than about 5, 4, or 3 millibars (aspect 123).

In aspects, the invention provides the method of any one of aspects 120-123, wherein the method comprises the application of three or more vacuum conditions (aspect 124).

In aspects, the invention provides the method of aspect 124, wherein the method comprises the application of four or more vacuum conditions (aspect 125).

In aspects, the invention provides the method of aspect 125, wherein the method comprises the application of five or more vacuum conditions (aspect 126).

In aspects, the invention provides the method of any one of aspects 120-126, wherein the method comprises the application of a continuous gradient of vacuum conditions (aspect 127).

In aspects, the invention provides the method of any one of aspects 117-127, wherein an amount of extracted material-associated water released from the material is measured after the application of each vacuum condition, after the optional application of a physical disruption to the material, or both (aspect 128).

In aspects, the invention provides the method of aspect 128, wherein an amount of extracted material-associated water released from the material is measured at predetermined intervals across a gradient of vacuum conditions (aspect 129).

In aspects, the invention provides the method of aspect 128, wherein an amount of extracted material-associated water released from the material is measured continuously across a gradient of vacuum conditions (aspect 130).

In aspects, the invention provides the method of any one of aspects 120-130, wherein any first and second vacuum pressures applied as part of the method vary by at least 5× (e.g., one is at least five times the other) (aspect 131).

In aspects, the invention provides the method of any one of aspects 129-131, wherein detectibly or significantly different data or clusters of data are obtained from that obtained by the utilization of at least two distinct pressures (aspect 132).

In aspects, the invention provides the method of any one of aspects 96-132, wherein the method comprises no physical disruption of at least part of the material (aspect 133).

In aspects, the invention provides the method of any one of aspects 96-132, wherein the method comprises physical disruption of at least part of the material after the application of one or more vacuum pressure conditions (aspect 134).

In aspects, the invention provides the method of any one of aspects 96-132, wherein the method comprises physical disruption of at least part of the material prior to the application of one or more vacuum pressure condition (aspect 135).

In aspects, the invention provides the method of aspect 135, wherein the physical disruption occurs prior to the application of two or more vacuum pressure conditions (aspect 136).

In aspects, the invention provides the method of any one of aspects 134-136, wherein physical disruption is accomplished by crushing within a sealed container without incurring any substantial loss of volatiles from the material from the container prior to measurement (aspect 137).

In aspects, the invention provides the method of any one of aspects 96-137, wherein the material comprises minimal fluid inclusions, such that less than about 5% of the water associated with the material originates from inclusions (aspect 138).

In aspects, the invention provides the method of aspect 138, wherein less than about 3% of the water associated with the material originates from inclusions (aspect 139).

In aspects, the invention provides the method of aspect 139, wherein less than about 1% (e.g., less than about 0.5% or less than about 0.25%) of the water associated with the material originates from inclusions (aspect 140).

In aspects, the invention provides the method of any one of aspects 96-140, wherein the method comprises exposing the material to an extraction-modulating substance (aspect 141).

In aspects, the invention provides the method of aspect 141, wherein the extraction-modulating substance is a fast-acting tightly associated liquid-releasing substance (FA-TALRS) (aspect 142).

In aspects, the invention provides the method of any one of aspect 141 or aspect 142, wherein the extraction modulating substance is a surfactant or a salt (aspect 143).

In aspects, the invention provides the method of any one of aspects 141-143, wherein the material is exposed to an extraction-modulating substance prior to any physical disruption which may be applied to the material (aspect 144).

In aspects, the invention provides the method of any one of aspects 141-143, wherein the material is exposed to an extraction-modulating substance after any physical disruption which may be applied to the material (aspect 145).

In aspects, the invention provides the method of any one of aspects 96-145, wherein the method is performed without extracting release resistant water (RRW), super release resistant water (SRRW) or both from some, most, substantially all, or all of the samples (aspect 146).

In aspects, the invention provides the method of any one of aspects 96-146, wherein the amount of the extracted material-associated water released from the material comprises at least substantially all of the easily extracted water (EEW) (aspect 147).

In aspects, the invention provides the method of any one of aspects 96-147, wherein the amount of the extracted material-associated water released from the material comprises at least substantially all release resistant water (RRW) capable of being released without physical disruption of the material (aspect 148).

In aspects, the invention provides the method of any one of aspects 96-148, wherein the amount of the extracted material-associated water released from the material comprises at least some, most, substantially all, or all SRRW (such as RRW released upon physical disruption of the material (RRW-PD)) (aspect 149).

In aspects, the invention provides the method of aspect 96-149, wherein the amount of the extracted material-associated water released from the material comprises easily extracted water (EEW) and release resistant water (RRW) (aspect 150).

In aspects, the invention provides the method of any one of aspects 134-150, wherein the amount of the extracted material-associated water released from the material comprises easily extracted water (EEW), release resistant water (RRW), and at least substantially all release resistant water released upon physical disruption (RRW-PD), wherein the amount of RRW-PD increases the total amount of extracted material-associated water released from the material over that of the sum of EEW and RRW (aspect 151).

In aspects, the invention provides the method of any one of aspects 96-151, wherein the method comprises determining the amount of release resistant water (RRW) in the material, including or excluding RRW-PD, and characterizing the material based on the sum of EEW+RRW without RRW-PD, the sum of EEW+RRW including RRW-PD, or both (aspect 152).

In aspects, the invention provides the method of any one of aspects 96-152, wherein the method comprises determining the amount of RRW in the material with and/or without RRW-PD, and characterizing the material based on the relationship between two or more of EEW; RRW excluding RRW-PD; RRW including RRW-PD; sum of EEW and RRW excluding RRW-PD; and the sum of EEW and RRW including RRW-PD (aspect 153).

In aspects, the invention provides the method of any one of aspect 152 or aspect 153, the amount of EEW, the amount of RRW excluding RRW-PD, and/or the amount of RRW-PD are obtained under different conditions, such as e.g., different vacuum pressures and/or differences in the mechanical treatment of the sample (aspect 154).

In aspects, the invention provides the method of aspect 154, wherein RRW-PD comprises at least first and second amounts of water released by the physical disruption of the material, each released when the material is subjected to a different condition, such as a change in vacuum pressure (aspect 155).

In aspects, the invention provides the method of aspect 155, wherein RRW-PD comprises a sum of an amount of water released by the physical disruption of the material released over a gradient of conditions, such as a gradient of vacuum pressures (aspect 156).

In aspects, the invention provides a method of characterizing a material comprising (a) providing an analyzable amount of an artificial material; and (b) measuring the amount of material-associated water in the material to assess the wettability characteristics of the material (aspect 157).

In aspects, the invention provides the method of aspect 157, wherein the material is a composition comprising two or more artificial materials (aspect 158).

In aspects, the invention provides the method of aspect 158, wherein the material is used in a manufactured material or device (aspect 159).

In aspects, the invention provides the method of aspect 159, wherein the manufactured material or device is selected from a group comprising but not limited to a material used in electronics or an electronics device, a material used in a medical device or a medical device, a material used in a pharmaceutical product or a pharmaceutical product, or a building material (aspect 160).

In aspects, the invention provides the method of aspect 160, wherein the material is material used in a medical device or pharmaceutical product (aspect 161).

In aspects, the invention provides the method of aspect 160, wherein the material is material used in an electronic device (aspect 162).

In aspects, the invention provides the method of any one of aspects 157-162, wherein the method comprises subjecting the material to one or more conditions under which one or more amounts of material associated water is released, and determining the wettability characteristics of the material based on one or more directly measured or calculated amounts of material associated water released under the one or more conditions (aspect 163).

In aspects, the invention provides the method of any one of aspects 157-163, wherein the method comprises extracting a measurable amount of material associated water through the application of one or more vacuum pressures of between about 1 millibar and about 100 millibars ("gentle vacuum pressures") for one or more periods to cause the release of a detectable amount of material-associated water (aspect 164).

In aspects, the invention provides the method of aspect 164, wherein a first vacuum pressure of approximately 10-50 millibars to the samples to extract a first aliquot of water (easily extracted water, "EEW"), applying at least a second vacuum pressure that is less than about $\frac{1}{3}^{rd}$ of the pressure applied in the first application of vacuum pressure to extract a second aliquot of water (release resistant water, "RRW"), and measuring each amount of water released after the application of the first vacuum pressure and the application of at least the second vacuum pressure independently (aspect 165).

In aspects, the invention provides the method of aspect 165, wherein the at least second vacuum pressure is less than about $\frac{1}{5}^{th}$ of the pressure applied in the first application of vacuum pressure (aspect 166).

In aspects, the invention provides the method of any one of aspect 165 or aspect 166, wherein the at least second vacuum pressure is less than about 5 millibars (aspect 167).

In aspects, the invention provides the method of any one of aspects 164-167, wherein at least two vacuum pressures are applied and the first and at least second vacuum pressures are applied as part of a gradient of vacuum pressures, such that the first vacuum pressure is at least five times the ending vacuum pressure or the any one vacuum pressure of the gradient, and whereby detectibly or significantly different data or clusters of data are obtained from that obtained by the utilization of at least two distinct vacuum pressures (aspect 168).

In aspects, the invention provides the method of any one of aspects 164-168, wherein the method comprises physically disrupting the material such that the physical disruption causes the release of water not released or extracted under vacuum conditions of between 1-100 millibars (RRW-PD) (aspect 169).

In aspects, the invention provides the method of any one of aspects 157-169, wherein the method comprises extracting a measurable amount of RRW including or excluding RRW-PD from the material and analyzing the extracted material-associated water to determine the wettability characteristics of the material (aspect 170).

In aspects, the invention provides the method of any one of aspects 157-170, wherein prior to analysis, the material is subjected to a process comprising (1) washing and drying, (2) aging through storage under conditions in which substantially all of the external water is permitted to evaporate, (3) artificial aging methods that cause substantially all of the external water to be removed from the sample, (4) any other method that removes some, most, substantially all, or all of the external water, or (5) a combination of any or all thereof (aspect 171).

In aspects, the invention provides the method of any one of aspects 157-171, wherein the method comprises exposing the material to an extraction-modulating substance, such as but not limited to a surfactant or a salt (aspect 172).

In aspects, the invention provides the method of any one of aspects 164-172, wherein the wettability characteristics of the material are determined (a) based directly upon any one or more of EEW; RRW (including or excluding RRW-PD); sum of EEW and RRW (including RRW-PD); RRW-PD; sum of EEW and RRW (including or excluding RRW-PD; or (b) based upon the relationship between any two or more of (a); or (c) any combination of (a) and (b) (aspect 173).

In aspects, the invention provides the method of any one of aspects 157-173, wherein the measurement of the material-associated water for some, most, substantially all, or all of the samples, is performed by a method comprising Fourier-TransformInfrared Spectroscopy (FTIR), optionally including application of one or more vacuum pressures, heat, or both (aspect 174).

In aspects, the invention provides the method of any one of aspects 157-173, wherein the measurement of the extracted material-associated water released from the material for some, most, substantially all, or all of the samples is performed by a method comprising use of capacitance manometry (aspect 175).

In aspects, the invention provides the method of any one of aspect 174 or aspect 175, wherein the method optionally comprises use of mass spectrometry (aspect 176).

In aspects, the invention provides the method of aspect 176, wherein the method comprises capturing at least a portion of any EEW or RRW by contacting the extraction with a media trap (aspect 177).

In aspects, the invention provides the method of aspect 177, wherein the media trap is cooled to facilitate capture of the extraction or extractions and the method optionally comprises a step of heating the trap to release trapped water in a controlled manner (aspect 178).

In aspects, the invention provides the method of aspect 178, wherein the trap reduces the temperature of any contacted water to at least about −65 degrees C. (such as a liquid nitrogen trap, a powered refrigerator or other powered cooling system, or a dry ice trap) (aspect 179).

In aspects, the invention provides the method of any one of aspects 177-179, wherein the method does not comprise use of mass spectrometry and is performed without the application of any liquid nitrogen to the material or any released water (aspect 180).

In aspects, the invention provides a method of assessing the characteristics of a material comprising providing an analyzable amount of the material and applying a fast-acting tightly-associated liquid (TAL)-releasing substance (FA-TALRS) to the material, wherein the FATALRS is capable of releasing a visually detectable amount of TAL from the material within a period of less than about 1 hour (aspect 181).

In aspects, the invention provides the method of aspect 181, wherein the FATALRS comprises an effective amount of one or more polyphenolic compounds (aspect 182).

In aspects, the invention provides the method of aspect 182, wherein the one or more polyphenolic compounds comprise chlorogenic acid (CGA), one or more diterpenes, trans-cinnamic acids (e.g., caffeic, ferulic and p-coumaric acids), or a combination of any or all thereof (aspect 183).

In aspects, the invention provides the method of aspect 183, wherein the FATALRS is an aqueous solution comprising about 0.1-1.5% of the one or more polyphenolic compounds (aspect 184).

In aspects, the invention provides the method of aspect 184, wherein the water content of the FATALRS is at least about 80% (aspect 185).

In aspects, the invention provides the method of any one of aspects 181-185, wherein the material is an artificial (e.g., a man-made) material (aspect 186).

In aspects, the invention provides the method of any one of aspects 181-185, wherein the material is a naturally occurring material (aspect 187).

In aspects, the invention provides the method of aspect 187, wherein the material is a geological material (aspect 188).

In aspects, the invention provides the method of aspect 188, wherein the material is rock from a petroleum drilling or petroleum exploration operation (aspect 189).

In aspects, the invention provides the method of aspect 189, wherein the material is petroleum drill cuttings collected from an oil well (aspect 190).

In aspects, the invention provides the method of aspect 190, wherein the cuttings are rock bit cuttings or PDC cuttings (aspect 191).

In aspects, the invention provides the method of aspect 191, wherein the petroleum drill cuttings are PDC cuttings (aspect 192).

In aspects, the invention provides the method of any one of aspects 181-192, wherein the TAL is a hydrophobic liquid (aspect 193).

In aspects, the invention provides the method of aspect 193, wherein the TAL comprises oil (aspect 194).

In aspects, the invention provides the method of any one of aspects 190-194, wherein the cuttings have not been subjected to any previous analytical methods prior to the application of the method (aspect 195).

In aspects, the invention provides the method of any one of aspects 190-194, wherein the cuttings have been subjected to at least one previous analytical method prior to the application of the method (aspect 196).

In aspects, the invention provides the method of aspect 196, wherein the cuttings have been subjected to one or more methods described by one or more of aspects 1-180 (aspect 197).

In aspects, the invention provides the method of any one of aspect 181-197, wherein the method is capable of characterizing the oil-wetting, the water-wetting, or both the oil- and water-wetting characteristic(s) of the material (aspect 198).

In aspects, the invention provides the method of aspect 198, wherein the characterization of petroleum drill cuttings as oil- or water-wetting by application of the method is utilized to (a) characterize a petroleum drilling site, a well within a petroleum drilling site, or a specific location within a well of a petroleum drilling site, (b) make decisions about how to extract oil from a well within a petroleum drilling site, (c) make decisions about the future use of a geological area (such as a play or a site within a play), or (d) any or all thereof (aspect 199).

In aspects, the invention provides a method of identifying the oil-wetting nature of a sample of material obtained from a geological area to identify one or more oil-producing and/or oil-wet locations within the geological area comprising a. obtaining from two or more locations within a geologic formation
  i. two sets of samples, each set having samples collected from the same locations within the geologic formation; one set of samples having been hermetically sealed upon collection, and one set not sealed at the well upon collection, or
  ii. a single set of samples hermetically sealed upon collection which is
    1. later divided into two sets of samples such that one set is identifiable as hermetically sealed and one set is identified as unsealed, or
    2. first analyzed as a hermetically sealed sample then reanalyzed after further sample preparation;
b. subjecting the second set of samples identified as unsealed or alternatively having first been analyzed as a sealed sample to aging through storage under conditions in which external water is permitted to evaporate ("lab-aged");
c. measuring two or more volatile hydrocarbons in sealed samples extracted under vacuum conditions by any process capable of applying such conditions and providing such a total oil indication (oil response), if present, without mechanically disrupting the physical structure of the samples;
d. subjecting the unsealed, lab-aged samples, or alternatively the sealed samples having completed step (c) to physical disruption (e.g., crushing), and measuring the same two or more volatile hydrocarbons extracted under vacuum conditions by any process capable of applying such conditions;

e. collecting a total oil indication (oil response), if present, from each sample analyzed in (c) and (d);

f. identifying variations in the responses between the two sample sets of (c) and (d) as measured by (e), wherein a lab-aged sample having a higher total volatile hydrocarbon (oil response) result than that measured in a sealed sample obtained from the same location is indicative of oil wetting rock at that location (aspect 200).

In aspects, the invention provides the method of aspect 200, wherein locations identified as oil wetting indicate a higher probability of a present-day or past petroleum deposit (aspect 201).

In aspects, the invention provides the method of aspect 201, wherein if an identified oil-wetting location is not a present-day petroleum deposit, the presence of oil-wetting rock is indicative of a higher probability of oil within the geological area (aspect 202).

In aspects, the invention provides a method of identifying the oil- versus water-wetting characteristic of a material without changing the physical structure of the material being analyzed, comprising subjecting the material to a. one or more vacuum conditions;

b. one or more temperature conditions;

c. one or more immediate environmental conditions (e.g., conditions having a polyphenolic, saline or surfactant nature); or d. any combination of one or more of (a)-(c), wherein modifying one or more of (a)-(d) changes the amount of oil, volatile hydrocarbons, water, or both volatile hydrocarbons or water released from the material, and further wherein changes in the amount of oil, volatile hydrocarbons, water, or both volatile hydrocarbons or water released from the material under varying any one or more of (a)-(d) is representative of the oil- or water-wetting characteristic of a material (aspect 203).

In aspects, the invention provides the method of aspect 203, wherein the material comprises a naturally occurring material or an artificial, manufactured, or otherwise man-made material (aspect 204).

In aspects, the invention provides the method of aspect 204, wherein the material is a naturally occurring material (aspect 205).

In aspects, the invention provides the method of aspect 205, wherein the material is rock (aspect 206).

In aspects, the invention provides the method of aspect 206, wherein the rock is a core sample from an oil well, a portion of a core sample from an oil well, or drill cuttings from an oil well (aspect 207).

In aspects, the invention provides the method of aspect 207, wherein the identification of an oil-wetting nature of the material being analyzed is indicative of a higher probability of location of a petroleum production area (pay zone) or a location having a higher probability of being a part of a present day or past petroleum production system (aspect 208).

In aspects, the invention provides a method of quickly determining the oil wetting nature of a material comprising a. providing a panel of substances comprising
   i. one or more polyphenolic compounds, each polyphenolic compound(s) varying from any other polyphenolic compound in at least one chemical property;
   ii. one or more surfactants, each surfactant varying from any other surfactant in at least one chemical property;
   iii. one or more saline solutions, each saline solution varying from any other saline solution in at least one chemical property (e.g., percent salinity or type of salt); or
   iv. a combination of any two or more of (i)-(iii);

b. placing the material or a sample of the material into each of the substances of the panel of (a); and c. evaluating the response of the material to the substance by
   v. visually inspecting the effect of the substance on the material, such as but not limited to visually inspecting the release of oil from the material; or
   vi. measuring one or more changes in the substances after receiving the material by an automated method capable of detecting one or more changes to the substances after receiving the material (aspect 209).

In aspects, the invention provides the method of aspect 209, wherein the material comprises a naturally occurring material or an artificial, manufactured, or otherwise man-made material (aspect 210).

In aspects, the invention provides the method of aspect 210, wherein the material is a naturally occurring material (aspect 211).

In aspects, the invention provides the method of aspect 211, wherein the material is rock (aspect 212).

In aspects, the invention provides the method of aspect 212, wherein the rock is drill cuttings from an oil well (aspect 213).

In aspects, the invention provides the method of any one of aspects 209-213, wherein visual inspection comprises use of a microscope (aspect 214).

In aspects, the invention provides the method of any one of aspects 209-214, wherein one or more changes in one or more substances after receiving the material is an increased content of oil (aspect 215).

In aspects, the invention provides the method of aspect 215, wherein a detectible or significant increase in the content of oil of a substance after having made contact with the material is indicative of the material releasing oil and thus indicative of the oil-wetting nature of the material (aspect 216).

In aspects, the invention provides a method of screening for fast-acting tightly-associated liquid (TAL)-releasing substances ("FATALRSs") capable of releasing a visually detectable amount of TAL from a material within a given period comprising a. providing a panel of at least two potential FATALRSs, each varying from one another based upon one or more chemical properties, concentration, or both, for which one or more initial ("baseline") characteristic is known;

b. obtaining a sufficient amount of a material;

c. combining a representative sample of the material with each of the potential FATALRSs of the panel;

d. measuring the change in the at least one baseline characteristic of the potential FATALRSs (aspect 217).

In aspects, the invention provides the method of aspect 217, wherein the potential FATALRSs being screened are selected from a group comprising substances having a polyphenolic, saline, surfactant, acid, base, organic, inorganic, polar, non-polar, oxidizing, or reducing nature or any combination of any or all thereof (aspect 218).

In aspects, the invention provides the method of aspect 218, wherein the potential FATALRSs being screened are selected from a group comprising substances having a polyphenolic, saline, or surfactant nature (aspect 219).

In aspects, the invention provides the method of aspect 234, wherein any one or more potential FATALRSs shares one or more components with those found in coffee (aspect 220).

In aspects, the invention provides the method of any one of aspects 217-221, wherein the TAL released from the material is selected from a group comprising water or one or more oils (aspect 221).

In aspects, the invention provides the method of aspect 221, wherein the TAL is water (aspect 222).

In aspects, the invention provides the method of aspect 221, wherein the TAL is an oil (aspect 223).

In aspects, the invention provides the method of any one of aspects 217-223, wherein the material is an artificial (man-made) material (aspect 224).

In aspects, the invention provides the method of any one of aspects 217-223, wherein the material is a natural material (aspect 225).

In aspects, the invention provides the method of aspect 225, wherein the material is a geological material (aspect 226).

In aspects, the invention provides the method of aspect 226, wherein the material is rock (aspect 227).

In aspects, the invention provides the method of aspect 227, wherein the rock is collected from a petroleum drilling operation (aspect 228).

In aspects, the invention provides the method of aspect 228, wherein the rock is a core sample (aspect 229).

In aspects, the invention provides the method of aspect 228, wherein the rock is drill cuttings (aspect 230).

In aspects, the invention provides the method of aspect 230, wherein the drill cuttings are rock bit cuttings (aspect 231).

In aspects, the invention provides the method of aspect 230, wherein the drill cuttings are PDC cuttings (aspect 232).

In aspects, the invention provides the method of any one of aspects 217-232, wherein the given period is less than 3 hours (aspect 233).

In aspects, the invention provides the method of aspect 233, wherein the given period is less than 2 hours (aspect 234).

In aspects, the invention provides the method of aspect 234, wherein the given period is less than 1 hour (aspect 235).

In aspects, the invention provides the method of aspect 235, wherein the given period is less than 30 minutes (aspect 236).

In aspects, the invention provides the method of any one of aspects 217-236, wherein the panel comprises at least 5 potential FATALRSs (aspect 237).

In aspects, the invention provides the method of aspect 237, wherein the panel comprises at least 10 potential FATALRSs (aspect 238).

In aspects, the invention provides the method of aspect 238, wherein the panel comprises at least 25 potential FATALRSs (aspect 239).

In aspects, the invention provides the method of aspect 239, wherein the panel comprises at least 50 potential FATALRSs (aspect 240).

In aspects, the invention provides the method of aspect 240, wherein the panel comprises at least 96 potential FATALRSs (aspect 241).

In aspects, the invention provides the method of any one of aspects 217-241; wherein the one or more baseline characteristics of the potential FATALRSs known prior to the addition of a subject test material is selected from a group comprising visual appearance, concentration, color, viscosity, oil content, light absorbance, light reflectance, osmolality or osmolarity, uniformity of mixing, or an element representative of petroleum oil content (aspect 242).

In aspects, the invention provides the method of any one of aspects 217-242, wherein a detectible or significant change in the one or more baseline characteristics of the potential FATALRSs after the given period is indicative of a release of a TAL from the material (aspect 243).

In aspects, the invention provides the method of aspect 243, wherein the change in the one or more baseline characteristics is detected using technology selected from a group comprising the naked eye, microscopy, spectroscopy, spectrophotometry, colorimetry, photometry, viscometry, and osmometry (aspect 244).

In aspects, the invention provides the method of any one of aspects 217-244, wherein the method comprises an indicator such that potential FATALRS(s) are identified by a characteristic other than one inherent to the substance (e.g., a change in the indicator status), if the potential FATALRS(s) is capable of releasing a TAL from the material, such a characteristic being present due to the indicator and detected in step (d) of the method (aspect 245).

In aspects, the invention provides the method of any one of aspects 217-245, wherein any FATALRS(s) identified by application of the method as being capable of releasing TAL are selected for use in one or more material-associated liquid analysis methods (aspect 246).

In aspects, the invention provides an analytical device or system for analyzing samples obtained from a geologic formation comprising (a) a component for receiving a sample, (b) (i) an analyzer capable of analyzing a first aliquot of target analyte (such as EEW) from a sample after the application of a first condition to the sample, (ii) an analyzer capable of analyzing a second aliquot of target analyte (such as RRW) from a sample after the application of a second condition to the sample, (iii), optionally an analyzer capable of analyzing a third aliquot of target analyte (such as SRRW) from a sample after the application of a third condition to the sample, or (iv) an analyzer capable of analyzing aliquots collected after each application of a plurality of conditions; (b) a processor for computing the sum and/or relationship between any two or more aliquots or calculations based on one or more aliquots; and (c) a display for displaying results of any aliquot analysis and the results of any calculations made therefrom (aspect 247).

In aspects, the invention provides the device of aspect 247, further comprising a media for capturing and concentrating any one or more aliquots described in aspect 247, wherein the one or more analyzers measure the amount of water captured or released by the media (aspect 248).

In aspects, the invention provides the device of any one of aspect 247 or aspect 248, wherein the device or system further comprises an extractor capable of extracting at least a first aliquot upon the application of a first condition, an extractor capable of extracting at least a second aliquot upon the application of a second condition, or an extractor capable of extracting a plurality of aliquots upon each of the applications of a plurality of conditions (aspect 249).

In aspects, the invention provides the device or system of any one of aspects 247-249, wherein the device or system comprises a protection component or system for isolating samples from environmental exposure to water while in the device or system (aspect 250).

In aspects, the invention provides the device or system of any one of aspects 247-250, comprising one or more capacitance manometers (aspect 251).

In aspects, the invention provides the device or system of any one of aspects 247-251, wherein the device or system comprises a cooling component that selectively cools a water trapping media to at least about −65 degrees C. (aspect 252).

In aspects, the invention provides the device or system of any one of aspects 247-252, wherein the device or system is incorporated into or is otherwise in communication with a device or system configured for performing cryogenic mass spectrometry volatiles analysis of samples (aspect 253).

In aspects, the invention provides the device of any one of aspects 247-253, wherein the device or system lacks any mass spectrometer, lacks any liquid nitrogen container, or lacks both (aspect 254).

In aspects, the invention provides a device or system for analyzing likelihood of association of petroleum with a geologic formation comprising (a) means for analyzing EEW, (b) means for analyzing RRW, (c) means for summing and/or comparing EEW to RRW and/or total water, and (d) means for displaying the results of the analysis (aspect 255).

In aspects, the invention provides a method of analyzing a group of samples from a geologic formation comprising (a) step for measuring EEW, (b) step for measuring RRW, (c) step for summing EEW and RRW and/or comparing EEW to RRW and/or total water, and (d) step for relaying the results of the comparison (aspect 256).

In aspects, the invention provides an analytical device or system for analyzing the tightly-associated liquid (TAL) characteristics of a material, comprising (a) a component for receiving one or more samples of material, (b) (i) an analyzer capable of establishing a baseline value for one or characteristics related to one or more FATALRS(s), and (ii) an analyzer capable of detecting the change in one or more characteristics of one or more FATALRS(s); wherein (i) and (ii) can optionally be the same analyzer; (c) a processor for analyzing the change in one or more characteristics related to the FATALRS(s) between the baseline value and a final value; and (d) a display for displaying results of any direct analysis and the results of any processed data resulting therefrom (aspect 257).

In aspects, the invention provides the device or system of aspect 257, wherein the component for receiving one or more samples of a material is a component capable of receiving a plurality of samples of a material (aspect 258).

In aspects, the invention provides the device or system of any one of aspect 257 or aspect 258, wherein the device or system further comprises a means of dispensing the one or more FATALR(s) into the one or more samples of material (aspect 259).

In aspects, the invention provides the device or system of aspect 259, wherein the device or system further comprises a component capable of controllably mixing of the combined FATALRS(s) and samples of material (aspect 260).

In aspects, the invention provides the device or system of any one of aspects 257-260, wherein the device or system further comprises a component capable of tracking a programmable or established time period or the passage of time (aspect 261).

In aspects, the invention provides the device or system of any one of aspects 257-261, wherein the device or system comprises one or more detectors selected from a group of technologies comprising spectroscopy, spectrophotometry, colorimetry, photometry, viscometry, and osmometry (aspect 262).

In aspects, the invention provides the device or system of aspect 262, wherein, (a) upon the combination of one or more FATALRS(s) with one or more samples, (i) a predetermined period of time is allowed to pass; (ii) the one or more detectors of aspect 262 are applied to analyze the one or more characteristics of the one or more FATALRS(s); and (iii) the results of (ii) are compared to baseline values for the one or more characteristics of the FATALRS(s); wherein any statistically significant change in the one or more characteristics from baseline is indicative of the release of a TAL from the sample (aspect 263).

In aspects, the invention provides the device or system of any one of aspects 257-263, wherein the device is capable of receiving a plurality of samples of material and the material provided is petroleum drill cuttings, wherein the plurality of drill cutting samples are representative of the rock present at a plurality of locations across a drilled oil well, and wherein the device or system is capable of detecting differences in the characteristics of the rock based upon the TAL released from the cuttings samples analyzed by the device, wherein the TAL is oil (aspect 264).

In aspects, the invention provides the device or system of any one of aspects 257-264, wherein the device or system is capable of receiving data about each sample provided to the device or system (aspect 265).

In aspects, the invention provides the device or system of aspect 265, wherein the processor is capable of generating a report based upon data available about each sample and the results of sample analysis (aspect 266).

In aspects, the invention provides the device or system of aspect 266, wherein the report generated is a report identifying locations within an oil well comprising oil-wet rock (aspect 267).

In aspects, the invention provides a device, system, or method of any of the preceding aspects, wherein the amount of EEW in the material is equal to the amount of water extractable by applying a vacuum pressure of about 10- about 30 millibars (e.g., about 12- about 29 millibars or about 14-26 millibars) on the material for a period of about 5- about 20 minutes (e.g., about 6-18 minutes or about 7-17 minutes), +/−20%, +1-15%, +/−10%, +1-5%, +/−2%, or +/− about 1% (aspect 268).

The invention claimed is:

1. A method of characterizing a material comprising (a) providing an analyzable amount of the material; (b) measuring the amount of easily extracted water (EEW) in the material; and (c) characterizing the material based on the amount of EEW in the material, wherein the amount of EEW in the material is equal to the amount of water extractable by applying a vacuum pressure of about 10- about 30 millibars to the material for a period of about 4-24 minutes.

2. The method of claim 1, wherein the method comprises characterizing the wettability of the material based on the amount of EEW in the material and optionally further based on the amount of release resistant water (RRW) in the material.

3. The method of claim 2, wherein the material comprises a plurality of samples from different parts of a larger substance, and areas of the substance are characterized on the basis of EEW released from the samples.

4. The method of claim 3, wherein the method comprises obtaining samples from more than 100 different parts of an area of the substance.

5. The method of claim 4, wherein the substance is rock from an oil well.

6. The method of claim 5, wherein the samples are petroleum drill cuttings samples representative of the rock composition across or along the depth or length of a portion of the oil well.

7. The method of claim 6, wherein at least 90% of the petroleum drill cuttings are PDC cuttings, at least 50% of the portion of the well is a horizontal (at least primarily horizontally oriented) well, or both.

8. The method of claim 2, wherein prior to step (b) of the method, the method comprises the application of at least one vacuum condition of between about 1 millibar and about 100 millibars to the material to extract EEW from the material.

9. The method of claim 8, wherein the one or more vacuum condition(s) are between about 10 millibars and about 100 millibars of vacuum for one or more periods to cause the release of a detectable amount of water.

10. The method of claim 9, wherein the method comprises applying at least 2 vacuum conditions to the material to extract water from the material.

11. The method of claim 10, wherein a first vacuum pressure of about 10-50 millibars is applied to the samples to extract EEW, and at least a second vacuum condition is separately applied that is less than about $\frac{1}{3}^{rd}$ to about $\frac{1}{8}^{th}$ of the pressure applied in the first application of vacuum pressure to release RRW (release resistant water) from the material, and wherein the method further comprises measuring each of EEW and RRW released after the application of the first and at least second vacuum pressures.

12. The method of claim 10, wherein the method comprises physical disruption of at least part of the material before or after the application of one or more vacuum pressure conditions, and in which the physical disruption is accomplished by crushing the material within a sealed container without incurring any substantial loss of volatiles including water from the material from the container prior to measurement.

13. The method of claim 12, wherein the amount of the extracted material-associated water released from the material comprises a measurable amount of a super release resistant water (SRRW) in the material that would not have been released but for the application of the physical disruption or a correspondingly effective force, condition, or combination thereof.

14. The method of claim 13, wherein the method comprises determining the wettability of the material based upon the amount of EEW measured; the amount of RRW, with or without an optionally obtained SRRW, measured; the sum of EEW and RRW (including or excluding SRRW) measured; or the relationship between two or more of EEW, RRW (including or excluding any measured SRRW), and the sum of EEW and RRW (including or excluding ay measured SRRW).

15. The method of claim 7, wherein the identification of an oil-wet nature of the material is indicative of a higher probability of the presence of petroleum at the location from which the sample was obtained or indicative of the location from which the sample was obtained being within a petroleum producing geological area.

16. The method of claim 9, wherein the identification of an oil-wet nature of the material is indicative of a higher probability of the presence of petroleum at the location from which the sample was obtained or indicative of the location from which the sample was obtained being within a petroleum producing geological area.

17. The method of claim 10, wherein the identification of an oil-wet nature of the material is indicative of a higher probability of the presence of petroleum at the location from which the sample was obtained or indicative of the location from which the sample was obtained being within a petroleum producing geological area.

18. The method of claim 11, wherein the identification of an oil-wet nature of the material is indicative of a higher probability of the presence of petroleum at the location from which the sample was obtained or indicative of the location from which the sample was obtained being within a petroleum producing geological area.

19. The method of claim 12, wherein the identification of an oil-wet nature of the material is indicative of a higher probability of the presence of petroleum at the location from which the sample was obtained or indicative of the location from which the sample was obtained being within a petroleum producing geological area.

20. The method of claim 14, wherein the identification of an oil-wet nature of the material is indicative of a higher probability of the presence of petroleum at the location from which the sample was obtained or indicative of the location from which the sample was obtained being within a petroleum producing geological area.

* * * * *